(12) United States Patent
Lefkowitz et al.

(10) Patent No.: US 11,866,482 B2
(45) Date of Patent: Jan. 9, 2024

(54) SYSTEM AND METHOD FOR HOMOGENOUS GPCR PHOSPHORYLATION AND IDENTIFICATION OF BETA-2 ADRENERGIC RECEPTOR POSITIVE ALLOSTERIC MODULATORS

(71) Applicant: Duke University, Durham, NC (US)

(72) Inventors: Robert J. Lefkowitz, Durham, NC (US); Seungkirl Ahn, Durham, NC (US); Biswaranjan Pani, Durham, NC (US); Alem W. Kahsai, Durham, NC (US); Laura Wingler, Durham, NC (US); Dean Staus, Durham, NC (US)

(73) Assignee: Duke University, Durham, NC (US)

(*) Notice: Subject to any disclaimer, the term of this patent is extended or adjusted under 35 U.S.C. 154(b) by 1247 days.

(21) Appl. No.: 16/269,877

(22) Filed: Feb. 7, 2019

(65) Prior Publication Data
US 2019/0241642 A1 Aug. 8, 2019

Related U.S. Application Data

(60) Provisional application No. 62/627,678, filed on Feb. 7, 2018, provisional application No. 62/627,680, filed on Feb. 7, 2018.

(51) Int. Cl.
| | | |
|---|---|---|
| C07K 16/28 | (2006.01) | |
| C07K 14/72 | (2006.01) | |
| C07K 14/705 | (2006.01) | |
| C07K 14/47 | (2006.01) | |
| G01N 33/68 | (2006.01) | |
| C07K 19/00 | (2006.01) | |

(52) U.S. Cl.
CPC ........ *C07K 14/723* (2013.01); *C07K 14/4703* (2013.01); *C07K 14/70567* (2013.01); *C07K 14/70571* (2013.01); *C07K 19/00* (2013.01); *G01N 33/6872* (2013.01); *C07K 2319/00* (2013.01); *C07K 2319/70* (2013.01); *G01N 2333/726* (2013.01); *G01N 2500/02* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | |
|---|---|---|
| 6,555,583 B2 | 4/2003 | Nieman et al. |
| 6,702,997 B2 | 3/2004 | Chaudry et al. |
| 6,894,041 B2 | 5/2005 | Marfat et al. |
| 7,553,971 B2 | 6/2009 | Moran et al. |
| 8,969,571 B2 | 3/2015 | Mammen et al. |
| 2002/0106739 A1 | 8/2002 | Oakley et al. |
| 2014/0249296 A1 | 9/2014 | Ploegh et al. |

FOREIGN PATENT DOCUMENTS

WO WO 2008/021552 A2 2/2008

OTHER PUBLICATIONS

Ahn et al., "Small-Molecule Positive Allosteric Modulators of the β2-Adrenoceptor Isolated from DNA-Encoded Libraries," Mol Pharmacol, 2018, 94(2):850-861.
Ahn et al., "Allosteric "beta-blocker" isolated from a DNA-encoded small molecule library," Proc Natl Acad Sci USA, 2017, 114(7):1708-1713.
Amer et al., "Rapid Addition of Unlabeled Silent Solubility Tags to Proteins Using a New Substrate-Fused Sortase Reagent," J. Biomol. NMR, 2016, 64(3):197-205.
Antos et al., "Recent advances in sortase-catalyzed litigation methodology," Current Opinion in Structural Biology, 2016, 38:111-118.
Antos et al., "Lipid modification of proteins through sortase-catalyzed transpeptidation," J Am Chem Soc, 2008, 130(48):16338-16343.
Attwood et al., "Fingerprinting G-protein-coupled receptors," Protein Engineering, 1994, 7(2):195-203.
Bellucci et al., ""Three-in-one" chromatography-free purification, tag removal, and site-specific modification of recombinant fusion proteins using Sortase A and elastin-like polypeptides," Angew Chem Int Ed Engl, 2013, 52(13):3703-3708.
Benovic et al., "Functional desensitization of the isolated ß-adrenergic receptor by the ß-adrenergic receptor kinase: potential role of an analog of the retinal protein arrestin (48-kDa protein)," Proc Natl Acad Sci USA, 1987, 84(24):8879-8882.
Berge et al., "Pharmaceutical salts," J Pharmaceutical Sciences, 1977, 66, 1-19.
Berrade et al., "Expressed protein ligation: a resourceful tool to study protein structure and function," Cell. Mol. Life Sci., 2009, 66(24):3909-3922.
Bjarnadóttir et al., "Comprehensive repertoire and phylogenetic analysis of the G protein-coupled receptors in human and mouse," Genomics, 2006, 88(3):263-73.
Butcher et al., "Differential G-protein-coupled receptor phosphorylation provides evidence for a signaling bar code," J Biol Chem, 2011, 286(13):11506-11518.

(Continued)

*Primary Examiner* — Michael D Pak
(74) *Attorney, Agent, or Firm* — Michael Best & Friedrich LLP

(57) ABSTRACT

The disclosure is directed to a G-protein coupled receptor complex. The complex includes (i) a chimeric G protein-coupled receptor (GPCR) comprising a non-native amino acid sequence located within the C-terminus of the GPCR and a synthetic phosphopeptide ligated to the non-native amino acid sequence; and (ii) a β-arrestin (βarr) protein bound to the C-terminus of the GPCR. The disclosure also provides an in vitro method for producing the aforementioned complex, as well as methods for identifying compounds or ligands which bind to and modulate the activity of the complex. Positive allosteric modulators of the β2 adrenergic receptor identified by screening a DNA-encoded library potentiate the activity of β2 agonists and have application in the treatment of obstructive airway disease, bronchospasm, or pre-term labor.

6 Claims, 45 Drawing Sheets

Specification includes a Sequence Listing.

(56) References Cited

OTHER PUBLICATIONS

C.T.F.A. Cosmetic Ingredient Handbook, 1992, pp. 587-592.
Cahill III et al., "Distinct conformations of GPCR-ß-arrestin complexes mediate desensitization, signaling, and endocytosis," Proc Natl Acad Sci USA, 2017, 114(10):2562-2567.
Carter et al., "Characterization of Isoprenaline- and Salmeterol-Stimulated Interactions between $\beta_2$-Adrenoceptors and β-Arrestin 2 Using β-Galactosidase Complementation in C2C12 Cells," Journal of Pharmacology and Experimental Therapeutics, 2005, 315(2):839-848.
Charest et al., "Monitoring agonist-promoted conformational changes of β-arrestin in living cells by intramolecular BRET," EMBO Reports, 2005, 6(4):334-340.
Chen et al., "A general strategy for the evolution of bond-forming enzymes using yeast display," Proc Natl Acad Sci USA, 2011, 108(28):11399-11404.
Chen et al., "Sortase A-mediated multi-functionalization of protein nanoparticles," Chem. Commun., 2015, 51(60):12107-12110.
Christopoulos et al., "International Union of Basic and Clinical Pharmacology. XC. multisite pharmacology: recommendations for the nomenclature of receptor allosterism and allosteric ligands," Pharmacol Rev, 2014, 66(4):918-947.
Das et al., "Structure and specificity of new class of Ca2+ -independent housekeeping sortase from Streptomyces avermitilis provide insights into its non-canonical substrate preference," J. Biol. Chem., 2017, 292(17):7244-7257.
De Lean et al., "A ternary complex model explains the agonist-specific binding properties of the adenylate cyclase-coupled beta-adrenergic receptor," J Biol Chem, 1980, 180, 255(15):7108-7117.
Denisov et al., "Nanodiscs for structural and functional studies of membrane proteins," Nat Struct Mol Biol, 2016, 23(6):481-486.
DeWire et al., "β-Arrestins and Cell Signaling," Annu Rev Physiol, 2007, 69:483-510.
Dorr et al., "Reprogramming the specificity of sortase enzymes," PNAS, 2014, 11(37):13343-13348.
Fang et al., "Structurally-defined αMHC-II nanobody-drug conjugates: Therapeutic and imaging platforms for B-cell lymphoma," Angew Chem Int Ed Engl, 2016, 55:2416-2420.
Foord et al., "International Union of Pharmacology. XLVI. G protein-coupled receptor list," Pharmacological Reviews, 2005, 57(2):279-288.
Franciosi et al., "Efficacy and safety of RPL554, a dual PDE3 and PDE4 inhibitor, in healthy volunteers and in patients with asthma or chronic obstructive pulmonary disease: fidings from four clinical trials," Lancet Respir Med, 2013, 14 pages.
Franzini et al., "Chemical Space of DNA-Encoded Libraries," J Med Chem, 2016, 59(14):6629-6644.
Genentech, Inc., XOLAIR, Omalizumab, 2003, 17 pages.
Gilman, "G proteins: transducers of receptor-generated signals," Annu. Rev. Biochem., 1987, 56:615-649.
Godbole et al., "Internalized TSH receptors en route to the TGN induce local $G_s$-protein signaling and gene transcription," Nat Commun, 2017, 8(1):443, 15 pages.
Goddard et al., "Reconstitution of membrane proteins: a GPCR as an example," Methods Enzymol., 2015, 556:405-424.
Goodman et al., "β-Arrestin acts as a clathrin adaptor in endocytosis of the $\beta_2$-adrenergic receptor," Nature, 1996, 383(6599):447-450.
Gregorio et al., "Single-molecule analysis of ligand efficacy in $\beta_2$AR-G-protein activation," Nature, 2017, 547(7661):68-73.
Gurevich, "The Selectivity of Visual Arrestin for Light-activated Phosphorhodopsin Is Controlled by Multiple Nonredundant Mechanisms," J. Biol. Chem., 1998, 273(25):15501-15506.
Gurevich et al., "The molecular acrobatics of arrestin activation," Trends Pharmacol. Sci., 2004, 25(2):105-111.
Gurevich et al., "Visual arrestin interaction with rhodopsin," J Biol Chem, 1993, 268(16):11628-11638.
Gurevich et al., "Agonist-receptor-arrestin, an alternative ternary complex with high agonist affinity," J Biol Chem, 1997, 272(46):28849-28852.

Haas et al., "Short-term tocolytics for preterm delivery—current perspectives," International Journal of Women's Health, 2014, 6:343-349.
Haney et al., "Overcoming beta-agonist tolerance: high dose salbutamol and ipratropium bromide. Two randomised controlled trials," Respiratory Research, 2007, 8:19, 7 pages.
Hanson et al., "Differential interaction of spin-labeled arrestin with inactive and active phosphorhodopsin," Proc Natl Acad Sci USA, 2006, 103(13):4900-4905.
Hirakawa et al., "$Ca^{2+}$-independent sortase-A exhibits high selective protein ligation activity in the cytoplasm of Escherichia coli," Biotechnol. J., 2015, 10(9):1487-1492.
Huang et al., "Structural insights into μ-opioid receptor activation," Nature, 2015, 524(7565):315-321.
Irannejad et al., "Conformational biosensors reveal GPCR signalling from endosomes," Nature, 2013, 495(7442):534-538.
de Jong et al., "Receptor-ligand binding assays: technologies and applications," Journal of Chromatography B, 2005, 829(1-2):1-25.
Kim et al., "Functional antagonism of different G protein-coupled receptor kinases for β-arrestin-mediated angiotensin II receptor signaling," Proc Natl Acad Sci USA, 2005, 102(5):1442-1447.
Kobilka, "Amino and carboxyl terminal modifications to facilitate the production and purification of a G protein-coupled receptor," Anal Biochem, 1995, 231(1):269-271.
Kobilka, "Structural insights into adrenergic receptor function and pharmacology," Trends Pharmacol Sci, 2011, 32(4):213-218.
Kolakowski, "GCRDb: a G-protein-coupled receptor database," Receptors & Channels, 1994, 2(1):1-7.
Kostenis, "G Proteins in Drug Screening: From Analysis of Receptor-G Protein Specificity to Manipulation of GPCR-Mediated Signalling Pathways," Curr. Pharm. Design., 2006, 12(14):1703-1715.
Kroeze et al., "G-protein-coupled receptors at a glance," J. Cell Sci., 2003, 116(24):4867-4869.
Kruger et al., "Analysis of the substrate specificity of the Staphylococcus aureus sortase transpeptidase SrtA," Biochemistry, 2004, 43:1541-1551.
Kruse et al., "Activation and allosteric modulation of a muscarinic acetylcholine receptor," Nature, 2013, 504(7478):101-106.
Kumari et al., "Functional competence of a partially engaged GPCR-β-arrestin complex," Nat Commun, 2016, 7:13416, 16 pages.
Lagerström et al., "Structural diversity of G protein-coupled receptors and significance for drug discovery," Nat Rev Drug Discov, 2008, 7(4):339-357.
Langmead et al., "Functional and structural perspectives on allosteric modulation of GPCRs," Curr Opin Cell Biol, 2014, 27:94-101.
Laporte et al., "The $\beta_2$-adrenergic receptor/Barrestin complex recruits the clathrin adaptor AP-2 during endocytosis," Proc Natl Acad Sci USA, 1999, 96(7):3712-3717.
Lefkowitz et al., "New roles for β-arrestins in cell signaling: not just for seven-transmembrane receptors," Mol. Cell, 2006, 24(5):643-652.
Lefkowitz et al., "Transduction of Receptor Signals by β-Arrestins," Science, 2005, 308(5721):512-517.
Lefkowitz, "A brief history of G-protein coupled receptors (Nobel Lecture)," Angew Chem Int Ed Engl, 2013, 52(25):6366-6378.
Lefkowitz, "Seven transmembrane receptors: something old, something new," Acta Physiol, 2007, 190(1):9-19.
Liu et al., "Mechanism of intracellular allosteric $\beta_2$AR antagonist revealed by X-ray crystal structure," Nature, 2017, 548(7668):480-484.
Manglik et al., "Structural basis for G protein-coupled receptor activation," Biochemistry, 2017, 56(42):5628-5634.
Manglik et al., "Crystal structure of the μ-opioid receptor bound to a morphinan antagonist," Nature, 2012, 485(7398):321-326.
Mannocci et al., "20 years of DNA-encoded chemical libraries," Chem Commun (Camb), 2011, 47(48):12747-12753.
Matsumoto et al., "Site-specific protein labeling with amine-containing molecules using Lactobacillus plantarum sortase," Biotechnol. J., 2012, 7(5):642-648.
McCutcheon's vol. 1, Emulsifiers & Detergents, 1994, North American Edition, pp. 236-239.

(56) References Cited

OTHER PUBLICATIONS

Menzella et al., "The clinical profile of benralizumab in the management of severe eosinophilic asthma," Ther Adv Respir Dis, 2016, 10(6):534-548.
Moore et al., "Regulation of receptor trafficking by GRKs and arrestins," Annu Rev Physiol, 2007, 69:451-482.
Muir et al., "Expressed protein ligation: A general method for protein engineering," Proc Natl Acad Sci USA, 1998, 95(12):6705-6710.
Busse et al., "Expert Panel Report 3 (EPR-3): Guidelines for the Diagnosis and Management of Asthma-Summary Report 2007," J Allergy Clin Immunol, 2007, 120(5 Suppl):S94-138.
Neves et al., "G protein pathways," Science, 2002, 296(5573): 4 pages.
Nobles et al., "Distinct phosphorylation sites on the $\beta_2$-adrenergic receptor establish a barcode that encodes differential functions of $\beta$-arrestin," Sci Signal, 2011, 4(185):ra51, 22 pages.
Nobles et al., "The active conformation of $\beta$-arrestin1," J Biol Chem, 2007, 282(29):21370-21381.
Overington et al., "How many drug targets are there?," Nat. Rev. Drug Disc., 2006, 5(12):993-996.
Palczewski et al., "Role of the carboxyl-terminal region of arrestin in binding to phosphorylated rhodopsin," J. Biol. Chem., 1991, 266:15334-15339.
Peterson et al., "The diverse roles of arrestin scaffolds in G protein-coupled receptor signaling," Pharmacol Rev, 2017, 69(3):256-297.
Pierce et al., "Seven-transmembrane receptors," Nat Rev Mol Cell Biol, 2002, 3(9):639-650.
Piotukh et al., "Directed evolution of sortase A mutants with altered substrate selectivity profiles," J Am Chem Soc, 2011, 133(44):17536-17539.
Rajagopal et al., "GPCR desensitization: Acute and prolonged phases," Cell Signal, 2018, 41:9-16.
Rajagopal, "Quantifying biased agonism: understanding the links between affinity and efficacy," Nat Rev Drug Discov, 2013, 12(6): 2 pages.
Rankovic et al., "Biased agonism: An emerging paradigm in GPCR drug discovery," Bioorg Med Chem Lett, 2016, 26(2):241-250.
Rashidian et al., "Use of $^{18}$F-2-Fluorodeoxyglucose to Label Antibody Fragments for Immuno-Positron Emission Tomography of Pancreatic Cancer," ACS Cent. Sci., 2015, 1:142-147.
Rask-Andersen et al., "Trends in the exploitation of novel drug targets," Nat. Rev. Drug Disc., 2011, 10(8):579-590.
Rasmussen et al., "Crystal structure of the $\beta 2$ adrenergic receptor-Gs protein complex," Nature, 2011, 477:549-555.
Rasmussen et al., "Structure of a nanobody-stabilized active state of the $\beta_2$ adrenoceptor," Nature, 2011, 469(7329):175-180.
Reeves et al., "Structure and function in rhodopsin: A tetracycline-inducible system in stable mammalian cell lines for high-level expression of opsin mutants," Proc Natl Acad Sci USA, 2002, 99(21):13413-13418.
Reiter et al., "Molecular mechanism of $\beta$-arrestin-biased agonism at seven-transmembrane receptors," Annu Rev Pharmacol Toxicol, 2012, 52:179-197.
Reiter et al., "GRKs and $\beta$-arrestins: roles in receptor silencing, trafficking and signaling," Trends Endocrinol Metab, 2006, 17(4):159-165.
Remington's Pharmaceutical Sciences, 15th Ed. 1975, pp. 335-337.
Rosenbaum et al., "The structure and function of G-protein-coupled receptors," Nature, 2009, 459(7245):356-363.
Samantaray et al., "Peptide-sugar ligation catalyzed by transpeptidase sortase: A facile approach to neoglycoconjugate synthesis," J Am Chem Soc, 2008, 130(7):2132-2133.
Schmidt et al., "Enzyme-mediated ligation technologies for peptides and proteins," Current Opinion in Chemical Biology, 2017, 38:1-7.
Serebryany et al., "Artificial membrane-like environments for in vitro studies of purified G-protein coupled receptors," Biochimica et Biohphysica Acta, 2012, 1818(2):225-233.
Shen et al., "Reconstitution of Membrane Proteins into Model Membranes: Seeking Better Ways to Retain Protein Activities," Int. J. Mol. Sci., 2013, 14(1):1589-1607.
Shenoy et al., "Multifaceted roles of $\beta$-arrestins in the regulation of seven-membrane-spanning receptor trafficking and signalling," Biochem. J., 2003, 375(Pt 3):503-515.
Shenoy et al., "$\beta$-Arrestin-mediated receptor trafficking and signal transduction," Trends Pharmacol Sci, 2011, 32(9):521-533.
Shukla et al., "Structure of active beta-arrestin-1 bound to a G-protein-coupled receptor phosphopeptide," Nature, 2013, 497(7447):137-141.
Shukla et al., "Emerging paradigms of $\beta$-arrestin-dependent seven transmembrane receptor signaling," Trends Biochem Sci, 2011, 36(9):457-469.
Smith et al., "The beta-arrestins: Multifunctional regulators of G protein-coupled receptors," J Biol Chem, 2016, 291(17):8969-8977.
Sommer et al., "Dynamics of arrestin-rhodopsin interactions: Loop movement is involved in arrestin activation and receptor binding," J Biol Chem, 2007, 282(35):25560-25568.
Staus et al., "Allosteric nanobodies reveal the dynamic range and diverse mechanisms of G-protein-coupled receptor activation," Nature, 2016, 535(7612):448-452.
Thanawala et al., "Ligand bias prevents class equality among beta-blockers," Curr Opin Pharmacol, 2014, 16, 50-57.
Thomsen et al., "GPCR-G Protein-$\beta$-Arrestin Super-Complex Mediates Sustained G Protein Signaling," Cell, 2016, 166(4):907-919.
Tomiyama et al., "Beta-Blockers in the Management of Hypertension and/or Chronic Kidney Disease," Int J Hypertens, 2014, 2014:919256, 7 pages.
Violin et al., "$\beta$-arrestin-biased ligands at seven-transmembrane receptors," Trends Pharmacol. Sci., 2007, 28(8):416-422.
Vishnivetskiy et al., "An additional phosphate-binding element in arrestin molecule," J. Biol. Chem., 2000, 275(52):41049-41057.
Weberpals et al., "Beta blockers and cancer prognosis—The role of immortal time bias: A systematic review and meta-analysis," Cancer Treat Rev, 2016, 47:1-11.
Wehbi et al., "Noncanonical GPCR signaling arising from a PTH receptor-arrestin-G$\beta\gamma$ complex," Proc Natl Acad Sci USA, 2013, 110(4):1530-1535.
Whalen et al., "Therapeutic potential of $\beta$-arrestin- and G protein-biased agonists," Trends Mol Med, 2011, 17(3):126-139.
Whorton et al., "A monomeric G protein-coupled receptor isolated in a high-density lipoprotein particle efficiently activates its G protein," Proc Natl Acad Sci USA, 2007, 104(18):7682-7687.
Wikipedia, "Beta$_2$-adrenergic agonist," <https:en.wikipedia.org/wiki/Beta2-adrenergic_agonist> webpage accessed on Dec. 20, 2017.
Witte et al., "Site-specific protein modification using immobilized sortase in batch and continuous-flow systems," Nat. Protoc, 2015, 10(3):508-516.
Witte et al., "Enzymatic glycoprotein synthesis: Preparation of ribonuclease glycoforms via enzymatic glycopeptide condensation and glycosylation," J Am Chem Soc, 1997, 119(9):2114-2118.
Wootten et al., "Emerging paradigms in GPCR allostery: implications for drug discovery," Nat Rev Drug Discov, 2013, 12(8):630-644.
Wuethrich et al., "Site-Specific Chemoenzymatic Labeling of Aerolysin Enables the Identification of New Aerolysin Receptors," PLoS ONE, 2014, 9(10):e109883, 11 pages.
Xiao et al., "Activation-dependent Conformational Changes in $\beta$-Arrestin 2," J. Biol. Chem., 2004, 279(53):55744-55753.
Yao et al., "The effect of ligand efficacy on the formation and stability of a GPCR-G protein complex," Proc Natl Acad Sci USA, 2009, 106(23):9501-9506.
Zindel et al., "Identification of key phosphorylation sites in PTH1R that determine arrestin3 binding and fine-tune receptor signaling," Biochem J, 2016, 473(22):4173-4192.
Zou et al., "N-terminal T4 lysozyme fusion facilitates crystallization of a G protein coupled receptor," PLoS One, 2012, 7(10):e46039, 9 pages.
European Patent Office Extended Search Report for Application No. 19750445.9 dated Nov. 8, 2021 (8 pages).
Staus et al., "Sortase ligation enables homogeneous GPCR phosphorylation to reveal diversity in [beta]-arrestin coupling,"

(56) References Cited

OTHER PUBLICATIONS

Proceedings of the National Academy of Sciences, vol. 115, No. 15, Mar. 26, 2018 (Mar. 26, 2018), pp. 3834-3839.
Shukla et al., "Visualization of arrestin recruitment by a G-protein-coupled receptor," Nature, vol. 512, No. 7513, Jun. 22, 2014 (Jun. 22, 2014), pp. 218-222.
International Search Report and Written Opinion for Application No. PCT/US2019/016999 dated Jun. 21, 2019. (17 pages).

A.

B.

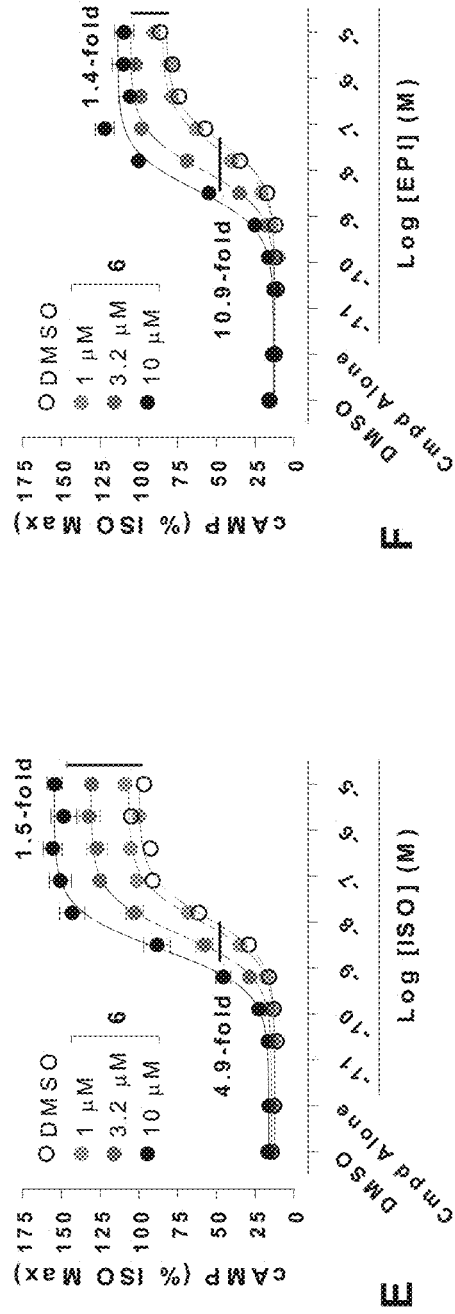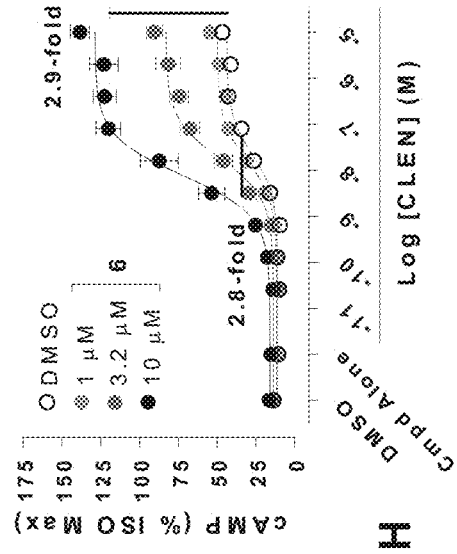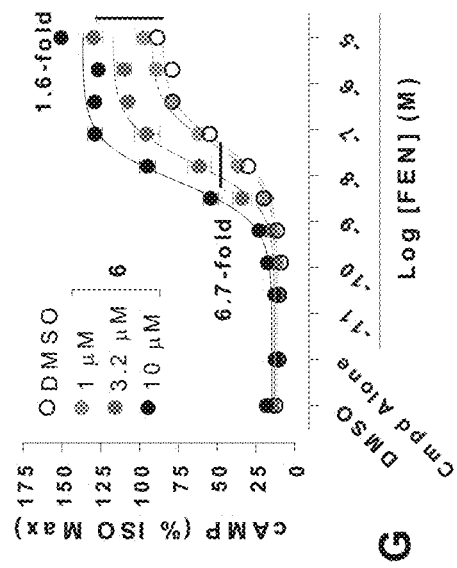
FIGs. 22E-22H

| Cmpds | R¹ | –NR⁴R⁵ | ³H-Fenoterol High Affinity Binding | | | | Cell-Based Assays | | | | | |
|---|---|---|---|---|---|---|---|---|---|---|---|---|
| | | | β2AR-membrane | | Phosphorylated β2V2R | | G Protein cAMP Accumulation | | | β-arrestin Recruitment | | |
| | | | No Transducer (%) | + Gs (%) | No Transducer (%) | + βarr-1 (%) | E-max (%) | EC₅₀ Shift (Fold) | | E-max (%) | EC₅₀ Shift (Fold) | |
| DMSO | | | 100 | 100 | 100 | 100 | 100 | 1.0 | | 100.0 | 1.0 | |
| Cmpd-6 | | | 845.9 ±64.5 | 159.3 ±14.9 | 960.6 ±72.7 | 284.9 ±21.3 | 136.7 ±9.0 | 5.2 ±0.4 | | 168.7 ±5.3 | 5.1 ±0.4 | |
| A3 | | | 163.5 ±26.3 | 93.9 ±6.6 | 111.6 ±9.9 | 100.4 ±6.2 | 79.0 ±12.8 | 0.9 ±0.2 | | 58.6 ±1.5 | 0.9 ±0.1 | |
| A4 | | | 207.7 ±31.5 | 81.6 ±8.1 | 194.9 ±21.4 | 138.5 ±16.0 | 115.5 ±2.8 | 1.2 ±0.2 | | 91.0 ±3.4 | 1.1 ±0.1 | |
| A5 | | | 370.0 ±53.2 | 102.8 ±3.5 | 242.9 ±24.9 | 153.8 ±11.1 | 102.4 ±8.2 | 1.9 ±0.3 | | 238.3 ±4.1 | 3.2 ±0.3 | |
| A6 | | | 144.8 ±10.1 | 82.5 ±4.6 | 123.1 ±11.8 | 104.2 ±11.1 | 108.7 ±1.1 | 1.0 ±0.2 | | 103.7 ±4.4 | 0.8 ±0.2 | |
| A7 | | | 249.3 ±42.7 | 103.8 ±12.6 | 207.0 ±19.2 | 129.7 ±10.4 | 76.6 ±4.1 | 1.8 ±0.3 | | 207.4 ±3.8 | 2.7 ±0.2 | |

FIG. 23

SEQUENCE LISTING

```
<160> NUMBER OF SEQ ID NOS: 16

<210> SEQ ID NO 1
<211> LENGTH: 7
<212> TYPE: PRT
<213> ORGANISM: Artificial sequence
<220> FEATURE:
<223> OTHER INFORMATION: Synthetic

<400> SEQUENCE: 1

Leu Pro Glu Thr Gly Gly Gly
1               5

<210> SEQ ID NO 2
<211> LENGTH: 29
<212> TYPE: PRT
<213> ORGANISM: Artificial sequence
<220> FEATURE:
<223> OTHER INFORMATION: Synthetic

<400> SEQUENCE: 2

Ala Arg Gly Arg Thr Pro Pro Ser Leu Gly Pro Gln Asp Glu Ser Cys
1               5                   10                  15

Thr Thr Ala Ser Ser Ser Leu Ala Lys Asp Thr Ser Ser
            20                  25
```

```
<210> SEQ ID NO 3
<211> LENGTH: 7
<212> TYPE: PRT
<213> ORGANISM: Artificial sequence
<220> FEATURE:
<223> OTHER INFORMATION: Synthetic

<400> SEQUENCE: 3

Leu Pro Glu Thr Gly Gly His
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Leu Pro Xaa Thr Gly
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Leu Pro Xaa Thr Ala
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic

<400> SEQUENCE: 6

Leu Ala Ala Thr Gly Trp Met
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic

<400> SEQUENCE: 7

Leu Pro Lys Thr Gly Asp Asp
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic
```

```
<400> SEQUENCE: 8

Leu Pro Gln Thr Ser Glu Gln
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic

<400> SEQUENCE: 9

Ile Pro Lys Thr Gly
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Met Pro Xaa Thr Gly
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic

<400> SEQUENCE: 11

Leu Ala Glu Thr Gly
1               5

<210> SEQ ID NO 12
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Leu Pro Xaa Ala Gly
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic

<400> SEQUENCE: 13

Leu Pro Glu Ser Gly
1               5
```

```
<210> SEQ ID NO 14
<211> LENGTH: 5
<212> TYPE: PRT
<213> ORGANISM: Artificial sequence
<220> FEATURE:
<223> OTHER INFORMATION: Synthetic

<400> SEQUENCE: 14

Leu Pro Glu Leu Gly
1               5

<210> SEQ ID NO 15
<211> LENGTH: 5
<212> TYPE: PRT
<213> ORGANISM: Artificial sequence
<220> FEATURE:
<223> OTHER INFORMATION: Synthetic

<400> SEQUENCE: 15

Leu Pro Glu Val Gly
1               5

<210> SEQ ID NO 16
<211> LENGTH: 32
<212> TYPE: PRT
<213> ORGANISM: Artificial sequence
<220> FEATURE:
<223> OTHER INFORMATION: Synthetic

<400> SEQUENCE: 16

Gly Gly Gly Ala Arg Gly Arg Thr Pro Pro Ser Leu Gly Pro Gln Asp
1               5                   10                  15

Glu Ser Cys Thr Thr Ala Ser Ser Ser Leu Ala Lys Asp Thr Ser Ser
            20                  25                  30
```

SYSTEM AND METHOD FOR HOMOGENOUS GPCR PHOSPHORYLATION AND IDENTIFICATION OF BETA-2 ADRENERGIC RECEPTOR POSITIVE ALLOSTERIC MODULATORS

RELATED APPLICATIONS

This application claims priority to U.S. provisional application No. 62/627,678, filed Feb. 7, 2018, and U.S. provisional application No. 62/627,680, filed Feb. 7, 2018, the entire contents of which are incorporated herein by reference.

TECHNICAL FIELD

The invention relates to a chimeric G protein-coupled receptor (GPCR) comprising a C-terminus amino acid sequence ligated to a synthetic phosphopeptide, $β_2$ adrenergic receptor positive allosteric modulators, their use in the treatment of diseases or conditions ameliorated by $β_2$ receptor activation, and methods of screening and identifying $β_2$ adrenergic receptor positive allosteric modulators.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,600 Bytes ASCII (Text) file named "028193-9284-US01_As_Filed_Sequence_Listing.TXT," created on Feb. 6, 2018.

BACKGROUND OF THE INVENTION

G protein-coupled receptors (GPCRs), a large family of plasma membrane receptors coupled to guanine nucleotide regulatory proteins, represent one of the most important mechanisms for transducing extracellular signals into specific cellular responses. Their important role in regulating many physiological processes makes them a common therapeutic target of clinically used drugs. The overwhelming majority of these, both agonists and antagonists, bind to the orthosteric binding site on the receptor. This is defined as the site to which the endogenous ligand(s) for the receptor binds, e.g. adrenaline for the adrenergic receptors, histamine for the histamine receptors etc. Most clinically used antagonists are orthosteric binders and exert their effects by competitive inhibition.

Despite their ability to recognize a vast array of ligands (Lagerstrom M C & Schioth H B (2008) *Nat Rev Drug Discov* 7(4):339-357), GPCRs have a highly conserved mechanism of action. Ligand binding to the extracellular orthosteric pocket induces conformational changes within the receptor transmembrane (TM) region (Manglik A & Kruse A C (2017) *Biochemistry* 56(42):5628-5634), leading to the sequential intracellular coupling of three main transducer proteins: G protein, GPCR kinase (GRK) and β-arrestin (βarr) (Lefkowitz R J (2013) *Angew Chem Int Ed Engl* 52(25):6366-6378). More specifically, GPCR-dependent activation of the heterotrimeric G protein leads to the dissociation of the a subunit from the fly subunits, resulting in modulation of second messenger systems, such as cAMP (Neves S R, et al. (2002) *Science* 296(5573):1636-1639). Subsequent GRK phosphorylation of specific serine/threonine residues within the receptor third intracellular loop (ICL) or carboxyl (C)-terminal tail recruits βarr (Benovic J L, et al. (1987) *Proc Natl Acad Sci USA* 84(24):8879-8882). The binding of βarr desensitizes GPCR signaling by sterically blocking G protein coupling and promoting receptor internalization through interactions with AP2 and clathrin (Shenoy S K & Lefkowitz R J (2011) *Trends Pharmacol Sci* 32(9):521-533). Additionally, βarr can directly modulate cell signaling through G protein-independent pathways (Peterson Y K & Luttrell L M (2017) *Pharmacol Rev* 69(3): 256-297).

It is now well established that "biased" GPCR ligands can disproportionately regulate particular branches of receptor signaling, a phenomenon known as biased agonism (Reiter E, et al. (2012) *Annu Rev Pharmacol Toxicol* 52:179-197). The selective activation of signaling pathways indicates that, although all three transducers specifically interact with agonist-bound GPCRs, their conformational specificities are not identical. However, the fundamental mechanisms underlying this differential coupling remain obscure, largely because events mediated by different transducers are intricately intertwined. In particular, βarr binds to receptors through a two-step process, initially interacting with GRK-phosphorylated residues and then coupling to the agonist-activated GPCR TM core (FIG. 1) (Gurevich V V & Benovic J L (1993) *J Biol Chem* 268(16):11628-11638). Biochemical and structural studies have demonstrated that binding to GPCRs' phosphorylated tails induces extensive conformational changes in βarr, including the extension of several loops implicated in βarr's interaction with GPCRs' TM bundle (Shukla A K, et al. (2013) *Nature* 497(7447):137-141).

Engagement of βarr with GPCRs' TM cores is believed to mediate particular functions of βarr such as receptor desensitization, but efforts to understand the nature and consequences of this interaction have been hampered by its low affinity and its dependence on GRK phosphorylation. Thus, there remains a need for compositions and methods for obtaining uniformly phosphorylated receptors in a cellular context or in vitro, which can be used to identify compounds which modulate GPCR activity. Such compounds may have therapeutic utility against diseases associated with GPCR dysfunction.

Recently, an increasing number of negative and positive allosteric modulators (NAMs and PAMs) for GPCRs have been described, although to date only two have reached the clinic. Rather than directly stimulating or inhibiting biological effects on their own, these allosteric compounds exert their effects by modulating receptor responsiveness to endogenous agonists. Such allosteric ligands offer a number of potential advantages as drugs including greater specificity amongst closely related receptor subtypes, and maximum or ceiling effects which can reduce adverse actions, amongst others. Such allosteric modulators can also serve as valuable reagents in the research laboratory where, by virtue of their cooperative interactions with orthosteric ligands, they can help to freeze or lock specific receptor conformations so that they can be studied by biophysical techniques.

The $β_2$-adrenergic receptor ($β_2$AR) is a prototypical G protein-coupled receptor (GPCR) that plays important roles in cardiovascular and pulmonary pathophysiologies, and is a key therapeutic target. Conventional drug discovery efforts at $β_2$ARs have led to the development of ligands that bind exclusively to the receptor's hormone-binding orthosteric site. On the other hand, targeting the largely unexplored and evolutionarily unique allosteric sites has the potential for developing drugs that are more specific and have fewer side-effects than orthosteric ligands.

Selection of allosteric modulators for GPCRs using the usual cell-based functional assays such as those for cyclic AMP (cAMP) generation or β-arrestin recruitment have a number of disadvantages. For example, it can be laborious and difficult to interpret modulation of a response with these assays, rather than the on or off responses that such assays are better suited to measure. These assays are also subject to a variety of artifacts and have relatively limited compound throughput of ~$10^3$-$10^6$.

In contrast, interaction or affinity-based methods, in which large libraries of self-encoding potential binders are screened against a target protein molecule, circumvent these shortcomings. A particularly powerful approach is the use of DNA encoded small molecule libraries (DELs) containing as many as 1 billion potential ligands. Each molecule in such a library is covalently linked to a small stretch of nucleotides which serves as a barcode which is used to identify target binders by next generation sequencing. Such approaches work well when applied to soluble protein targets but have been much more difficult to adapt to membrane proteins such as GPCRs. However, using this approach we recently described isolation of the first NAM for the β2-adrenergic receptor ("allosteric β-blocker") and identified its intracellular binding site on the receptor by x-ray crystallography (Ahn et al. (2017) PNAS 114(7):1708-1713. doi: 10.1073/pnas.1620645114; Liu et al. (2017) Nature 548(7668):480-484. doi: 10.1038/nature23652.).

SUMMARY OF THE INVENTION

In one aspect, the disclosure provides a complex comprising (i) a chimeric G protein-coupled receptor (GPCR) comprising the amino acid sequence LPETGGG (SEQ ID NO: 1) located within the C-terminus of the GPCR and a synthetic phosphopeptide ligated to SEQ ID NO: 1; and (ii) a β-arrestin (βarr) protein bound to the C-terminus of the GPCR.

In another aspect, the disclosure provides an in vitro method for producing the aforementioned complex, as well as methods for identifying compounds or ligands which bind to and modulate the activity of the complex.

The present invention also relates to positive allosteric small molecules for the β$_2$AR, identified by affinity-based screening of over 500 million distinct library compounds. Compounds of the invention display positive cooperativity with orthosteric agonists, thus enhancing their binding to the receptor and ability to stabilize its active state. The compounds also exhibit positive cooperativity with G protein and β-arrestin, thus potentiating their stabilization of high-affinity agonist-bound states of the receptor, as well as downstream cAMP production and β-arrestin recruitment to the activated receptor. The positive allosteric activity is specific for the β$_2$AR compared to its closely related subtype, the β$_1$AR.

In another aspect, provided is a compound according to Formula (I):

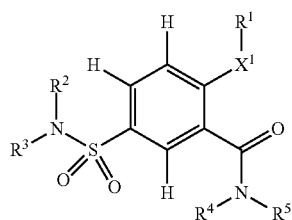

(I)

or a pharmaceutically acceptable salt thereof, wherein:

$R^1$ is an aryl group optionally substituted with 1-5 substituents independently selected from the group consisting of $C_{1-6}$alkyl, $C_{1-6}$ haloalkyl, $C_{3-7}$cycloalkyl, halogen, cyano, —OH, —O$C_{1-6}$alkyl, —O$C_{1-6}$ haloalkyl, —NH$_2$, —NH$C_{1-6}$alkyl, —N($C_{1-6}$alkyl)$_2$, —O$C_{3-6}$cycloalkyl, —NH$C_{3-6}$cycloalkyl, —N($C_{1-6}$alkyl)($C_{3-6}$cycloalkyl), and —N($C_{3-6}$cycloalkyl)$_2$, and optionally the aryl is phenyl wherein two substituents join to form a 5- to 7-membered non-aromatic fused ring containing 1-2 heteroatom groups selected from NR$^{1a}$ and O;

$X^1$ is O, N(H), N($C_{1-4}$alkyl), S, S(O), S(O)$_2$, C(O), or CR$^{1b}$R$^{1c}$;

$R^{1a}$ is H or $C_{1-4}$alkyl;

$R^{1b}$ and $R^{1c}$ are each independently hydrogen or $C_{1-4}$alkyl, or $R^{1b}$ and $R^{1c}$ together with the carbon to which they are attached form a $C_{3-6}$cycloalkyl ring;

$R^2$ is hydrogen, $C_{1-6}$alkyl, or $C_{3-7}$cycloalkyl;

$R^3$ is hydrogen, $C_{1-6}$alkyl, $C_{3-7}$cycloalkyl, or aryl, the aryl being optionally substituted with 1-5 substituents independently selected from the group consisting of $C_{1-6}$alkyl, $C_{1-6}$haloalkyl, $C_{3-7}$cycloalkyl, halogen, cyano, —OH, —O$C_{1-6}$alkyl, —O$C_{1-6}$ haloalkyl, —NH$_2$, —NH$C_{1-6}$alkyl, —N($C_{1-6}$alkyl)$_2$, —O$C_{3-6}$cycloalkyl, —NH$C_{3-6}$cycloalkyl, —N($C_{1-6}$alkyl)($C_{3-6}$cycloalkyl), and —N($C_{3-6}$cycloalkyl)$_2$;

alternatively, $R^2$ and $R^3$ together with the nitrogen to which they are attached form a 4- to 8-membered heterocyclic ring optionally containing one additional heteroatom selected from N, O, and S, and being optionally substituted with 1-4 substituents independently selected from the group consisting of $C_{1-6}$alkyl, $C_{1-6}$ haloalkyl, halogen, cyano, —OH, oxo, —O$C_{1-6}$alkyl, —NH$_2$, —NH$C_{1-6}$alkyl, and —N($C_{1-6}$alkyl)$_2$;

$R^4$ is hydrogen, $C_{1-6}$alkyl, or $C_{3-7}$cycloalkyl;

$R^5$ is —CHR$^{5a}$R$^{5b}$;

alternatively, $R^4$ and $R^5$ together with the nitrogen to which they are attached form a 4- to 8-membered heterocyclic ring optionally containing one additional heteroatom selected from N, O, and S, and being optionally substituted with 1-4 substituents independently selected from the group consisting of $C_{1-6}$alkyl, $C_{1-6}$ haloalkyl, halogen, cyano, —OH, oxo, —O$C_{1-6}$alkyl, —NH$_2$, —NH$C_{1-6}$alkyl, and —N($C_{1-6}$alkyl)$_2$;

$R^{5a}$ is aryl or —$C_{1-3}$alkylene-aryl, wherein each aryl in $R^{5a}$ is optionally substituted with 1-5 substituents independently selected from the group consisting of $C_{1-6}$alkyl, $C_{1-6}$haloalkyl, $C_{3-7}$cycloalkyl, halogen, cyano, —OH, —O$C_{1-6}$alkyl, —O$C_{1-6}$ haloalkyl, —NH$_2$, —NH$C_{1-6}$alkyl, —N($C_{1-6}$alkyl)$_2$, —O$C_{3-6}$cycloalkyl, —NH$C_{3-6}$cycloalkyl, —N($C_{1-6}$alkyl)($C_{3-6}$cycloalkyl), and —N($C_{3-6}$cycloalkyl)$_2$;

$R^{5b}$ is $X^2$ or —$C_{1-3}$alkylene-$X^2$; and $X^2$ is —CN, —C(O)OH, —C(O)O$C_{1-4}$alkyl, —C(O)NH$_2$, —C(O)NH$C_{1-4}$alkyl, —C(O)N($C_{1-4}$alkyl)$_2$, —SO$_2$NH$_2$, —SO$_2$NH$C_{1-4}$alkyl, or —SO$_2$N($C_{1-4}$alkyl)$_2$.

In another aspect, is provided a pharmaceutical composition comprising a compound according to Formula (I) or pharmaceutically acceptable salt thereof, and a pharmaceutically acceptable carrier.

In another aspect is provided a method of treating a disease or condition ameliorated by β$_2$ receptor activation comprising administering to a subject in need thereof a therapeutically effective amount of the compound of formula (I), a pharmaceutically acceptable salt or composition thereof.

In a further aspect, the invention provides kits comprising a compound of formula (I), or a pharmaceutically acceptable salt or composition thereof, and instructions for use.

Other aspects will become apparent by consideration of the detailed description and accompanying drawings.

BRIEF DESCRIPTION OF THE DRAWING(S)

FIG. 1 shows the two-step binding mode of β-arrestin. Ligand (L) binding to the extracellular orthosteric binding pocket leads to conformational changes within the GPCR transmembrane region to influence intracellular transducer binding. The phosphorylation (red circles) of the receptor C terminus by GPCR-kinase (GRK) initiates the recruitment of β-arrestin (βarr). Conformational changes induced in βarr (βarr*) as a result of binding to the phosphorylated C terminus promotes coupling to the GPCR transmembrane core, which allosterically enhances ligand affinity.

FIG. 2A shows non-phosphorylated $β_2AR$ interacts with Gs heterotrimer but not β-arrestin1 Coomassie-stained gel show the co-immunoprecipitation of Gs heterotrimer (Gs) or β-arrestin1 (βarr1) with isoproterenol (ISO)-bound FLAG-$β_2AR$. Loading controls represent 10% of input.

FIG. 2B shows competition binding experiments using radiolabeled $[^{125}I]$-cyanopindolol (CYP). Gs increases ISO affinity for $β_2AR$ HDLs (log $IC_{50}$: $-8.88+/-0.03$) compared to no transducer (log $IC_{50}$: $-6.82+/-0.03$), but βarr1 does not (log $IC_{50}$: $-6.81+/-0.02$). Data shown are the mean of three independent experiments, with error bars representing standard error.

FIG. 2C shows the fluorescence emission spectrum of bimane-labeled $β_2AR$ HDLs rightward shift and decrease in fluorescence upon addition of ISO, indicative of receptor activation. The effects of ISO are enhanced by Gs but not βarr1. Data shown are representative of three independent experiments.

FIG. 3A shows a cartoon schematic of the sortase ligation method. A synthetic phosphopeptide (pp) derived from the vasopressin-2-receptor ($V_2R$) with three N-terminal glycine residues (GGG-$V_2Rpp$) (SEQ ID NO: 16) is ligated onto receptors containing a C-terminal LPETGGH recognition motif. Phosphorylated serine and threonine residue are indicated with arrows.

FIG. 3B shows Coomassie-stained gel showing the co-immunoprecipitation of heterotrimeric Gs and β-arrestin1 (βarr1) with isoproterenol (ISO)-bound, phosphopeptide-ligated FLAG-$β_2AR$ ($β_2ARpp$). Loading controls represent 10% of input.

FIG. 3C shows competition binding experiments using radiolabeled $[^{125}I]$-cyanopindolol (CYP) with HDLs containing $β_2ARpp$. Gs increases the affinity of ISO for $β_2ARpp$ (log $ID_{50}$: $-9.15+/-0.03$) compared to no transducer (log $ID_{50}$: $-6.24+/-0.04$), and βarr1 increases ISO affinity for $β_2ARpp$ HDLs (log $ID_{50}$: $-7.14+/-0.07$). Data shown are the mean of at least three independent experiments, with error bars representing standard error, and stars (*) indicate a log IC50 value significantly different from the control curve (P<0.05, one-way ANOVA).

FIG. 3D shows competition binding experiments using radiolabeled $[^{125}I]$-cyanopindolol (CYP) with HDLs containing $β_2AR$ ligated to a non-phosphorylated version of the $V_2R$ peptide ($β_2ARnp$). Gs increases the affinity of ISO for $β_2ARnp$ HDLs (log $ID_{50}$: $-9.02+/-0.04$) compared to no transducer (log $ID_{50}$: $-6.42+/-0.09$), but βarr1 does not increase ISO affinity for $β_2ARnp$ HDLs (log $ID_{50}$: $-6.49+/-0.04$). Data shown are the mean of at least three independent experiments, with error bars representing standard error, and stars (*) indicate a log IC50 value significantly different from the control curve (P<0.05, one-way ANOVA).

FIG. 3E shows the effects of ISO on the HDL-$β_2ARpp$-bimane fluorescence emission spectrum are enhanced by Gs and βarr1. Data shown are representative of three independent experiments.

FIG. 4A shows the allosteric interaction between phosphorylated $β_2AR$ and β-arrestin1 requires the finger loop of β-arrestin1. In competition radioligand binding with $β_2ARpp$ HDLs, a finger loop deletion mutant of β-arrestin1 (βarr1) (462-77) has minimal effect on isoproterenol (ISO) binding (log IC50s: no transducer, $-6.30+/-0.05$; βarr1, $-7.25+/-0.07$; βarr1 Δ62-77, $-6.48+/-0.03$). Data shown in are the mean of at least three independent experiments, with error bars representing standard error, and stars (*) indicate a log IC50 value significantly different from the control curve (P<0.05, one-way ANOVA).

FIG. 4B shows βarr1Δ62-77 does not intensify the effects of ISO on the fluorescence spectrum of $β_2ARpp$-bimane HDLs. Data shown are representative of three independent experiments.

FIG. 4C shows competition radioligand binding with $β_2ARpp$ HDLs containing a deletion of the third intracellular loop (Δ238-267). Both Gs (log ID50: $-8.85+/-0.03$) and βarr1 (log $ID_{50}$: $-7.63+/-0.06$) retain their ability to increase isoproterenol (ISO) affinity (no transducer, log ID50: $-6.91+/-0.04$). Data shown are the mean of at least three independent experiments, with error bars representing standard error, and stars (*) indicate a log IC50 value significantly different from the control curve (P<0.05, one-way ANOVA).

FIG. 5A shows the allosteric enhancement of agonist binding induced by β-arrestin1 at the M2 receptor. Competition binding experiments with sortase-ligated $M_2Rpp$ HDLs use $[^3H]$—N-Methyl-Scopolamine (NMS) as the tracer. Heterotrimeric Gi (100 nM, log ID50: $-7.51+/-0.06$) and β-arrestin1 (βarr1) (1 µM, log ID50: $-7.06+/-0.08$) increase the affinity of the agonist carbachol to a similar extent (no transducer, log ID50: $-5.31+/-0.09$). Data are the mean of three independent experiments, with error bars representing standard error, and stars (*) indicate a log IC50 value significantly different from the control curve (P<0.05, one-way ANOVA).

FIG. 5B shows the allosteric enhancement of agonist binding induced by β-arrestin1 at the MOR receptor. Competition binding experiments with sortase-ligated MORpp HDLs use $[^3H]$-Naloxone as the tracer. Gi (1 µM, log ID50: $-8.22+/-0.05$) increases the affinity of the agonist DAMGO to a far greater extent than βarr1 (1 µM, log ID50: $-6.02+/-0.05$) (no transducer, log ID50: $-5.71+/-0.06$). Data are the mean of three independent experiments, with error bars representing standard error, and stars (*) indicate a log IC50 value significantly different from the control curve (P<0.05, one-way ANOVA).

FIG. 5C shows a comparison of the difference in agonists' log IC50 values in the presence of their cognate G proteins versus βarr1 for sortase-ligated $β_2ARpp$, $M_2Rpp$, and MORpp HDLs.

FIG. 6A shows the fluorescence spectra of β-arrestin1 (βarr1) labeled with monobromobimane at residue 70 in the finger loop. Activation of HDL-$β_2ARpp$ by the agonist isoproterenol (ISO) increases βarr1-bimane fluorescence, which is blocked by Nb80 binding to the receptor TM core. Data shown are representative of three independent experiments.

FIG. 6B shows a comparison of βarr1-bimane fluorescence by agonist activation of $β_2ARpp$, $M_2Rpp$, and MORpp HDLs. The area under the fluorescence emission spectra were determined and normalized to $M_2$Rpp plus iperoxo (the maximum signal) in each experiment. All three receptors are significantly different from one another (*P<0.05), and $\beta_2$ARpp and $M_2$Rpp are significantly different from their respective antagonist controls (not indicated, P<0.05). Data are the mean of at least three independent experiments, with error bars representing standard error; P values were determined by one-way ANOVA.

FIG. 6C shows an in vitro GTPase assay measuring GTP hydrolysis as a readout of G protein activation. The basal level of GTP hydrolysis induced by G protein is robustly increased by HDL-$\beta_2$ARpp HDLs in the presence of ISO compared to no ligand (NL) (*P<0.05), which is blocked (desensitization) by the addition of Nb80 (no significant difference between NL and ISO+Nb80). Data are the mean of at least three independent experiments, with error bars representing standard error; P values were determined by one-way ANOVA.

FIG. 6D shows inhibition (% desensitization) of G protein activation by βarr1 is strongest at $M_2$Rpp and significantly different from $\beta_2$ARpp and MORpp HDLs (*P<0.05). Data are the mean of at least three independent experiments, with error bars representing standard error; P values were determined by one-way ANOVA.

FIG. 7A shows the generation and purification of phosphopeptide (pp)-ligated $\beta_2$AR ($\beta_2$ARpp). Purified FLAG-$\beta_2$AR in detergent containing the sortase consensus site LPETGHH after amino acid 365 and a C-terminal 6× His tag ($\beta_2$AR-LPETGHH-His6) was modified using sortase-His6 and GGG-$V_2$Rpp. Ligated $\beta_2$ARpp was subsequently purified from unligated receptor ($\beta_2$AR-LPETGGH-His6), sortase-His6, and GGG-$V_2$Rpp by Talon metal affinity resin and size exclusion chromatography, as shown in the schematic.

Figure 8A:
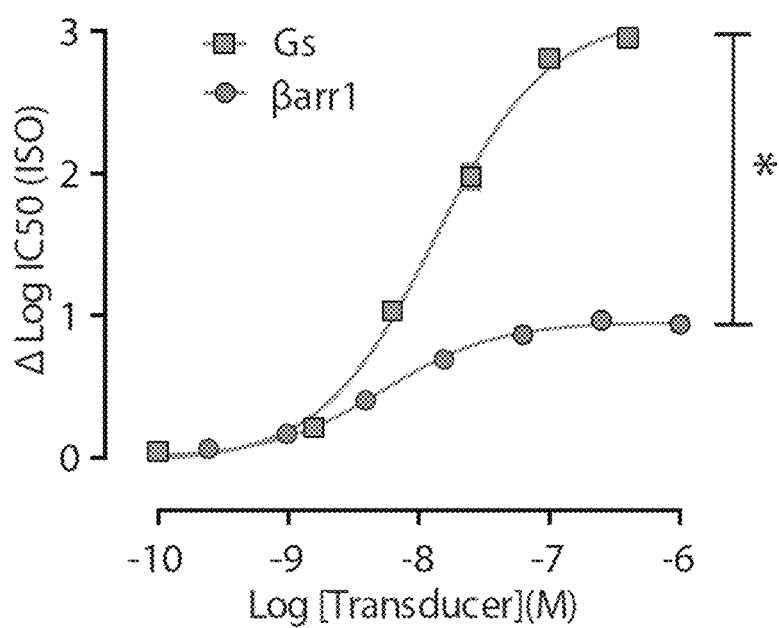

FIG. 8A shows the increase in agonist affinity to the $\beta_2$ARpp induced by β-arrestin1 is 100-fold less than that induced by G protein. Plot of changes in the log IC50 values of isoproterenol (ISO) derived from competition radioligand binding experiments using [$^{125}$I]-cyanopindolol (CYP) and HDL-$\beta_2$ARpp in the absence or indicated concentration of transducer (Gs and β-arrestin1 (βarr1)). The star (*) indicates that curve fit maxima are significantly different (P<0.05, t-test).

Figure 8B:
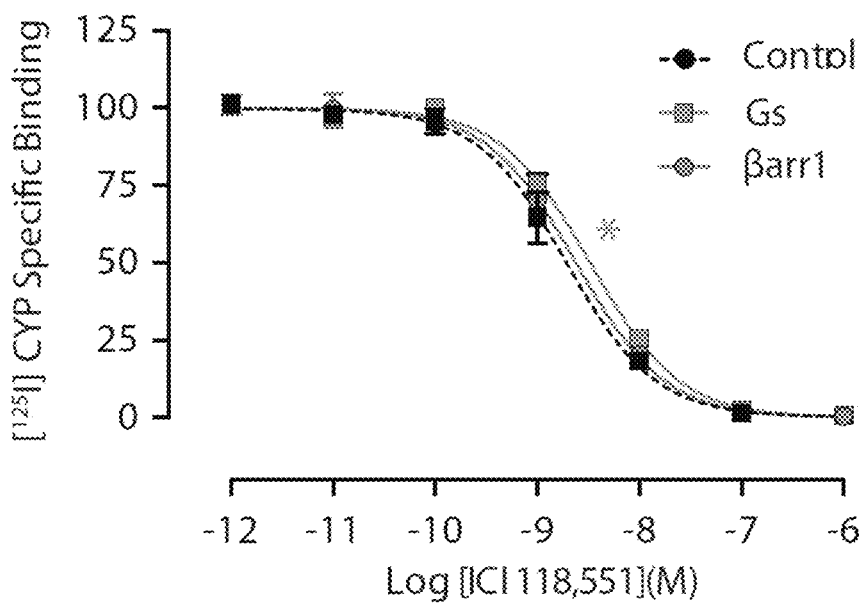

FIG. 8B shows competition binding assays using HDL-$\beta_2$ARpp, [$^{125}$I]—CYP, and the indicated concentration of ICI-118,551 in the presence or absence of Gs (100 nM) or βarr1 (1 μM). Error bars represent standard error from at least three independent experiments. The stars indicate log IC50 values significantly different from the control curves (P<0.05, one-way ANOVA).

Figure 8C:
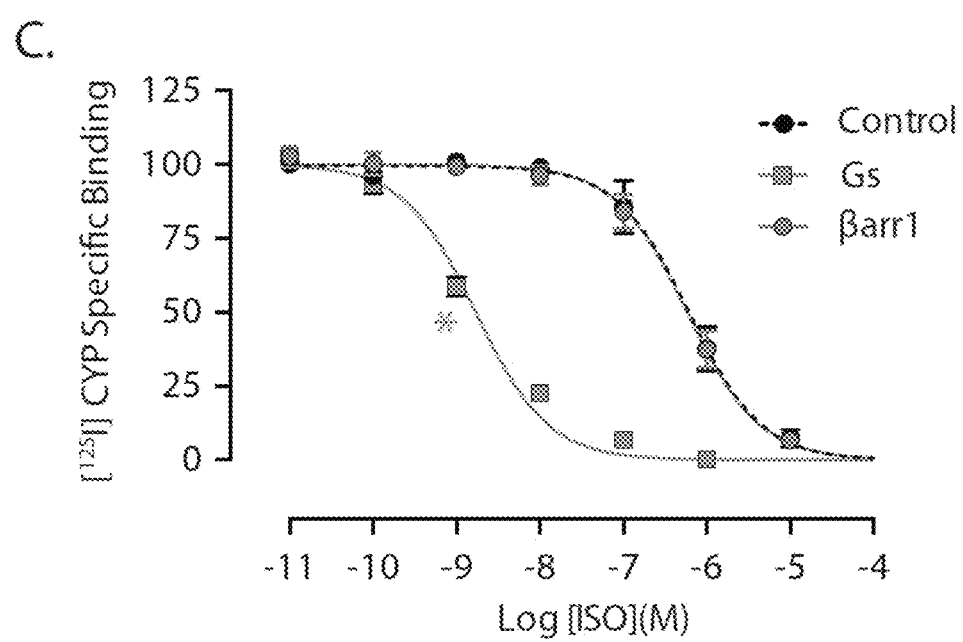

FIG. 8C shows the increase in agonist affinity to the $\beta_2$ARpp induced by β-arrestin1 requires receptor phosphorylation. FIG. 8C shows competition binding assays using HDL-$\beta_2$ARpp, [$^{125}$I]—CYP, and the indicated concentration of ISO where HDL-$\beta_2$ARpp was treated with calf-intestinal alkaline phosphatase (CIP) prior to assay setup. The stars indicate log IC50 values significantly different from the control curves (P<0.05, one-way ANOVA).

Figure 9A:
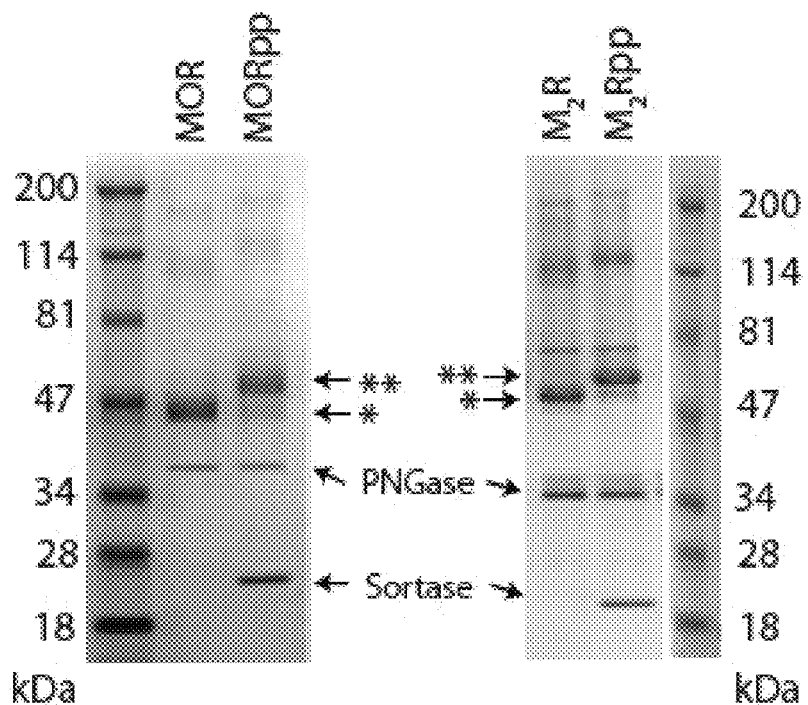

FIG. 9A shows phosphopeptide-ligated (**) MOR (MORpp) and $M_2$R ($M_2$Rpp) were generated by incubating receptors containing a C-terminal sortase recognition site (*) with GGG-$V_2$Rpp and sortase. To determine ligation efficiency, a small fraction of the reaction was deglycosylated with PNGase to visualize changes in receptor molecular weight. Coomassie-stained protein gels are shown.

Figure 5A:
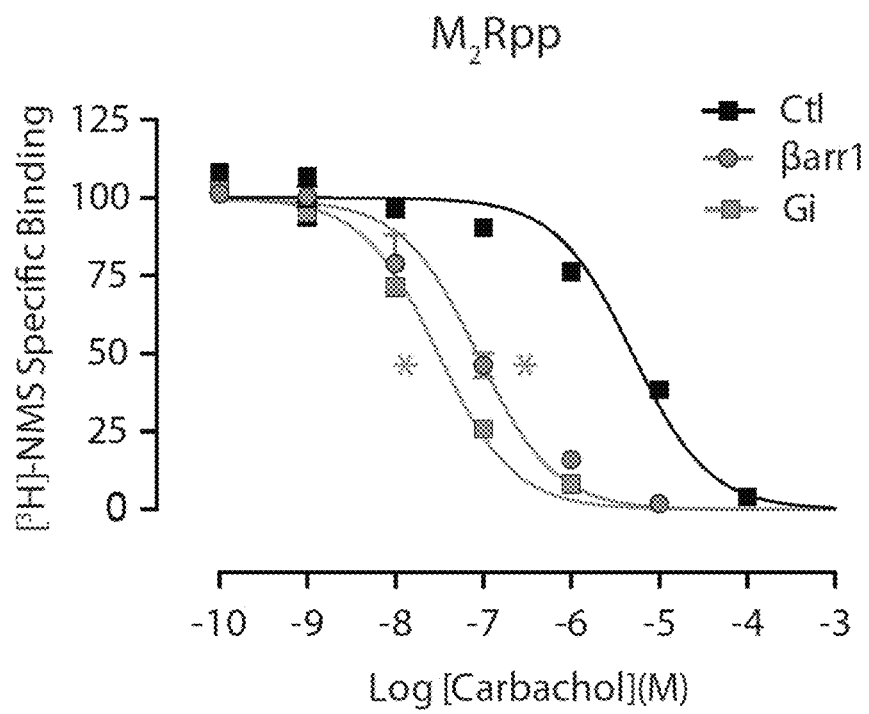
Figure 9B:
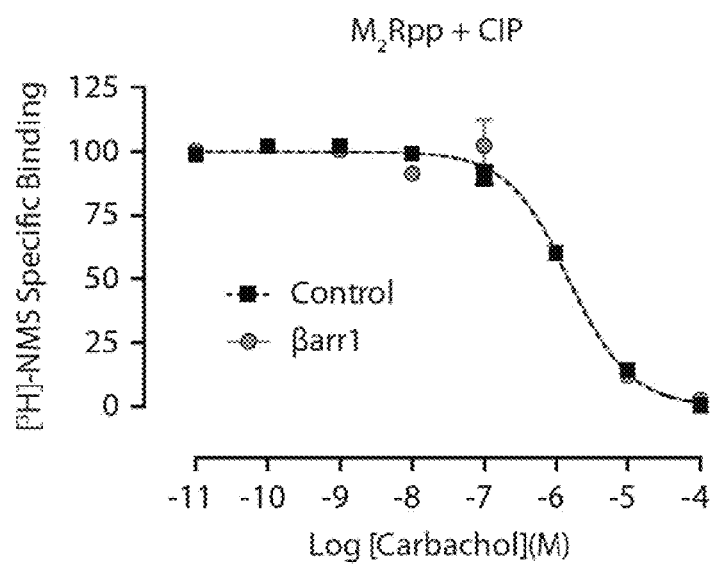

FIG. 9B shows competition binding assays using HDL-$M_2$Rpp performed as in FIG. 5A except that HDLs were treated with calf-intestinal alkaline phosphatase (CIP) prior to assay setup.

Figure 5B:
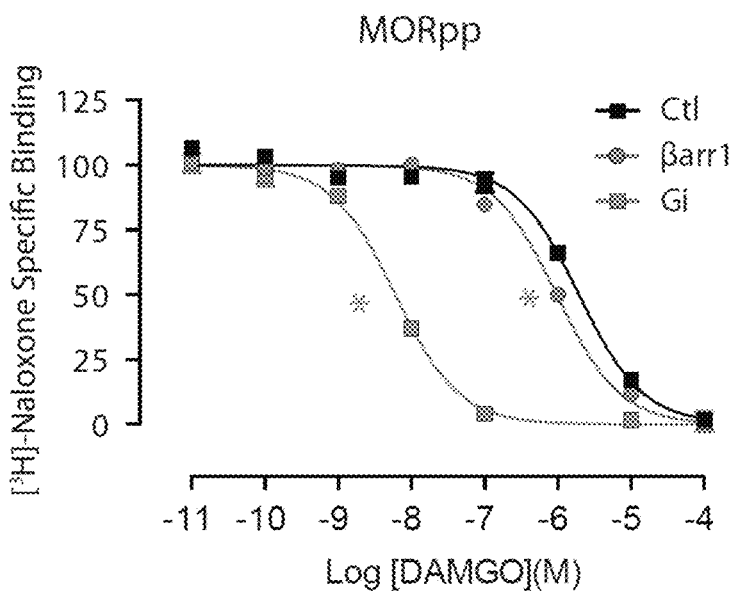
Figure 9C:
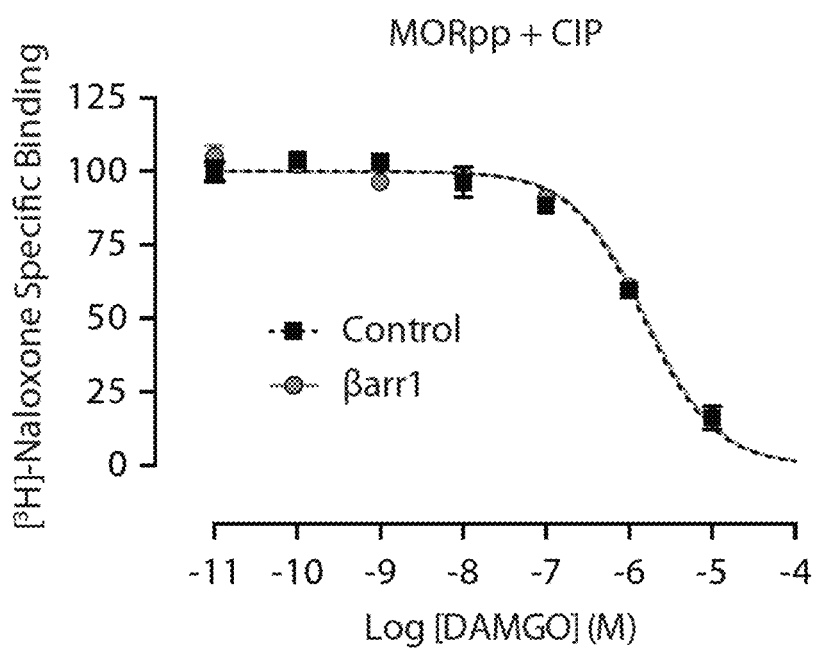

FIG. 9C shows competition binding assays using HDL-MORpp performed as in FIG. 5B except that HDLs were treated with calf-intestinal alkaline phosphatase (CIP) prior to assay setup.

Figure 9D:
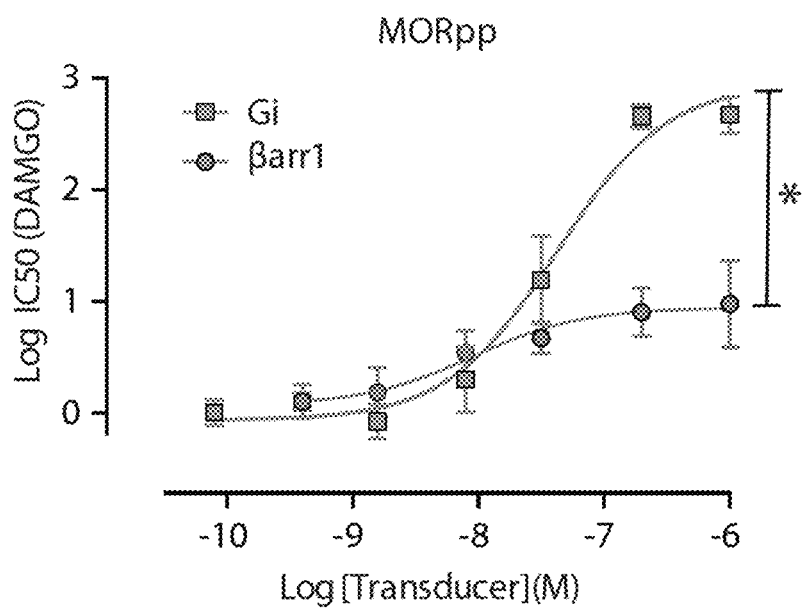

FIG. 9D shows a graph of changes in the log IC50 values for DAMGO determined from competition radioligand binding experiments using [$^3$H]-Naloxone and HDL-MORpp in the absence or indicated concentration of transducer (Gi and β-arrestin1 (βarr1)). Stars (*) indicate that the curve fit maxima are significantly different (P<0.05, t-test).

Figure 9E:
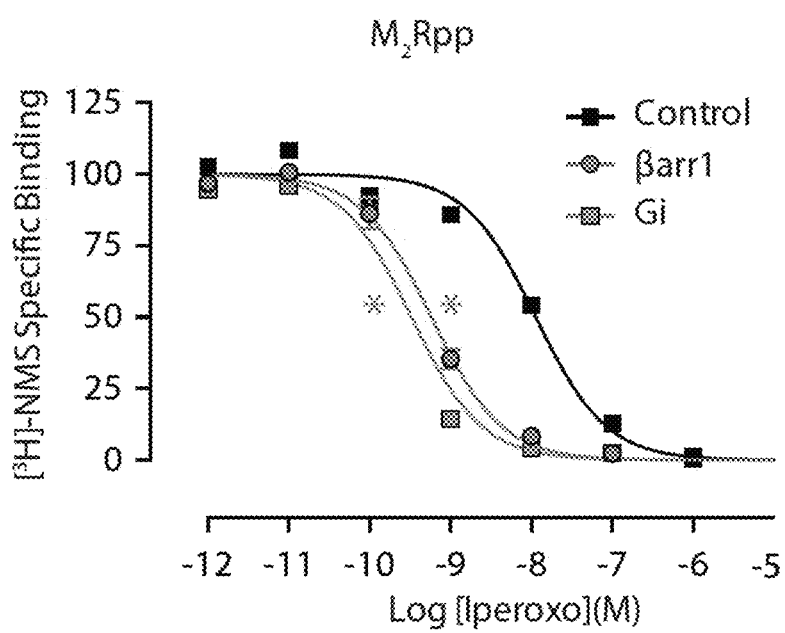

FIG. 9E shows competition binding assays using HDL-$M_2$Rpp performed as in FIG. 5A using iperoxo as the competitor ligand in the presence or absence of Gi (100 nM) or βarr1 (1 μM). Stars (*) indicate log IC50 values significantly different from the control curve (P<0.05, one-way ANOVA).

Figure 9F:
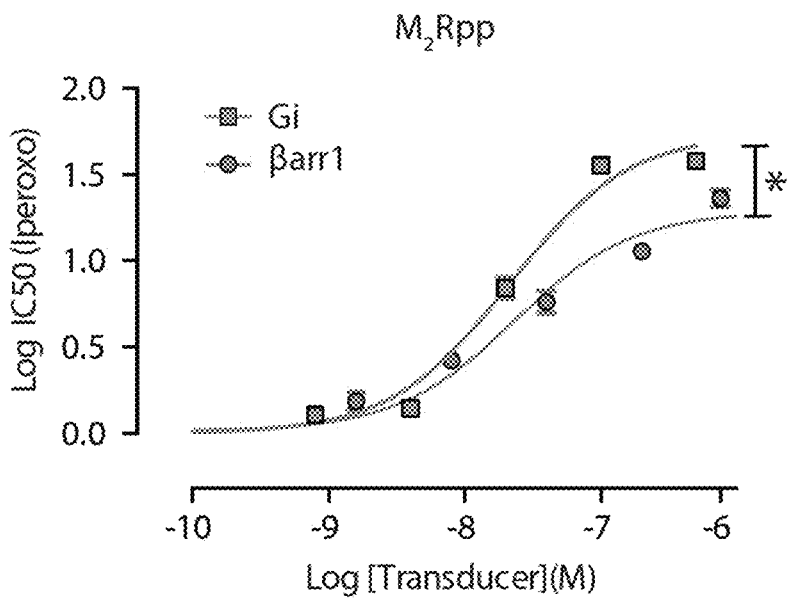

FIG. 9F shows a plot of changes in the log IC50 values of iperoxo obtained from competition binding experiments using [$^3$H]-NMS and HDL-$M_2$Rpp in the absence or indicated concentration of transducer (Gi and βarr1). Stars (*) indicate that the curve fit maxima are significantly different (P<0.05, t-test).

Figure 9G:
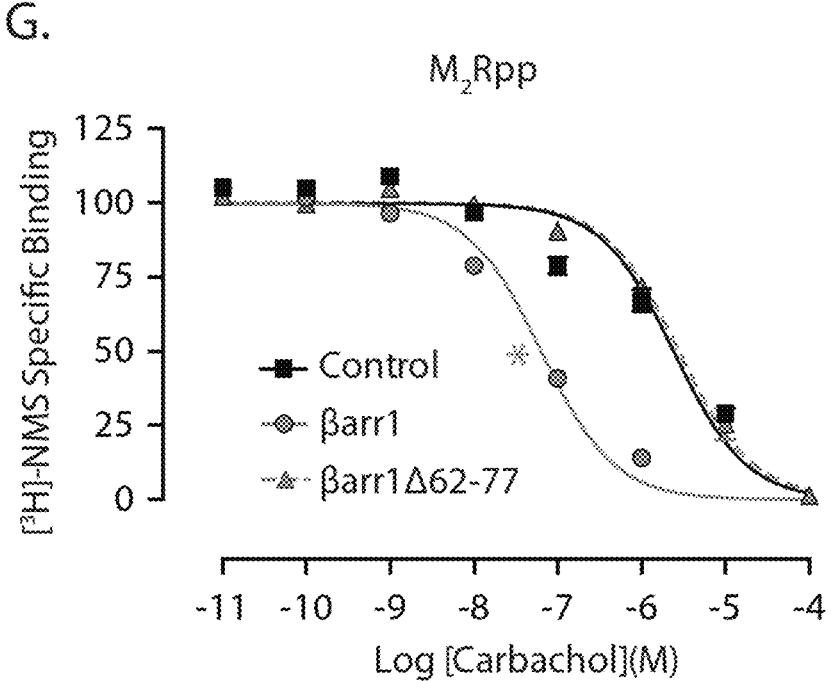

FIG. 9G shows competition binding assays using HDL-$M_2$Rpp performed as in FIG. 5A using a finger-loop deletion mutant of βarr1 (Δ62-77) (1 μM). Error bars represent standard error from at least three independent experiments. Stars (*) indicate log IC50 values significantly different from the control curve (P<0.05, one-way ANOVA).

Figure 10A:
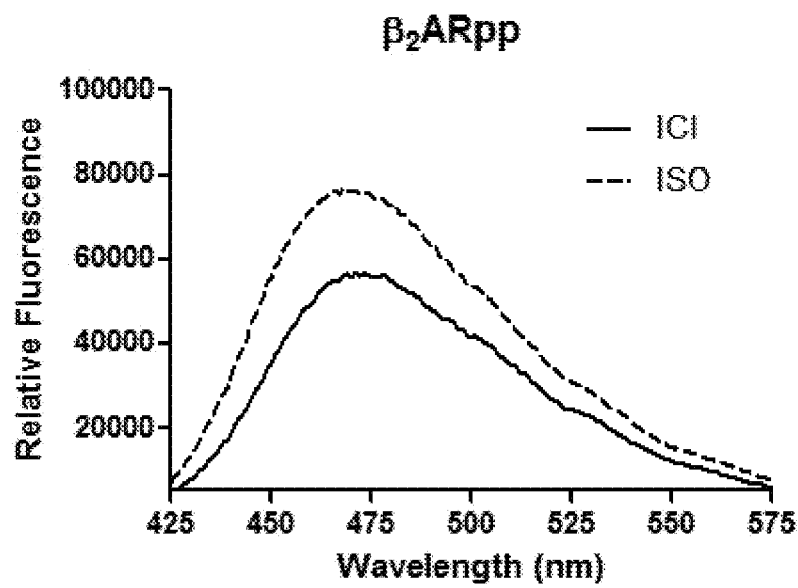

FIG. 10A shows an analysis of β-arrestin1 coupling to the transmembrane core of $\beta_2$ARpp by bimane fluorescence spectra of β-arrestin1 (βarr1) labeled with monobromobimane at residue 70 in the presence of $\beta_2$ARpp HDLs. Data are representative of three independent experiments.

Figure 10B:
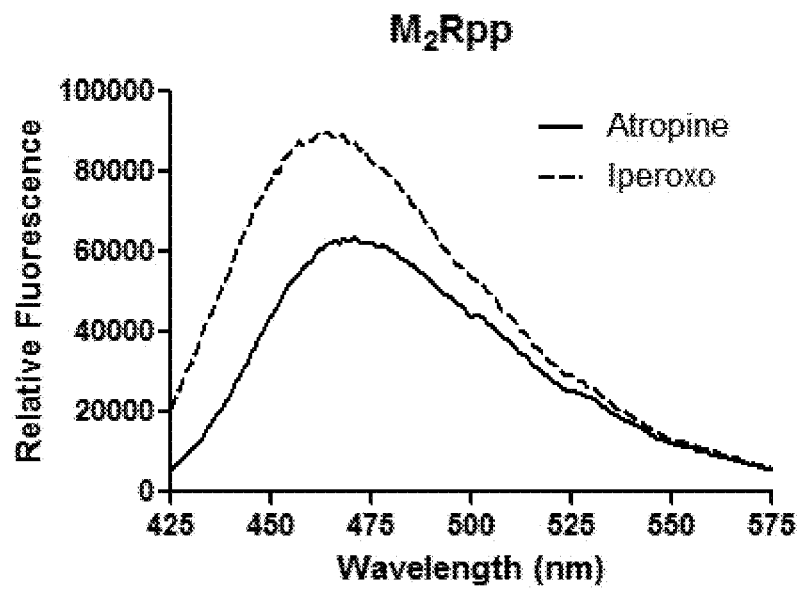

FIG. 10B shows an analysis of β-arrestin1 coupling to the transmembrane core of $M_2$Rpp by bimane fluorescence spectra of β-arrestin1 (βarr1) labeled with monobromobimane at residue 70 in the presence of $M_2$Rpp HDLs. Data are representative of three independent experiments.

Figure 10C:
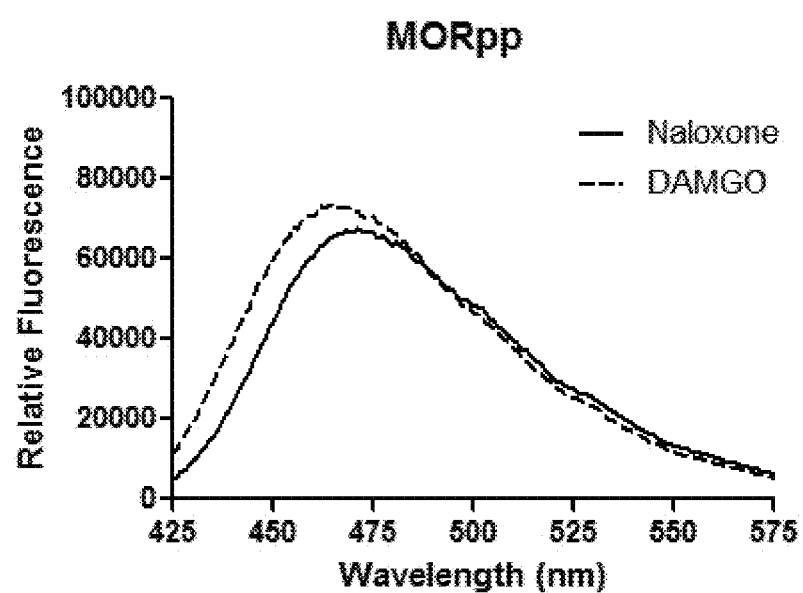

FIG. 10C shows an analysis of β-arrestin1 coupling to the transmembrane core of MORpp by bimane fluorescence spectra of β-arrestin1 (βarr1) labeled with monobromobimane at residue 70 in the presence of MORpp HDLs. Data are representative of three independent experiments.

Figure 11:
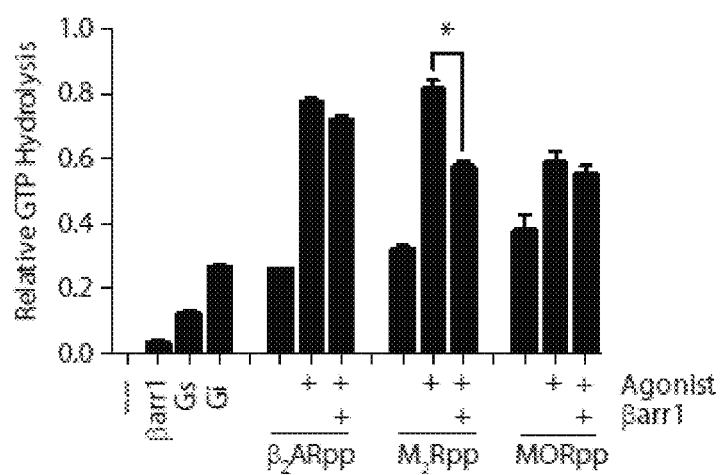

FIG. 11 shows the inhibition of G protein activation by β-arrestin1 correlates with its coupling strength to the receptor transmembrane core. The GTPase activity (GTP hydrolysis) of purified G protein (Gs or Gi) was measured in vitro in the presence and absence of $\beta_2$ARpp (Gs), $M_2$Rpp (Gi), and MORpp (Gi) HDLs. Treatment with the agonists isoproterenol (ISO) ($\beta_2$ARpp) or DAMGO (MORpp) increases G protein activation, which is not significantly altered by the presence of β-arrestin1 (βarr1). Activation of $M_2$Rpp with the agonist iperoxo increases G protein activation, which is significantly blocked by βarr1 (*P<0.05, one-way ANOVA). Error bars represent standard error from three independent experiments.

Figure 12:
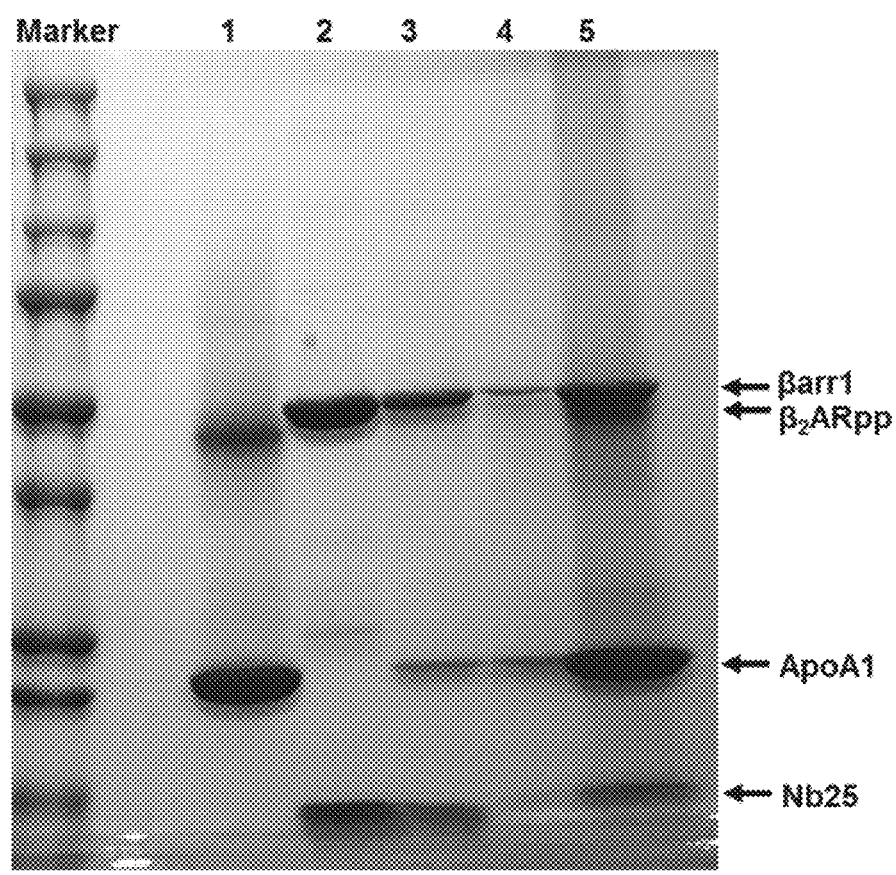

FIG. 12 shows complexes of sortase-ligated $\beta_2$ARpp with βarr1 and Nb 25 survive selection conditions for DNA-encoded library screening. Sortase-ligated $\beta_2$ARpp was reconstituted with biotinylated ApoA1 and complexed with βarr1 and the stabilizing nanobody Nb25. Complexes were immobilized on NeutrAvidin beads, washed, and eluted as previously described (Ahn et al., Mol Pharmacol 94, 850-861, 2018. (1) HDL-β$_2$ARpp input; (2) βarr1 and Nb25 input, (3) NeutrAvidin bead flow-through (unbound proteins and dissociated complexes), (4) NeutrAvidin bead washes (unbound proteins and dissociated complexes; 5×more sample loaded than other lanes), (5) NeutrAvidin bead elution (specifically bound complexes).

Figure 13:
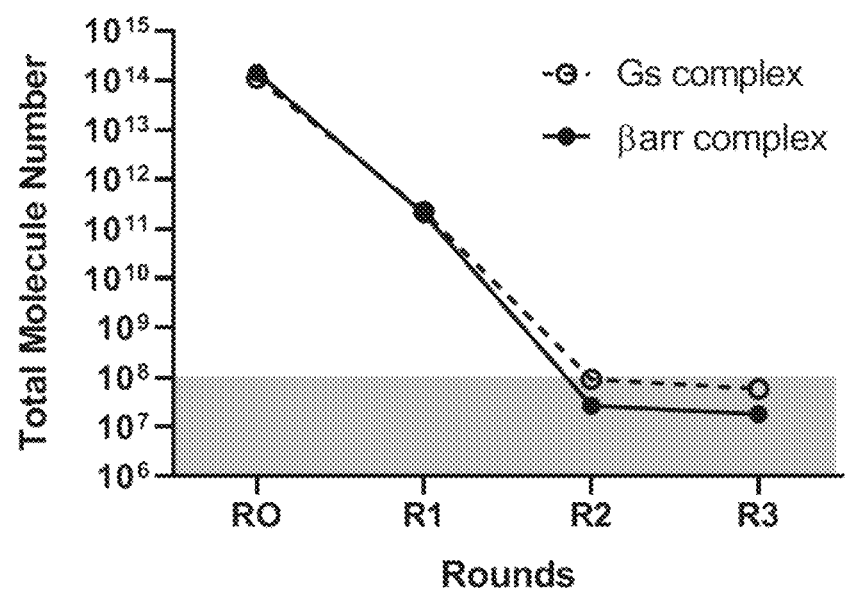

FIG. 13 shows complexes of HDL-β$_2$AR with heterotrimeric Gs protein and complexes of sortase-ligated β$_2$ARpp with βarr1 can be used to efficiently screen DNA-encoded small molecule libraries. In two rounds of selection for binding to these complexes, the library size is reduced to <10$^8$ molecules, enabling the selection output to be subjected to next-generation sequencing. This indicates that selection conditions are appropriately stringent to remove non-specifically bound molecules in the library. R0=DNA-encoded library input, R1 and R2=selection for binding to immobilized receptor/transducer complexes, R3=counter selection against His-tagged Gs and His-tagged Nb25+βarr1 bound to NiNTA beads.

Figure 14A:
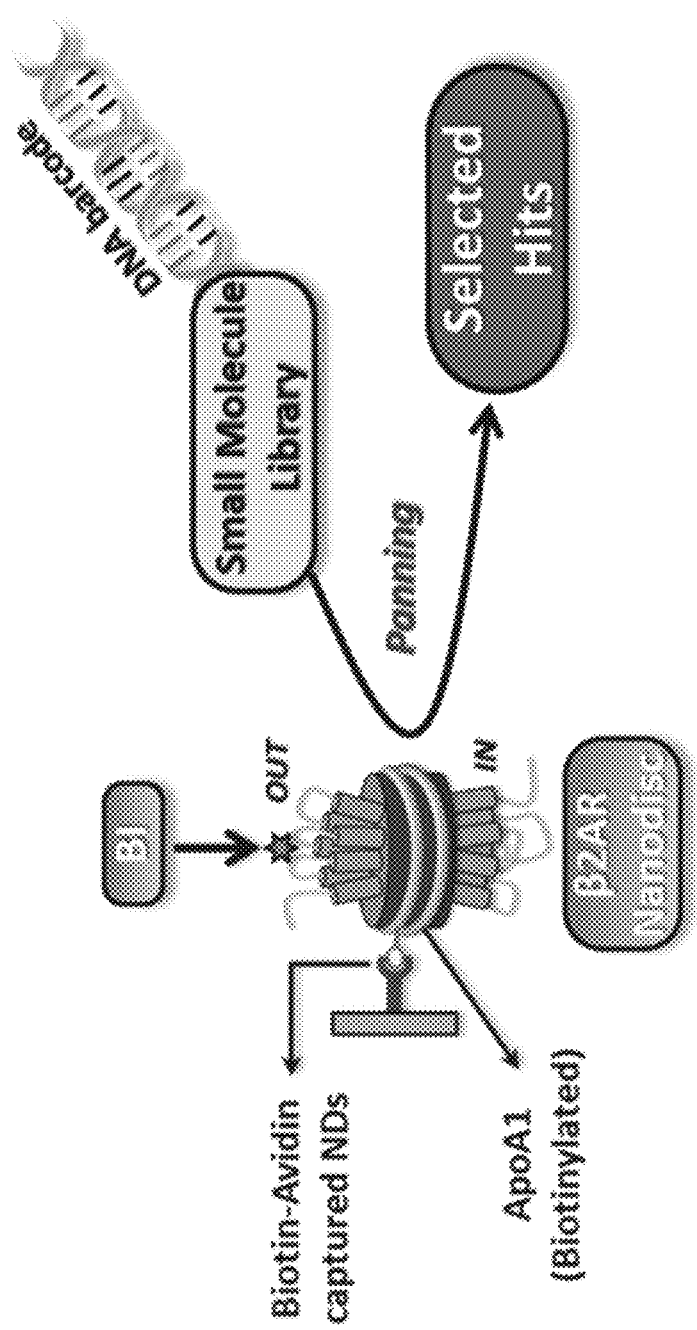

FIG. 14A shows a cartoon for DNA-encoded small molecule screening of the β$_2$AR reconstituted in high density lipoprotein (HDL) particles using a biotinylated version of the membrane scaffolding protein ApoA1, where the orthosteric site of the receptor is occupied by a high affinity β-agonist BI-167107 to hold the receptor more in an active conformation.

Figures 14B, 14C, 14D:
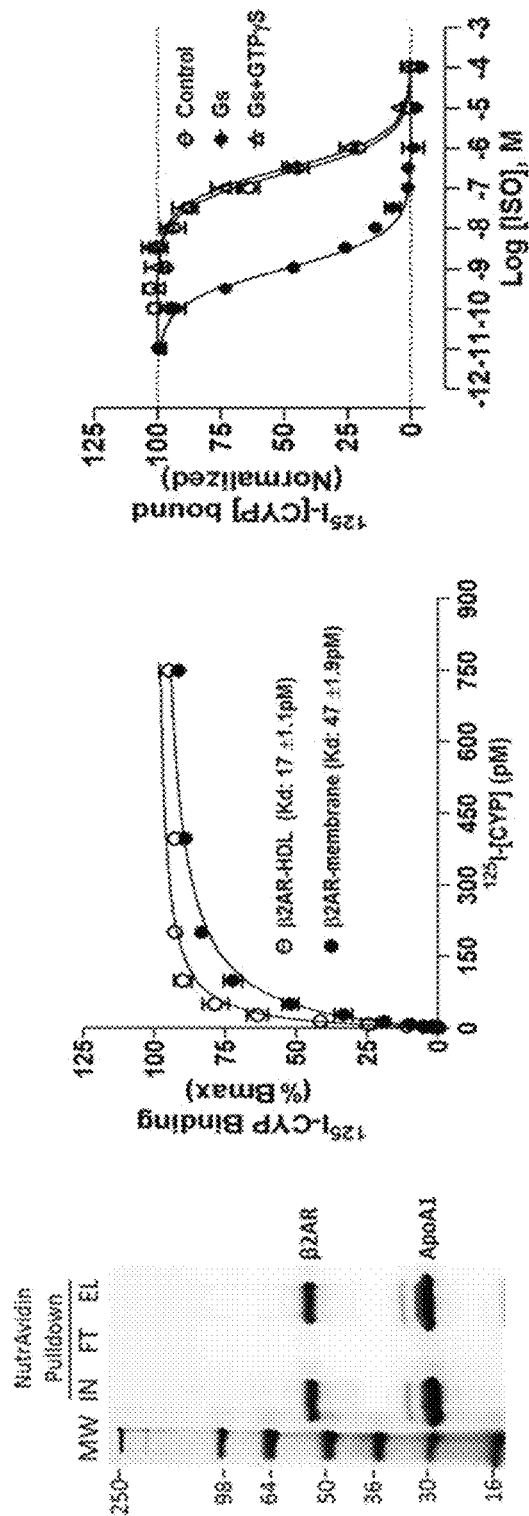

FIG. 14B shows that the β2 receptor containing biotinylated-HDLs can be efficiently captured on NeutrAvdin beads.

FIG. 14C shows that the β2 receptor containing biotinylated-HDLs have comparable affinity for antagonist binding to that of β2ARs in membrane preparations.

FIG. 14D shows that β2ARs in HDL particles can functionally couple to heterotrimeric Gs in competitive radioligand binding assays.

Figure 14E:
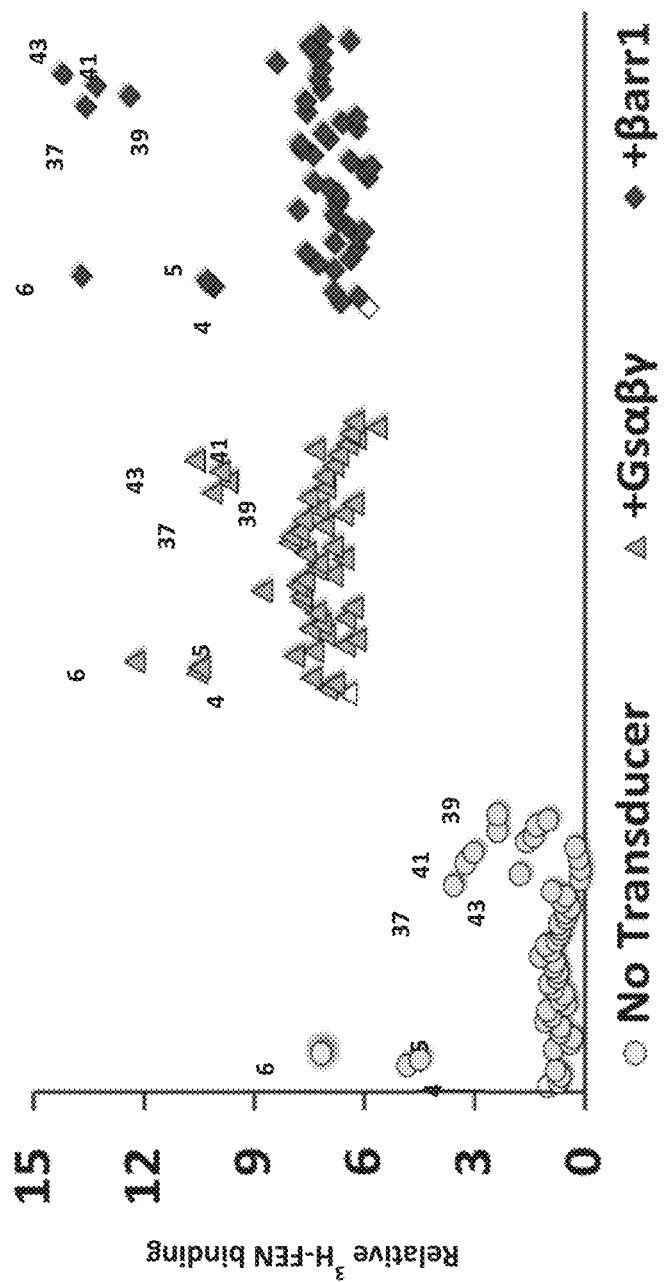

FIG. 14E shows the activity of 50 potential screening hits to increase binding of a radiolabeled agonist [$^3$H](R,R')-4-methoxyfenoterol ($^3$H-FEN) to the β2AR expressing on cell membranes in the absence and presence of the transducer proteins G protein and β-arrestin.

Figure 14F:
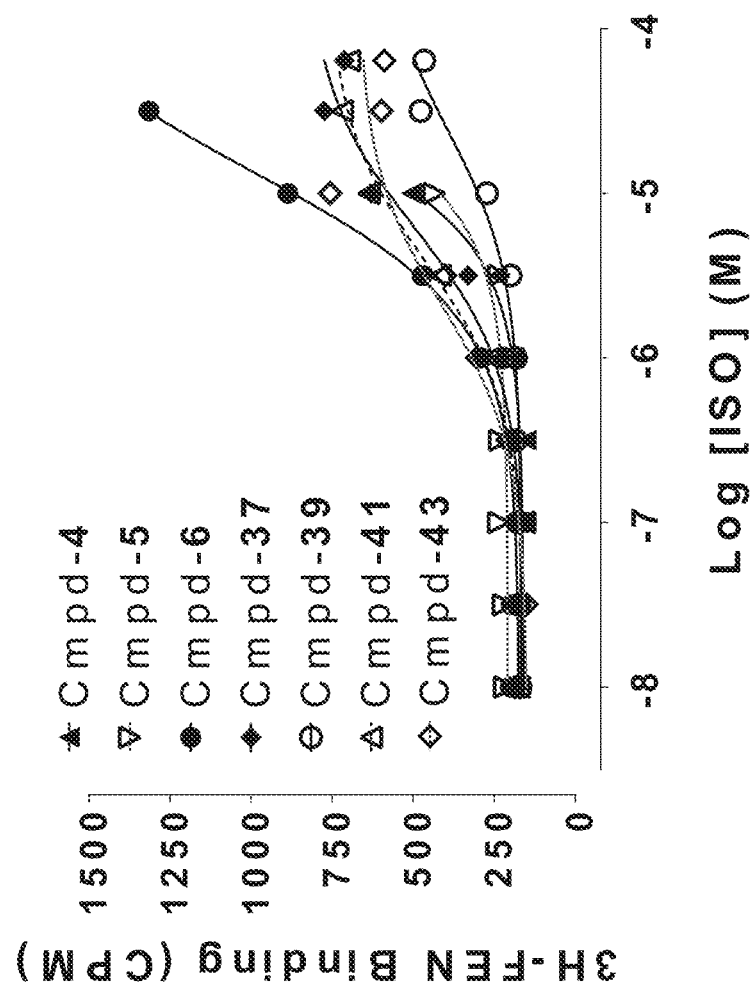

FIG. 14F shows the concentration response curves for seven compounds identified from the screening as potential β$_2$AR PAMs.

Figure 14G:
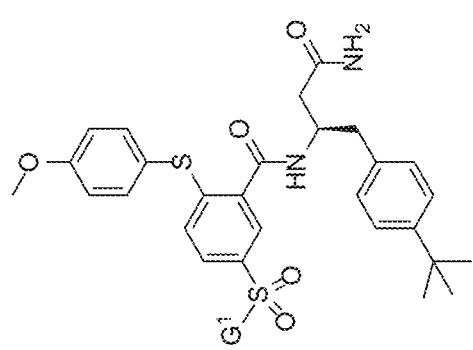

FIG. 14G shows the structures of the seven compounds for which data is shown in FIG. 1F.

Figure 14H:
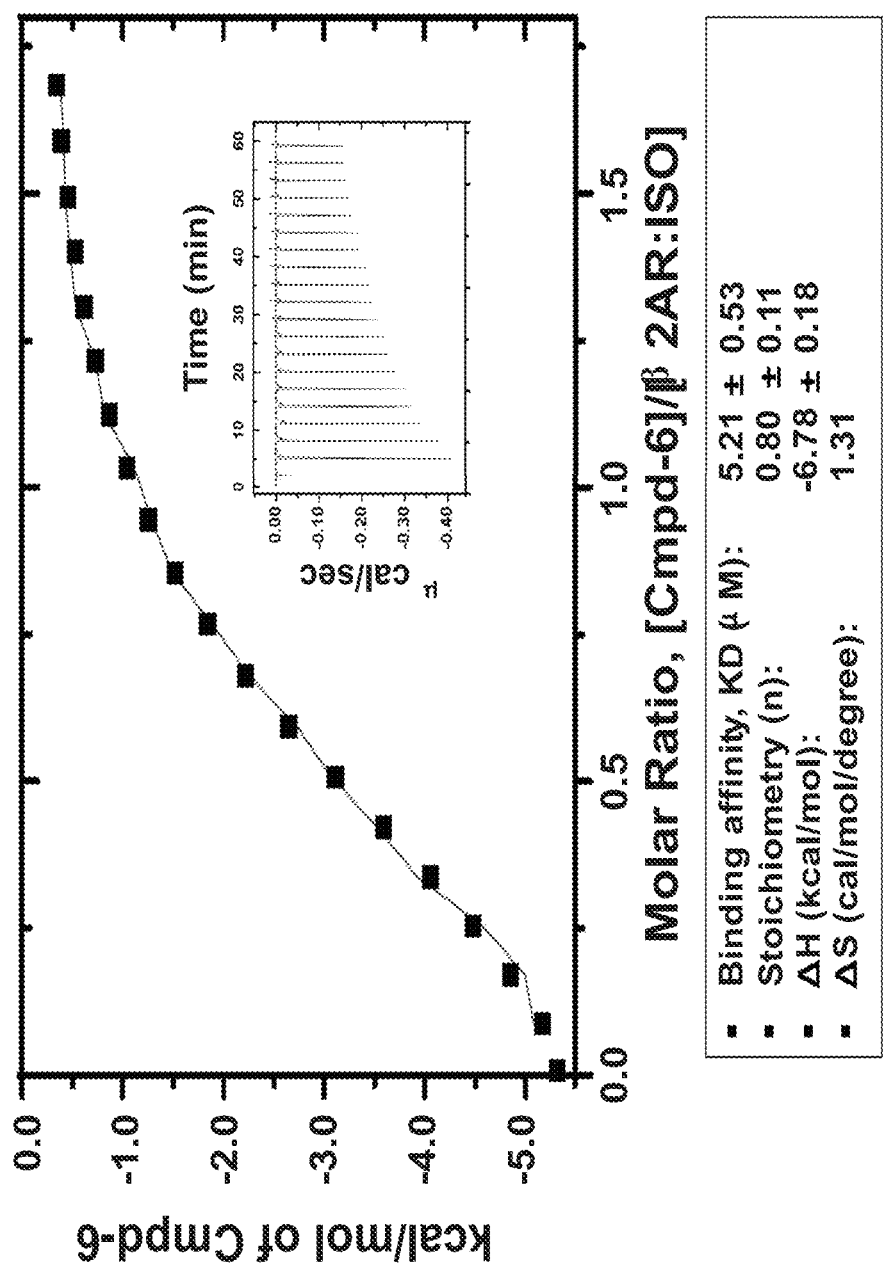

FIG. 14H shows isothermal titration calorimetry (ITC) for Compound 6. The values summarize binding affinity (K$_D$), stoichiometry (N), and thermodynamic parameters.

Figures 15A, 15B:
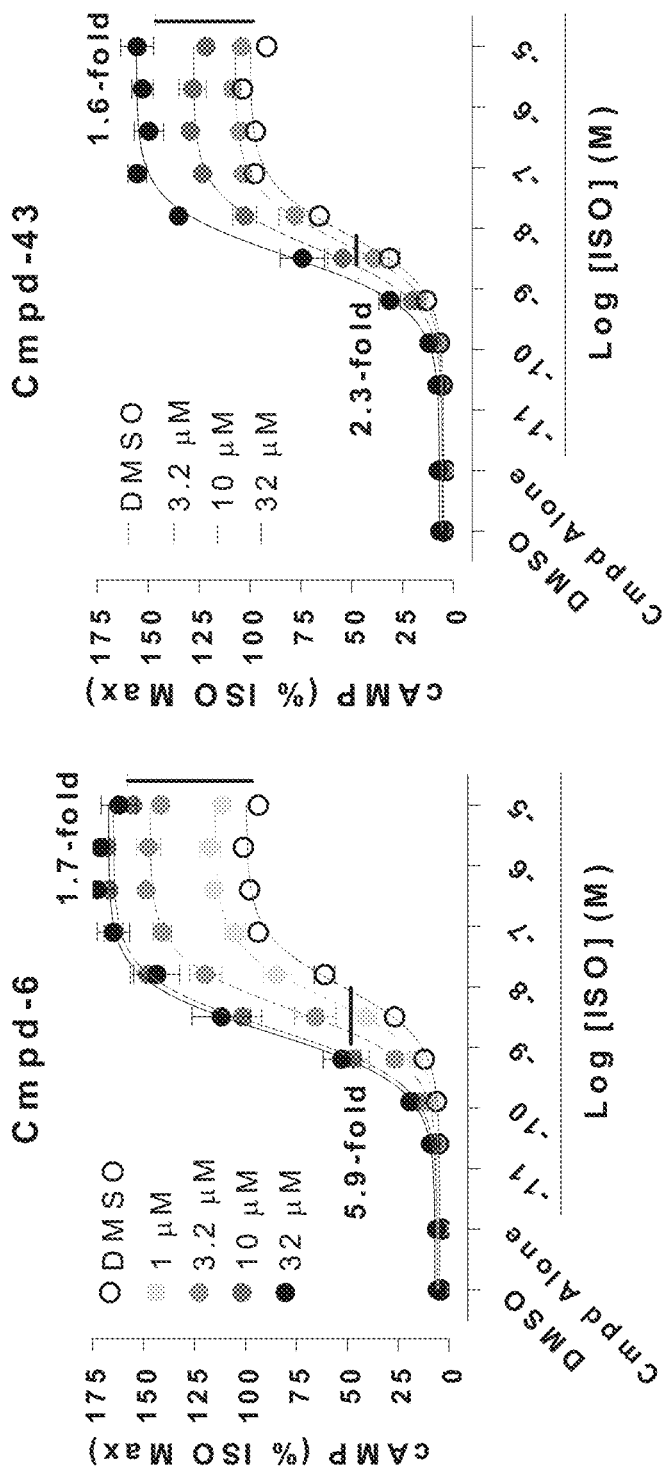

FIG. 15A shows activity of Compound 6 to increase the ability of an agonist, isoproterenol (ISO) to activate G protein-mediated cAMP production through the β2AR in a dose-dependent way.

FIG. 15B shows activity of Compound 43 to increase the ability of an agonist, isoproterenol (ISO) to activate G protein-mediated cAMP production through the β2AR in a dose-dependent way.

Figures 15C, 15D:
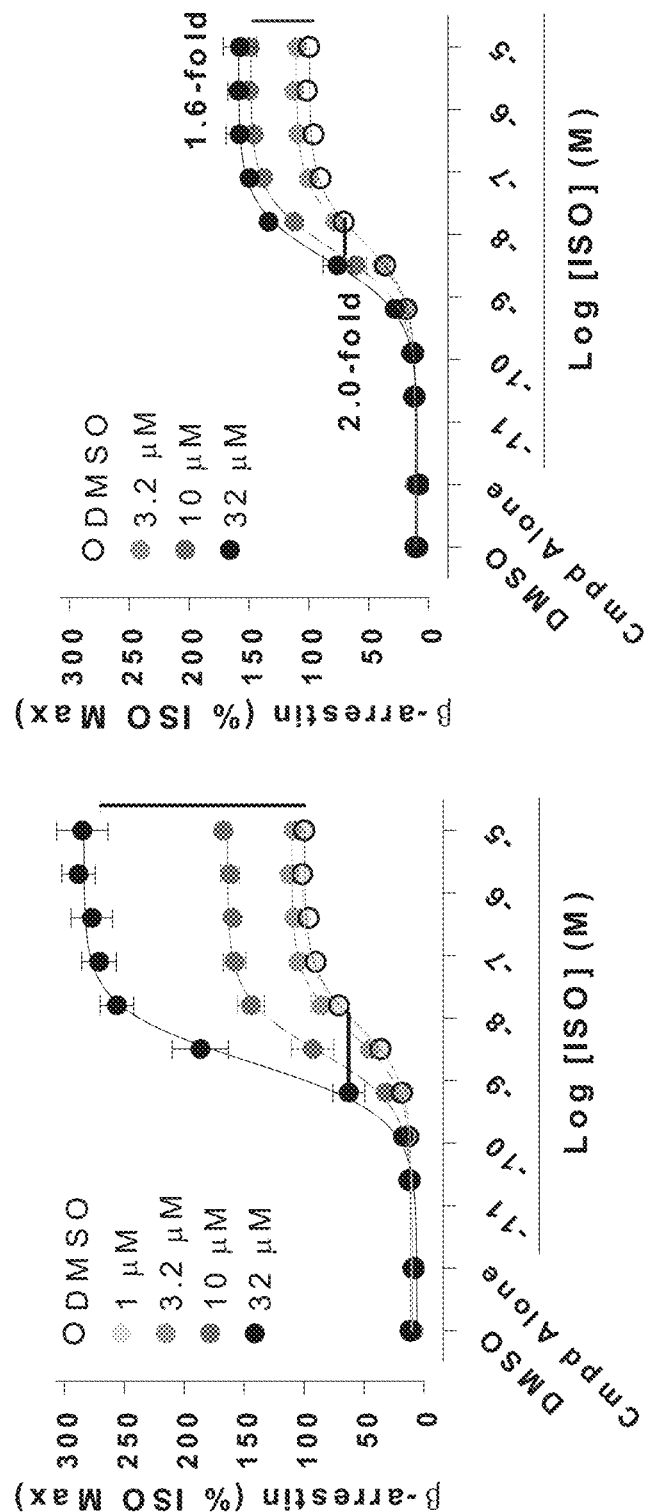

FIG. 15C shows activity of Compound 6 to increase the ability of an agonist, isoproterenol (ISO) to recruit β-arrestin to the β2V2R, a chimeric receptor with a V$_2$R tail at the C-terminus that displays stronger and more stable agonist-promoted β-arrestin binding than the native β2AR while retaining the pharmacological properties of the native β2AR.

FIG. 15D shows activity of Compound 43 to increase the ability of an agonist, isoproterenol (ISO) to recruit β-arrestin to the β2V2R.

Figure 16B:
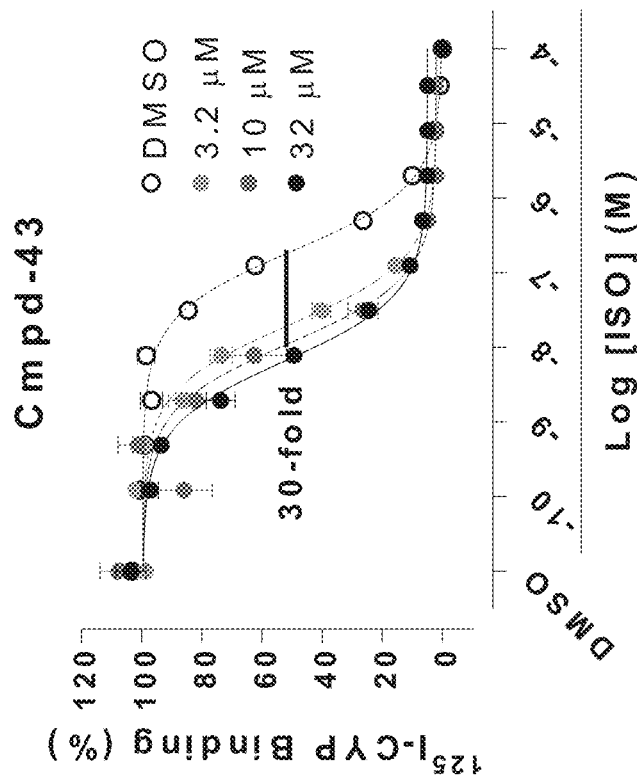
Figure 16A:
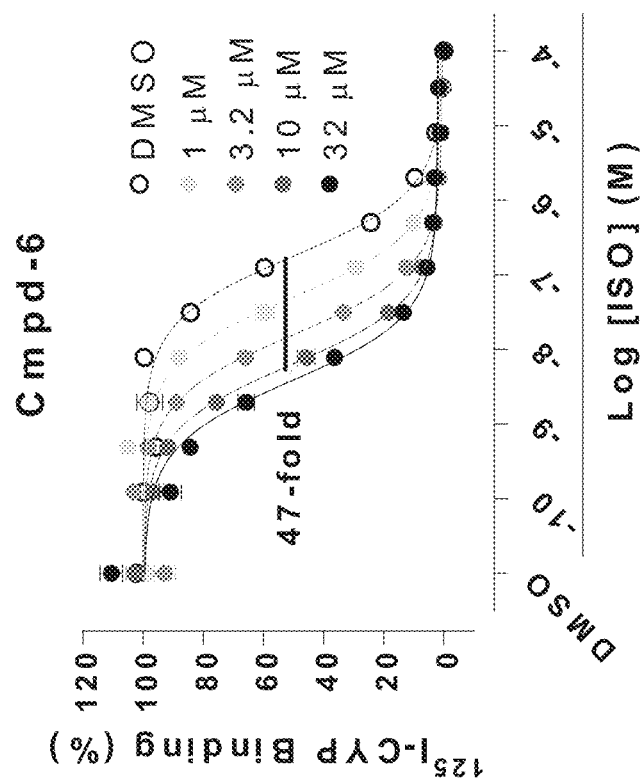

FIG. 16A shows Compound 6-mediated dose-dependent left-shifts of the isoproterenol competition curve in [$^{125}$I]-cyanopindolol ($^{125}$I—CYP) binding to the β2AR reconstituted in HDL particles.

FIG. 16B shows Compound 43-mediated dose-dependent left-shifts of the isoproterenol competition curve in $^{125}$I—CYP binding to the β2AR reconstituted in HDL particles.

Figure 16D:
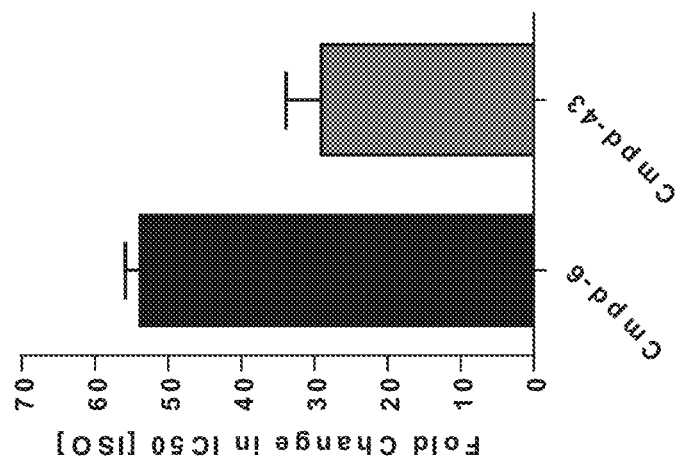
Figure 16C:
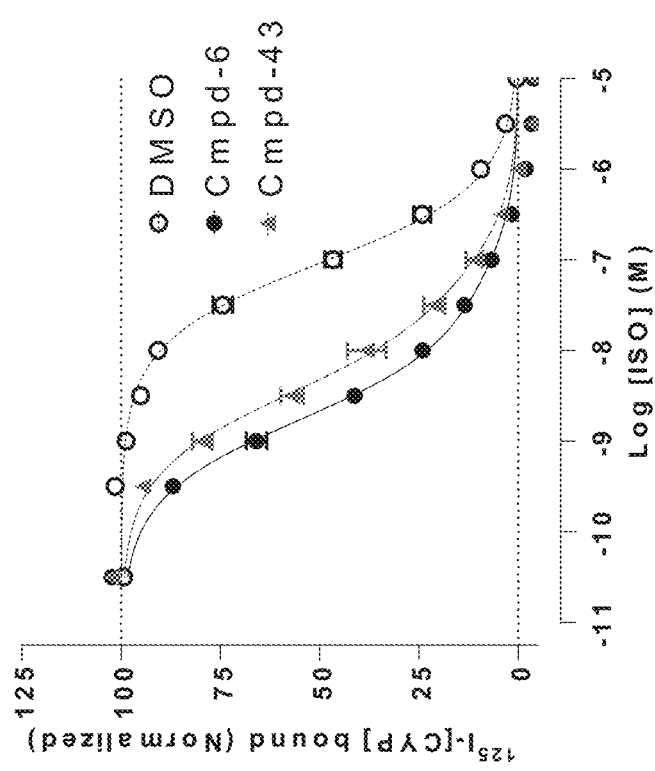

FIG. 16C shows Compound 6- and Compound 43-mediated dose-dependent left-shifts of the isoproterenol competition curve in $^{125}$I—CYP binding with membranes prepared from β2AR-overexpressing cells.

Figure 3A:
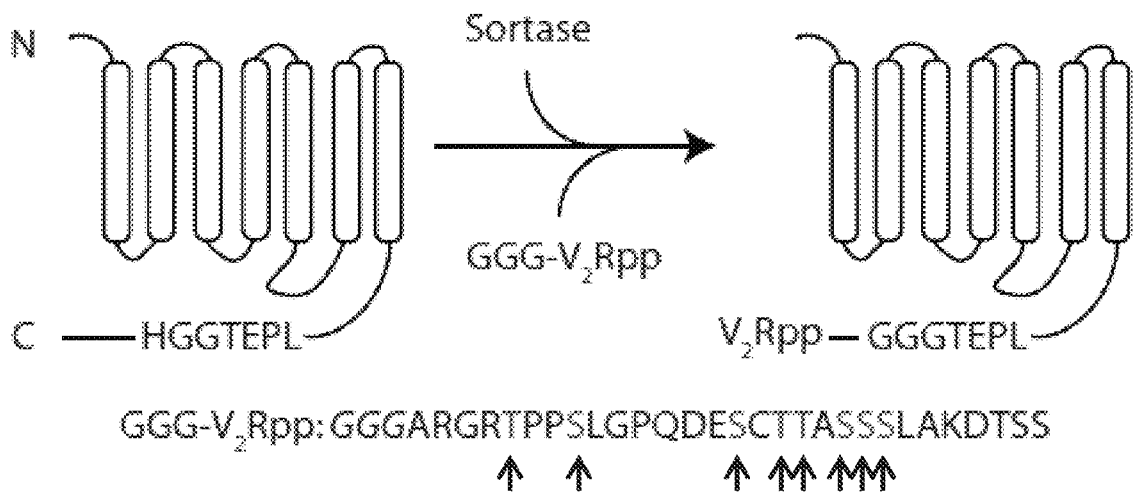
Figure 3B:
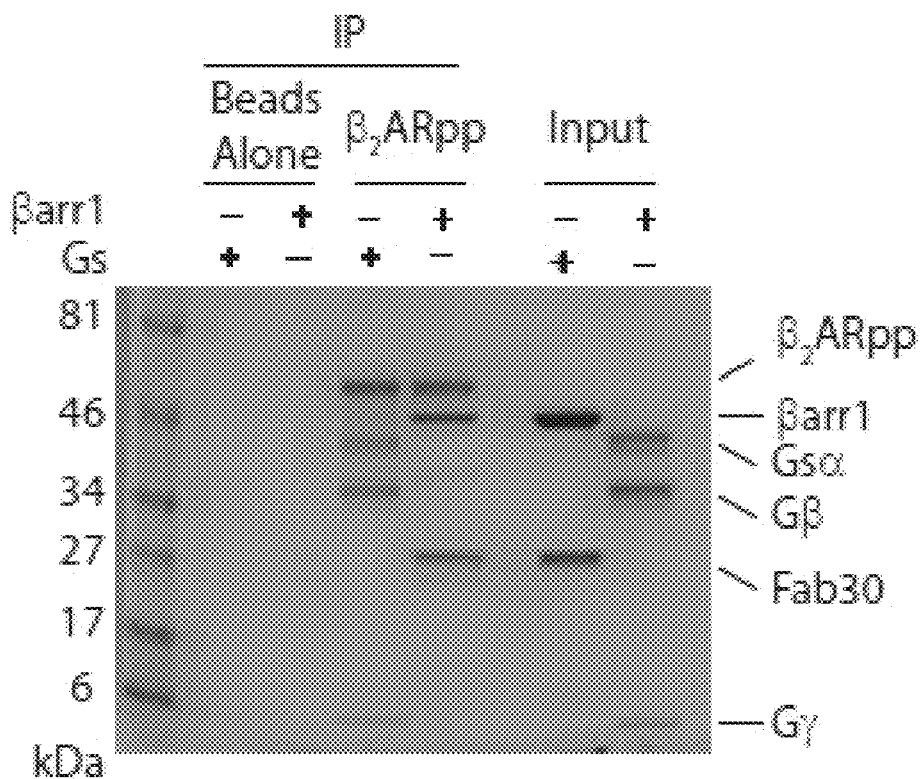
Figure 3C:
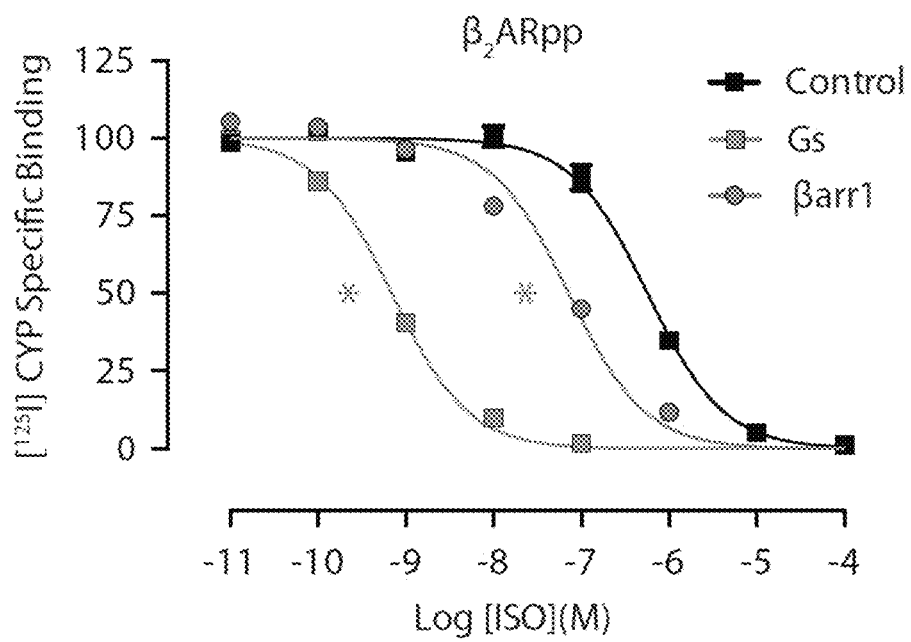

FIG. 16D shows the fold change in $^{125}$I—CYP binding to the β2AR for the data in FIG. 3C.

Figure 16E:
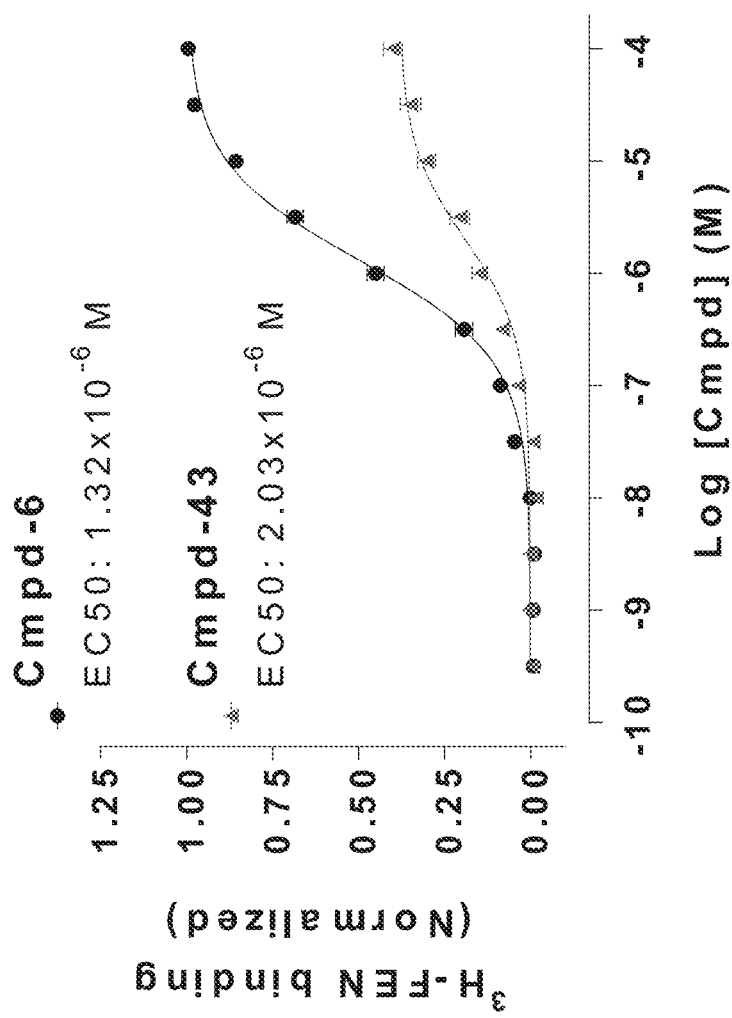

FIG. 16E shows Compound 6 and Compound 43-mediated dose-dependent increases in $^3$H-FEN binding to the β2AR.

Figure 17:
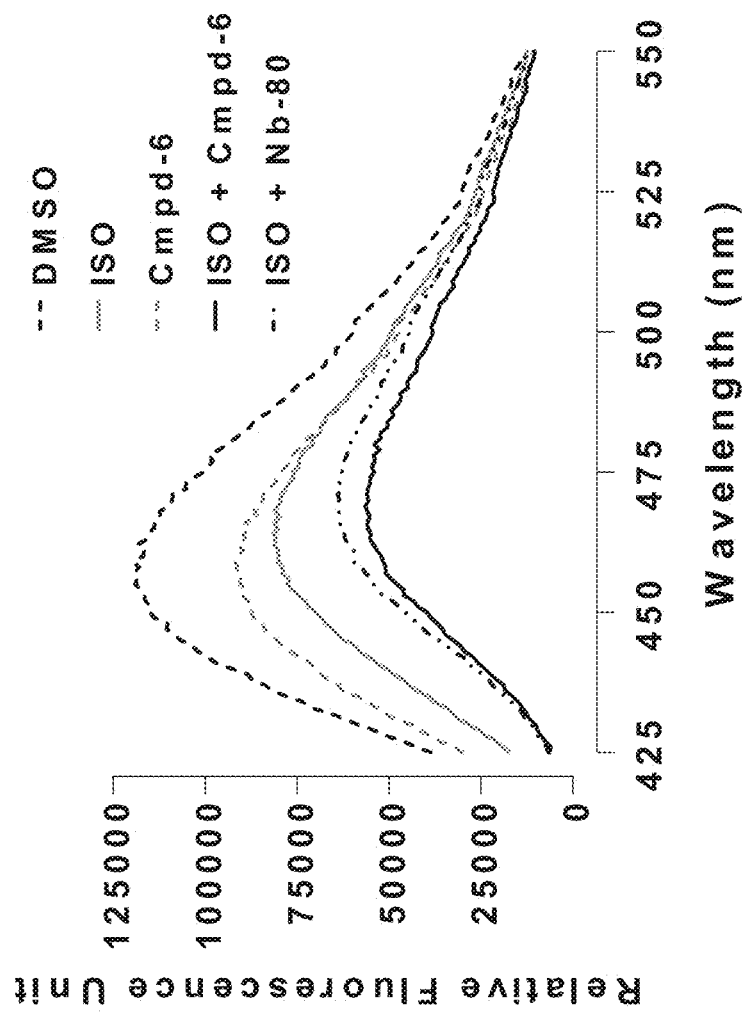

FIG. 17 shows the positive allosteric effects of Compound 6 to stabilize the active conformation of the β2AR, measured as the potentiation of ISO-induced decreases in the amount of fluorescence and increases in the maximum wavelength from the monobromobimane-labeled β2AR in HDL particles.

Figures 18A, 18B:
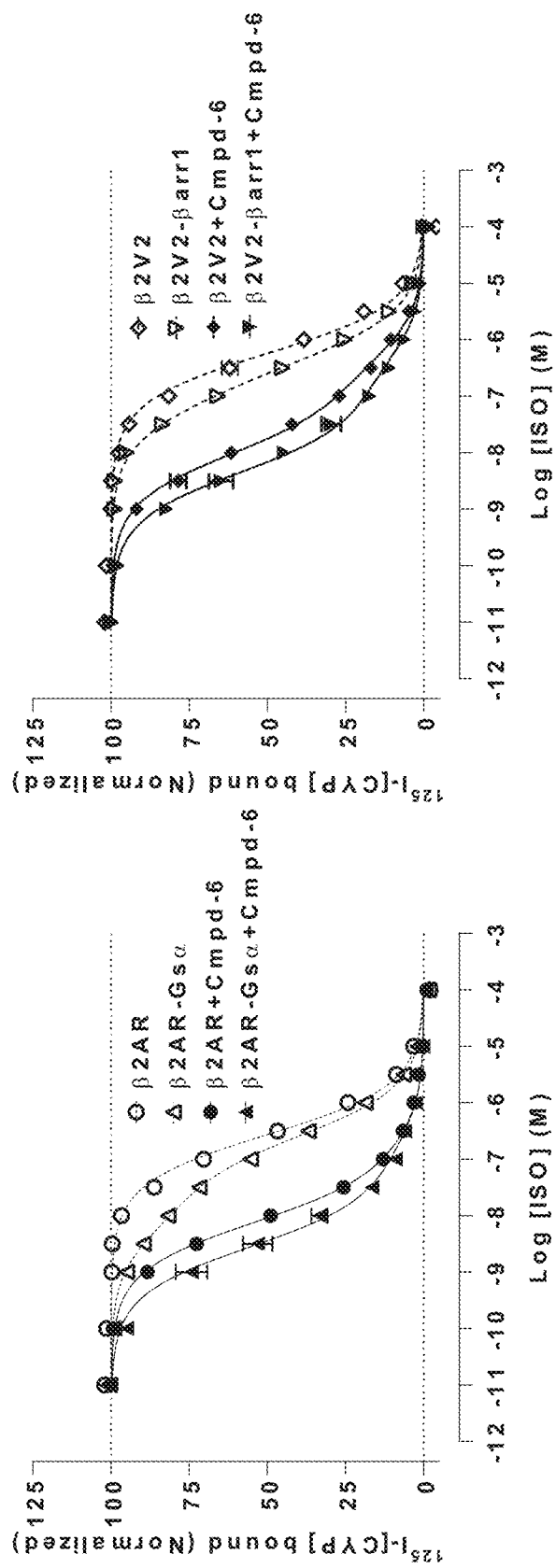

FIG. 18A shows Compound-6-induced shifts of the isoproterenol competition curve to the left in $^{125}$I—CYP binding to the β2AR obtained with membranes from cells expressing the β2AR or β2AR-Gs fusions.

FIG. 18B shows Compound-6-induced shifts of the isoproterenol competition curve to the left in $^{125}$I—CYP binding to the β2AR obtained with membranes from cells expressing the β2AR or β2V2R-βarr fusions.

Figures 18C, 18D:
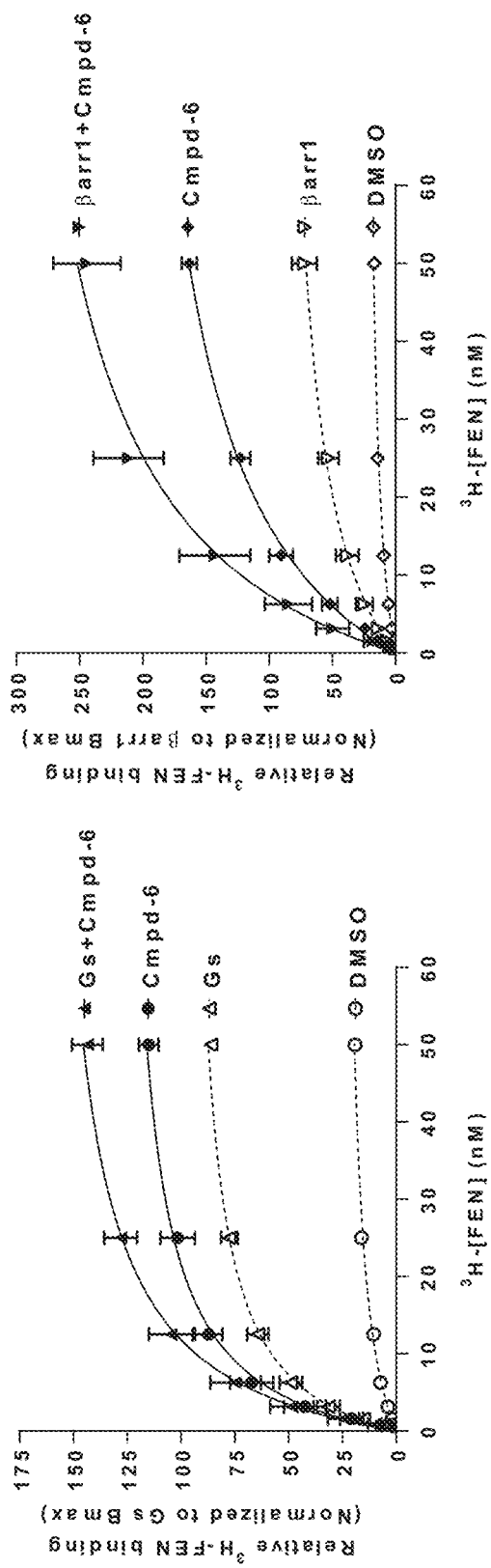

FIG. 18C shows the effect of Compound 6 to increase $^3$H-FEN binding to the β2AR in the presence of Gs.

FIG. 18D shows the effect of Compound 6 to increase $^3$H-FEN binding to the β2AR in the presence of β-arrestin.

Figure 19:
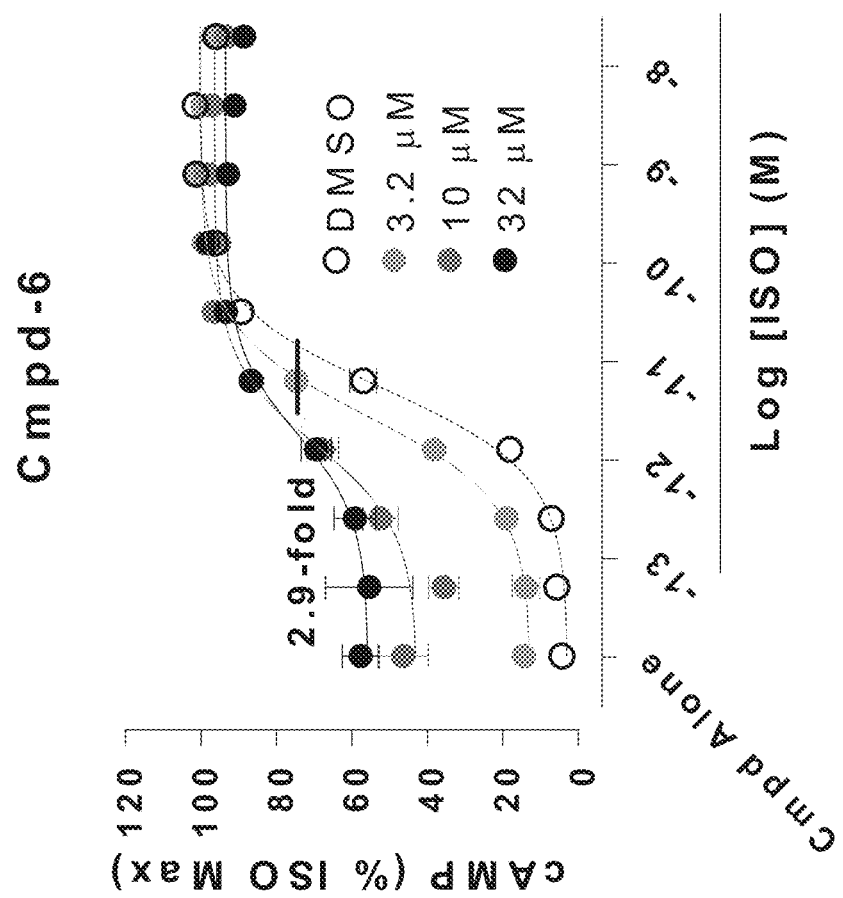

FIG. 19 shows the effect of ISO-induced cAMP production by the overexpressed β2AR in the presence of the indicated concentrations of Compound-6.

Figures 20A, 20B:
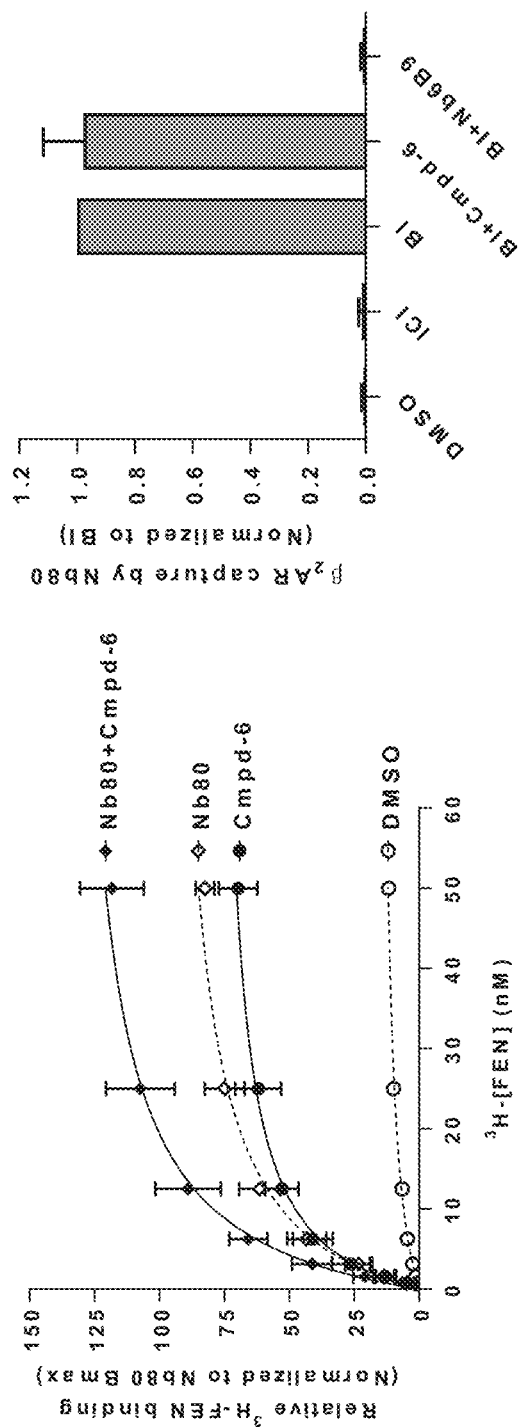

FIG. 20A shows the effect of Compound 6 to increase $^3$H-FEN binding to the β2AR in the presence of the G-protein mimic Nb80.

FIG. 20B shows β2AR capture by Nbs (Nb80) using ELISA in the presence of the high-affinity agonist BI-167107, and compared to DMSO or the antagonist ICI-118551, a competing nanobody Nb-6B9, and saturating concentration of Compound-6.

Figures 21A, 21B:
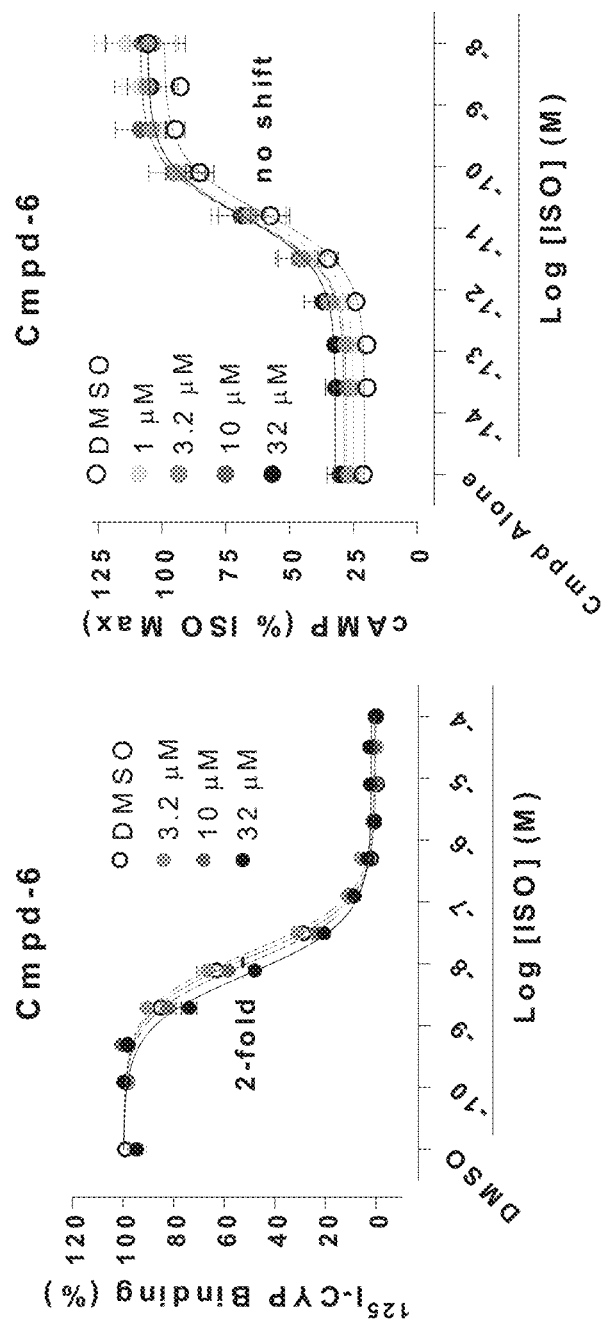

FIG. 21A shows the effect of Compound 6 on the ISO competition curve for binding to the β1AR against the $^{125}$I—CYP radiolabeled antagonist.

FIG. 21B shows the effect of Compound 6 on the ISO concentration response at β1AR-mediated cAMP production.

Figures 22A, 22B, 22C, 22D:
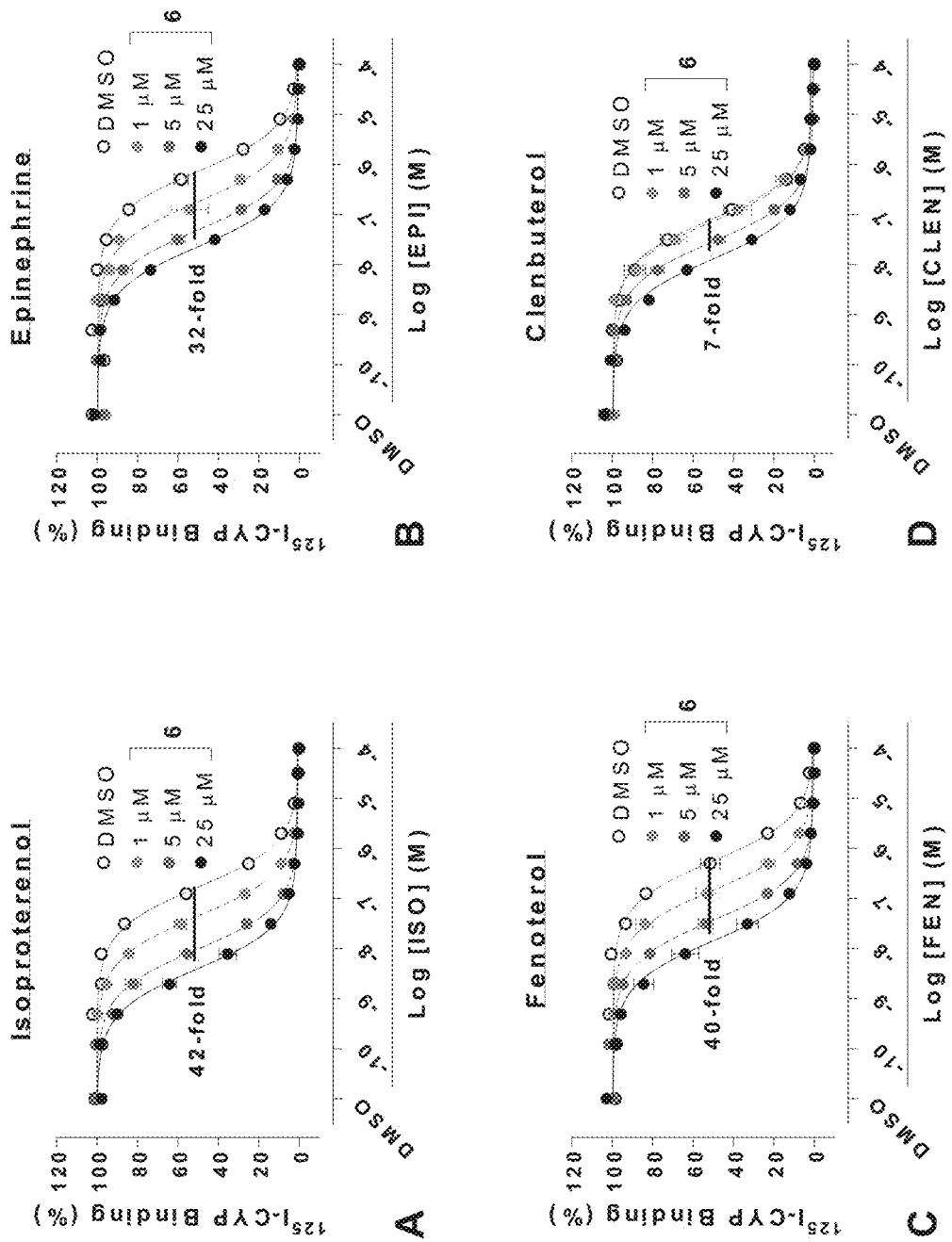

FIG. 22A shows the effect of Compound 6 on the radioligand ($^{125}$I—CYP) competition binding dose-response curve (IC50 value) for ISO.

FIG. 22B shows the effect of Compound 6 on the radioligand ($^{125}$I—CYP) competition binding dose-response curve (IC50 value) for epinephrine.

FIG. 22C shows the effect of Compound 6 on the radioligand ($^{125}$I—CYP) competition binding dose-response curve (IC50 value) for fenoterol.

FIG. 22D shows the effect of Compound 6 on the radioligand ($^{125}$I—CYP) competition binding dose-response curve (IC50 value) for clenbuterol.

FIG. 22E shows the effect of Compound 6 on agonist-mediated cAMP accumulation dose-response by ISO.

FIG. 22F shows the effect of Compound 6 on agonist-mediated cAMP accumulation dose-response by epinephrine.

FIG. 22G shows the effect of Compound 6 on agonist-mediated cAMP accumulation dose-response by fenoterol.

FIG. 22H shows the effect of Compound 6 on agonist-mediated cAMP accumulation dose-response by clenbuterol.

Figures 22I, 22J, 22K, 22L:
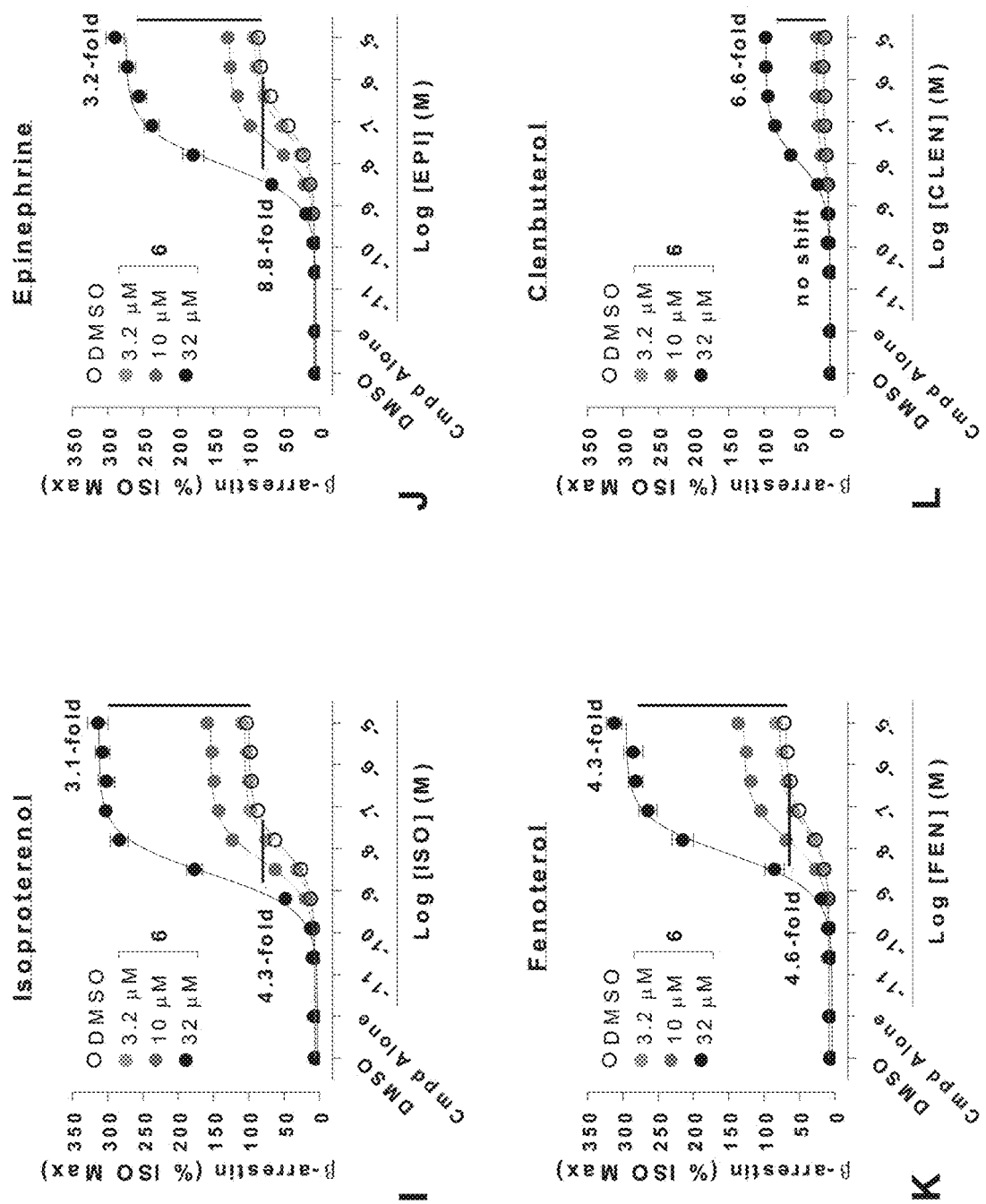

FIG. 22I shows the effect of Compound 6 on agonist-mediated β-arrestin recruitment dose-response by ISO.

FIG. 22J shows the effect of Compound 6 on agonist-mediated β-arrestin recruitment dose-response by epinephrine.

FIG. 22K shows the effect of Compound 6 on agonist-mediated β-arrestin recruitment dose-response by fenoterol.

FIG. 22L shows the effect of Compound 6 on agonist-mediated β-arrestin recruitment dose-response by clenbuterol.

FIG. 23 shows activity data for representative compounds of the invention.

DETAILED DESCRIPTION OF THE INVENTION

A. Homogeneous GPCR Phosphorylation

The present disclosure is predicated, at least in part, on the discovery that sortase-mediated ligation of a synthetic phosphopeptide to the C-terminus of GPCRs can be used to homogeneously phosphorylate GPCRs so that the effects of β-arrestin coupling to the transmembrane (TM) cores may be elucidated. The complex and methods disclosed herein allow for systematic comparison as to how agonists allosterically influence the interactions of multiple transducers with multiple GPCRs, revealing unexpected diversity that may influence the balance of cellular signaling responses. In this regard, verifying the efficiency and pattern of phosphorylation for GPCRs is known in the art to be technically challenging. As a result, it has been difficult to ascertain whether particular structural elements directly affect GPCRs' interactions with βarr or indirectly influence them at the level of GRK phosphorylation. The sortase-ligated chimeric receptor complexes described herein provide a tool to separate these variables, enabling independent manipulation of phosphorylation state and βarr binding to clarify the structural requirements of the GPCR-βarr interaction.

1. Chimeric GPCR Complex and In Vitro Production

The disclosure provides a complex comprising (i) a chimeric G protein-coupled receptor (GPCR) comprising the amino acid sequence LPETGGG (SEQ ID NO: 1) located within the C-terminus of the GPCR and a synthetic phosphopeptide ligated to SEQ ID NO: 1; and (ii) a β-arrestin (βarr) protein bound to the C-terminus of the GPCR. The term "complex," as used herein, refers to at least two molecules that are specifically associated with each other, such as, for example, by directly binding to each other. The associate between the at least two molecules of a complex may involve one or more chemical or physical bonds and/or chemical spacers providing such bond(s) (e.g., non-specific attachment via van der Waals forces, hydrogen bonding, covalent bonding electrostatic interactions, hydrophobic/hydrophilic interactions; etc.). The term "chimeric," as used herein, refers to a substance or compound that is composed of parts of different origin.

As discussed above, G protein-coupled receptors (GPCRs) are the largest, most versatile, and most ubiquitous of the several families of plasma membrane receptors. GPCRs regulate virtually all known physiological processes in mammals. GPCRs are the largest family of membrane proteins and mediate most cellular responses to hormones and neurotransmitters, as well as being responsible for vision, olfaction, and taste. All GPCRs are characterized by the presence of seven membrane-spanning α-helical segments separated by alternating intracellular and extracellular loop regions. GPCRs in vertebrates are commonly divided into five families on the basis of their sequence and structural similarity: rhodopsin (family A), secretin (family B), glutamate (family C), adhesion, and Frizzled/Taste2. The rhodopsin family is by far the largest and most diverse of these families, and members are characterized by conserved sequence motifs that imply shared structural features and activation mechanisms. Despite these similarities, individual GPCRs have unique combinations of signal-transduction activities involving multiple G-protein subtypes, as well as G-protein-independent signaling pathways and complex regulatory processes. Moreover, they are the most common targets of currently used therapeutic drugs, and it is estimated that nearly 36% of all FDA-approved drugs target at least one member of the GPCR gene family (Overington et al., Nat. Rev. Drug. Disc., 5: 993 (2006); and Rask-Andersen et al., Nat. Rev. Drug. Disc., 10: 579 (2011)).

G protein-coupled receptor (GPCR) signaling begins when an agonist binds to and stabilizes an active receptor conformation. This agonist bound GPCR, acting through its transmembrane core, promotes interaction with heterotrimeric G proteins (Gαβγ), thus stimulating guanine nucleotide exchange and separation of the Gα subunit from the Gβγ subunits (Gilman, A G., Annu Rev. Biochem, 56: 615-649 (1987)). Once activated, GPCRs initiate a highly conserved signaling and regulatory cascade marked by interactions with: (i) heterotrimeric G proteins, which mediate their actions largely by promoting second-messenger generation (Gilman, supra); (ii) GPCR kinases (GRKs), which phosphorylate activated conformations of receptors (Moore et al., Annu Rev Physiol 69:451-482 (2007)); and (iii) β-arrestins (βarrs), which bind to the phosphorylated receptors to mediate desensitization of G protein signaling and receptor internalization (Goodman et al., Nature, 383(6599):447-450 (1996); and Laporte et al., Proc Natl Acad Sci USA 96(7): 3712-3717). GPCR receptor complexes and signaling pathways are further described in, e.g., Kroeze et al., J. Cell Sci., 116: 4867-4869 (2003); Rosenbaum et al., Nature, 459 (7245): 356-363 (2009); Cahill et al., Proc. Natl. Acad. Sci. USA, 114(10): 2562-2567 (2017); and Thomsen et al., Cell, 166(4): 907-919 (2016).

Nearly 800 GPCRs have been identified in humans, which are classified into numerous types and subtypes within the five families identified above based on sequence homology and functional similarity. In the context of the present disclosure, the chimeric GPCR can be obtained or derived from any GPCR family, group, subgroup, type, or subtype known in the art, such as those described in, e.g., (Bjarnadóttir et al., Genomics, 88(3): 263-73 (2006); Attwood, T. K. and J. B. Findlay, Protein Engineering, 7(2): 195-203 (1994); Kolakowski, L. F., Receptors & Channels, 2(1): 1-7 (1994); and Foord et al., Pharmacological Reviews, 57(2): 279-288 (2005)). In one embodiment, the chimeric GPCR is a member of the adrenergic receptor family (e.g., α1A, α1B, α1D, α2A, α2B, α2C, β1, or β2 adrenergic receptor), a member of the dopamine receptor family (e.g., D1, D2, D3, D4, or D5 dopamine receptor), a member of the opioid receptor family (e.g., delta, kappa, mu, nociceptin, or zeta opioid receptor), a member of the muscarinic acetylcholine receptor family (e.g., M₁, M₂, M₃, M₄, or M₅ receptor), calcitonin receptor (CTR), a cannabinoid receptor (e.g., type 1 (CB1R) or type 2 (CB2R) receptor), a chemokine receptor (e.g., C—X—C chemokine receptor 4 (CXCR4)), a free fatty acid receptor (e.g., FFA1, FFA2, FFA3, or FFA4 receptor), G protein-coupled receptor 3 (GPR3), glucagon-like peptide 1 receptor (GLP-1R), a parathyroid hormone receptor (e.g., PTH1R or PTH2R), a somatostatin receptor (e.g., SSTR1, SSTR2, SSTR3, SSTR4, SSTR5), a sphingosine-1 phosphate receptor (e.g., S1P1R, S1P2R, S1P3R, S1P4R, or S1P5R), a vasopressin receptor, an angiotensin receptor, or thyroid stimulating hormone receptor (TSHR). For example, the chimeric GPCR may be β2-adrenergic receptor, angiotensin II type 1A receptor, vasopressin V2 receptor, μ opioid receptor (MOR), or muscarinic acetylcholine receptor 2 (M₂R).

The GPCR is "chimeric" in that it comprises a non-native amino acid sequence located within the GPCR C-terminus and a synthetic (i.e., man-made and not naturally occurring) phosphopeptide ligated to the non-native amino acid sequence. The terms "C-terminus," "carboxyl-terminus," "carboxy-terminus," "C-terminal tail," "C-terminal end," and "COOH-terminus" are synonymous and used interchangeably herein to refer to the end of an amino acid chain (protein or polypeptide), which is terminated by a free carboxyl group (—COOH). A "non-native" amino acid sequence is any amino acid that is not a naturally occurring amino acid sequence of a GPCR in a naturally occurring position. Thus, the non-native amino acid sequence can be naturally found in a GPCR, but located at a non-native position within the GPCR protein. In one embodiment, the non-native amino acid sequence facilitates introduction of the synthetic phosphopeptide at the C-terminus of the GPCR. The specific non-native amino acid sequence that is present in the chimeric GPCR will depend upon the method by which the synthetic phosphopeptide is introduced into the GPCR C-terminus (discussed further herein). In one embodiment, the non-native amino acid sequence may comprise all or a portion of a recognition sequence (or recognition site) for an enzyme that catalyzes ligation of the phosphopeptide to the GPCR. A number of enzymes that catalyze protein or peptide ligation by acting on specific protein recognition sequences are known in the art and described herein. The chimeric GPCR may comprise any size portion of any suitable enzyme recognition sequence or site, including the entire recognition sequence. In one embodiment, the chimeric GPCR comprises the amino acid sequence LPETGGG (SEQ ID NO: 1), which comprises a portion of the recognition sequence for the sortase enzyme (discussed further herein).

A "phosphopeptide," as used herein, is peptide or polypeptide that incorporates a phosphate group as a result of phosphorylation. Any suitable phosphopeptide may be introduced at the C-terminus of the GPCR. In one embodiment, the synthetic phosphopeptide is obtained or derived from a GPCR that differs from the GPCR that is present in the complex described herein. For example, if the complex comprises the β2 adrenergic receptor, then the synthetic phosphopeptide may be obtained or derived from a GPCR other than the β2 adrenergic receptor. In certain embodiments, the synthetic phosphopeptide is derived from the C-terminus of a GPCR. In one embodiment, the synthetic phosphopeptide is derived from the C-terminus of a vasopressin-2-receptor (V₂Rpp). The V₂Rpp peptide has been shown to bind to β-arrestin1 with high affinity and effectively prime β-arrestin1 for interaction with the GPCR TM core (see, e.g., Shukla et al., Nature, 497(7447): 137-141 (2013); and Nobles et al., J. Biol. Chem., 282: 21370-21381 (2007)). In one embodiment, the synthetic phosphopeptide comprises the amino acid sequence ARGRTPPSLGPQ-DESCTTASSSLAKDTSS (SEQ ID NO: 2).

The synthetic phosphopeptide desirably is phosphorylated at at least one amino acid residue. In some embodiments, the synthetic phosphopeptide is phosphorylated at two or more amino acid residues (e.g., 2, 3, 4, 5, 8, 9, 10 or more). The synthetic phosphopeptide may be phosphorylated at any amino acid residue, and it will be appreciated that phosphorylation of any given site on a protein can change the function or localization of that protein. In eukaryotes, protein phosphorylation is most common on serine, threonine, tyrosine, and histidine residues. Protein phosphorylation is described further in, e.g., Marks, F. (ed.), *Protein Phosphorylation*, John Wiley & Sons (2008); and Alberts et al. (eds.), *Molecular Biology of the Cell*, 6$^{th}$ Ed., Garland Science (2014)). In embodiments where the synthetic phosphopeptide comprises the amino acid sequence of SEQ ID NO: 2, the synthetic phosphopeptide is phosphorylated at residues 5 (threonine), 8 (serine), 15 (serine), 17 (threonine), 18 (threonine), 20 (serine), 21 (serine), and 22 (serine) of SEQ ID NO: 2.

The complex further comprises a β-arrestin (βarr) protein bound to the C-terminus of the GPCR. The term "arrestin," as used herein, encompasses all types of naturally occurring and engineered variants of arrestin, including, but not limited to, visual arrestin (also referred to as Arrestin 1), β-arrestin 1 (also referred to as Arrestin 2), β-arrestin 2 (also referred to as Arrestin 3), X arrestin (also referred to as arrestin 4). Visual arrestin is localized to retinal rods, whereas X arrestin, or arrestin 4, is found in retinal rods and cones. β-arrestin1 and β-arrestin2 (collectively referred to herein as "βarrs") are ubiquitously expressed multifunctional signaling adaptor proteins originally discovered for their role in desensitizing GPCRs (Lefkowitz and Shenoy, Science, 308: 512-517 (2005)). The complex may comprise β-arrestin1 or β-arrestin2. In one embodiment, the complex comprises β-arrestin1 (βarr1).

β-arrestins regulate both GPCR and non-GPCR pathways under normal and pathological conditions, including cancer (Lefkowitz et al., *Mol. Cell.*, 24: 643-652 (2006)). βarrs also have been appreciated as independent signaling units by virtue of their crucial role as both adaptors and scaffolds for an increasing number of signaling pathways (see, e.g., Shukla et al., Trends Biochem Sci 36(9):457-469 (2011); Shenoy, S. K. and R. J. Lefkowitz, Biochem. J., 375(Pt 3): 503-515 (2003); Pierce et al., Nat Rev Mol Cell Biol 3(9):639-650 (2002); Reiter, E. and R. J. Lefkowitz, Trends Endocrinol Metab 17(4):159-165 (2006); DeWire et al., Annu Rev Physiol 69:483-510 (2007); Peterson, Y. K. and Luttrell, L. M., Pharmacol. Rev., 69(3): 256-297 (2017); and Cahill et al., supra).

With respect to binding, it is believed that arrestins make initial contact with phosphorylated receptors via adjacent lysines in the amino terminus (Vishnivetskiy et al., *J. Biol. Chem.*, 275: 41049-41057 (2000)). Biochemical data suggests that this interaction perturbs the three-element interaction, guides phosphorylated receptors to the polar core, allows the negatively charged phosphate from the receptor to interact with positively charge Arg169 (in β-arrestin1), and ultimately causes release of the C-terminal tail from the polar core (Palczewski et al., J. Biol. Chem., 266: 15334-15339 (1991); Gurevich et al., J. Biol. Chem., 273: 15501-15506 (1998); Vishnivetskiy et al., *J. Biol. Chem.*, 275: 41049-41057 (2000); Gurevich and Gurevich, *Trends Pharmacol. Sci.*, 25: 105-111 (2004)). This leads to the disruption of the basal state and subsequent conformational rearrangement of arrestin. Studies monitoring arrestin conformational changes in live cells, along with other biochemical data, suggest that the arrestin amino terminus and C-terminal tail move closer upon binding to an activated receptor (Xiao et al., J. Biol. Chem., 279: 55744-55753 (2004); and Charest et al., EMBO Reports, 6: 334-340 (2005)). This conformational rearrangement enhances arrestin interaction with receptors and is also thought to expose binding motifs that interact with other proteins such as clathrin and AP2 (Moore et al., Annu Rev Physiol., 69: 451-482 (2007)).

In some embodiments, the complex further comprises an antigen-binding fragment of an antibody (Fab) that specifically binds to the complex. The inclusion of a Fab in the complex is believed to stabilize the interaction of β-arrestin1 with the phosphorylated C terminus of the chimeric GPCR. Any suitable Fab may be used to stabilize the receptor complex conformation. In one embodiment, the Fab is conformationally-selective synthetic antibody fragment, referred to as Fab30, that recognizes the phosphopeptide-activated state of β-arrestin1 (Shukla et al., Nature, 497 (7447): 137-141 (2013)). In some embodiments, the complex further comprises an antigen-binding fragment of a nanobody, a variable domain of a single chain antibody (e.g, from camelids) (Cahill T J, 3rd, et al. (2017) Proc Natl Acad Sci USA 114(10):2562-2567).

The complex may be immobilized on a solid support. The solid support may be any suitable surface in planar or non-planar conformation, such as, for example, a surface of a microfluidic chip, an interior surface of a chamber, a bead, an exterior surface of a bead, an interior and/or exterior surface of a porous bead, a particle, a microparticle, an electrode, a slide (e.g., a glass slide), or a multiwell (e.g., a 96-well) plate.

The disclosure also provides an in vitro method for producing the above-described complex. The method comprises (a) enzymatically ligating a synthetic phosphopeptide to the C-terminus of a purified GPCR to produce a phosphorylated chimeric GPCR comprising the amino acid sequence of SEQ ID NO: 1 located within the C-terminus of the GPCR, and (b) contacting the phosphorylated GPCR with purified β-arrestin (βarr) protein, whereupon the purified β-arrestin (βarr) protein binds to the C-terminus of the phosphorylated chimeric GPCR and forms a complex comprising the chimeric GPCR and the βarr protein. Descriptions of the chimeric GPCR, synthetic phosphopeptide, and βarr set forth above in connection with other embodiments of the complex also are applicable to those same aspects of the aforesaid method.

The GPCR and βarr are "purified" in that each is removed from its natural environment, along with any foreign or contaminating elements. Methods for protein isolation and purification are well known in the art, and any such method may be used to purify GPCRs and βarr in accordance with the present disclosure. Protein purification processes typically begin with protein extraction from cells, followed by precipitation, solubilization, and centrifugation. Downstream methods for protein purification include, but are not limited to, size exclusion chromatography, ion exchange chromatography, affinity chromatography (e.g., immunoaffinity chromatography), metal binding, high performance liquid chromatography, reversed phase chromatography, ultrafiltration, and electrophoresis. In one embodiment, the GPCR and/or βarr may be solubilized using a detergent (e.g., dodecyl maltoside (DDM) or maltose neopentyl glycol (MNG)) and purified using affinity chromatography (see, e.g., Kobilka, B. K., Anal. Biochem., 231(1): 269-271 (1995)). Protein purification methods are further described in, e.g., GE Healthcare, Strategies for Protein Purification (available at www.sigmaaldrich.com/content/dam/sigma-aldrich/docs/Sigma-Aldrich/General_Information/1/ge-strategies-for-protein-purification.pdf); and Scopes, R. K. (ed.), Protein Purification: Principles and Practice, Springer Advanced Texts in Chemistry, 3rd Ed., (1993); and Burgess, R. R., Deutscher M. P. (eds.), Guide to Protein Purification, $2^{nd}$ Ed., Methods in Enzymology, Volume 436, Academic Press (2009))

The synthetic phosphopeptide may be ligated to the C-terminus of the GPCR using any suitable method known in the art for protein tagging or conjugation. Such methods include, for example, enzyme-mediated ligation, chemical ligation, protein splicing, and expressed protein ligation (see, e.g., Berrade, L. and J. A. Camarero, Cell. Mol. Life. Sci., 66(24): 3909-3922 (2009); Witte et al., J. Am. Chem. Soc. 119(9): 2114-2118 (1997); and Muir et al., Proc. Natl. Acad. Sci. USA 95(12): 6705-6710 (1998)). In one embodiment, the synthetic phosphopeptide is added to the C-terminus of the GPCR by enzyme-mediated ligation. Enzymatic strategies for coupling peptides or polypeptides are known in the art and include the use of natural ligases such as sortase, butelase, peptiligase, subtiligase, streptoligase, and omniligase (see, e.g., Schmidt et al., Curr Opin Chem Biol., 38: 1-7 (2017)). Enzymatic strategies using ligases such as sortase, butelase, peptiligase or omniligase generally exhibit greater chemoselectivity as compared to chemical ligation methods. Any suitable enzyme may be used to ligate the synthetic phosphopeptide to the GPCR C-terminus, including, but not limited to, sortase, butelase, or peptiligase.

In one embodiment, ligation of the phosphopeptide to the C-terminus of the purified GPCR is catalyzed by a sortase enzyme (also referred to in the art as "sortagging"). In another embodiment, the sortase enzyme is obtained from a prokaryote. Sortase catalyzes a transpeptidation reaction which typically involves pairing of sortase A from Staphylococcus aureus (SrtA$_{staph}$) with an LPXTG (SEQ ID NO: 4)-containing substrate. In the presence of Ca2+, the active site cysteine of SrtA$_{staph}$ cleaves between threonine and glycine to generate a thioester-linked acyl enzyme intermediate. This intermediate is then intercepted by an aminoglycine nucleophile, resulting in the site-specific ligation of the acyl donor and acceptor. Sortagging has been used has been used to introduce several types of common modifications into proteins, including lipids (Antos et al., J Am Chem Soc 130(48): 16338-16343 (2008)) and glycans (Samantaray et al., J Am Chem Soc 130(7): 2132-2133 (2008)). For example, sortagging has been used to generate of camelid-derived antibody fragment conjugates for the treatment of B-cell lymphoma, the installation of nonisotopically labeled protein domains to facilitate NMR analysis of proteins with limited solubility, the construction of immuno-PET reagents for non-invasive cancer imaging, and the preparation of multifunctional protein nanoparticles (see, e.g., Fang et al., Angew Chem Int Ed Engl, 55: 2416-2420 (2016); Amer et al., J. Biomol. NMR, 64: 197-205 (2016); Rashidian et al., ACS Cent. Sci., 1: 142-147 (2015); Chen et al., Chem. Commun., 51: 12107-12110 (2015); and Antos et al., supra).

In one embodiment, the sortase enzyme may be a wild-type sortase enzyme obtained from any suitable species, including, for example, Staphylococcus aureus (SrtA$_{staph}$), Streptococcous pyogenes (SrtA$_{strep}$), and Lactobacillus plantarum (SrtA$_{plant}$). Sortase A from Streptococcus pyogenes (SrtA$_{strep}$), which is Ca2+-independent, can recognize an LPXTA (SEQ ID NO: 5) substrate in addition to LPXTG (SEQ ID NO: 4), and accommodates N-terminal alanine residues as acyl acceptors. SrtA$_{plant}$ has been shown to catalyze transpeptidations involving non-amino acid primary amine nucleophiles and model proteins possessing LAATGWM (SEQ ID NO: 6), LPKTGDD (SEQ ID NO: 7), and LPQTSEQ (SEQ ID NO: 8) sequences (Matsumoto et al., Biotechnol. J., 7: 642-648 (2012); and Antos et al., supra). In one embodiment, the ligation is catalyzed by a wild-type SrtA$_{staph}$ enzyme, and the GPCR comprises a suitable recognition sequence for SrtA$_{staph}$. For example, the purified GPCR may comprise the amino acid sequence LPETGGH (SEQ ID NO: 3).

While the majority of sortagging applications utilize the wilt-type SrtA$_{staph}$ enzyme, in some applications SrtA$_{staph}$ suffers from poor reaction rates and a dependency on a CA2+ cofactor. Thus, in some embodiments, the sortase enzyme may be a sortase enzyme that has engineered to improve performance. In this regard, a number of sortase variants with improved performance have been generated using directed evolution methods, including the pentamutant P94R/D160N/D165A/K190E/K196T (Chen et al., *Proc. Natl. Acad. Sci. USA,* 108: 11399-11404 (2011) and heptamutants which add either E105K/E108A or E105K/E108Q mutation to the aforementioned pentamutant (see, e.g., Hirakawa et al., Biotechnol., J., 10: 1487-1492 (2015); Witte et al., Nat. Protoc., 10: 508-516 (2015); and Wuethrich et al., PLoS ONE, 9: e109883 (2014)). Sortase activity also may be improved by alternating the sortase recognition site on a particular substrate. Thus, the chimeric GPCR may comprise an amino acid sequence other than SEQ ID NO: 3 that is recognized by a wild-type or variant sortase enzyme. In this regard, for example, sortase activity has been observed with the alternate substrates IPKTG (SEQ ID NO: 9), MPXTG (SEQ ID NO: 10), LAETG (SEQ ID NO: 11), LPXAG (SEQ ID NO: 12), LPESG (SEQ ID NO: 13), LPELG (SEQ ID NO: 14), and LPEVG (SEQ ID NO: 15) (Bellucci et al., Angew Chem Int Ed Engl, 52: 3703-3708 (2013); Piotukh et al., J Am Chem Soc, 133: 17536-17539 (2011); and Kruger et al., Biochemistry, 43: 1541-1551 (2004)). Sortase enzyme variants and alternate recognition sequences that may be used in the context of the present disclosure are further described in, e.g., Antos et al., supra.

The in vitro method of producing the aforementioned complex further comprises contacting the phosphorylated chimeric GPCR with purified β-arrestin (βarr) protein, whereupon the purified β-arrestin (βarr) protein binds to the C-terminus of the phosphorylated chimeric GPCR and forms a complex comprising the chimeric GPCR and the βarr protein. The term "contacting," as used herein, refers to any type of combining action which brings the chimeric GPCR into sufficiently close proximity with the purified β-arrestin (βarr) such that a binding interaction will occur. Contacting may be achieved in a variety of different ways, including directly combining the chimeric GPCR with a purified βarr, exposing the chimeric GPCR to a purified βarr by introducing the purified βarr in close proximity to the GPCR, and the like.

In general, the GPCR would be reconstituted into an environment to mimic a cell membrane prior to complex formation, in order to assess activity of the complex. Thus, in some embodiments, the GPCR is reconstituted in high density lipoparticles (HDLs), as described in Staus et al., Nature, 535(7612): 448-452 (2016). Alternatively, the GPCR may be stabilized in other formats, such as, for example, detergent, bicelles, and/or vesicles (see e.g., Shen et al., Int. J. Mol. Sci., 14: 1589-1607 (2013); Goddard et al., Methods Enzymol., 556: 405-424 (2015); and Serebryany et al., Biochim. Biohphys. Acta (BBA), 1818(2): 225-233 (2012)).

2. Screening Methods

The present disclosure provides methods for using the above-described complex to identify ligands which bind to the chimeric GPCR and act as agonists or antagonists of G protein-mediated signaling, especially ligands that are biased for βarr signal transduction. Thus, in certain aspects, the disclosure provides a method for selecting a modulator of a GPCR, such as a biased ligand for a GPCR, which comprises contacting the above-described complex with one or more compounds under conditions to allow for binding of the one or more compounds to the chimeric GPCR and measurement of an activity of the one or more compounds at the chimeric GPCR, and selecting at least one compound that displays the activity, or a change in an activity compared to a reference activity measurement, at the chimeric GPCR. Descriptions of the chimeric GPCR, synthetic phosphopeptide, and βarr set forth above in connection with other embodiments of the disclosure also are applicable to those same aspects of the aforesaid methods. In some embodiments, highly diverse DNA-encoded small molecule libraries may be screened for their ability to bind purified homogenously phosphorylated chimeric GPCRs in complex with β-arrestin using affinity based selection strategies, so as to enable identification of small molecules that bind to GPCRs and preferentially promote β-arrestin coupling over G-protein, or vice versa. Screening methods using GPCR G-protein complexes and/or GPCR alone may performed in parallel or in series to further isolate ligands with desired pharmacological properties, as described further herein.

The term "modulator," as used herein, refers to any substance which alters or changes a characteristic of a GPCR receptor complex and/or a GPCR signaling pathway. For example, a modulator may be a substance which changes the conformation of a GPCR itself, or the interaction of a GPCR with βarr, G protein, or GPCR kinase. Alternatively, a modulator may be a substance which alters the signaling activity of a particular GPCR, either positively or negatively. In some embodiments, a modulator is a ligand for the chimeric GPCR. The term "ligand," as used herein, refers to a substance that forms a complex with a larger biomolecule to exert a biological response. In the context of GPCRs, a ligand is any substance that binds to the GPCR and initiates or produces a signal, inhibits the initiation or production of a signal, or affects the binding of other molecules with these characteristics. A "biased ligand" is a ligand that selectively confers activity in one signaling pathway over another. For example, with regard to GPCRs specifically, a biased ligand may have a relative efficacy for activating a G-protein-coupled receptor function (e.g., signaling) that is greater than its relative efficacy for stimulating β-arrestin function (e.g., recruitment and/or signaling), or vice versa. This type of ligand selectivity also is referred to as "biased agonism" or "functional selectivity" (see, e.g., Rankovic et al., Bioorg. Med. Chem. Lett., 26(2): 241-250 (2016)). Biased ligands for GPCRs are further described in, e.g., International Patent Application Publication WO 2008/021552.

The one or more compounds (e.g., modulators or ligands) may be any suitable compound that is capable of binding to a receptor (e.g., a GPCR). For example, the compound may be a small molecule, a protein, a peptide, or a nucleic acid molecule. The term "small molecule," as used herein, refers to a low molecular weight (generally less than 900 daltons) non-peptide organic compound that may regulate a biological process. Small molecules include, but are not limited to, lipids, monosaccharides, and secondary messengers (e.g., cyclic AMP, cyclic GMP). Small molecules have been in a variety of applications, such as, for example, agonists or antagonists of GPCRs, enzyme inhibitors, nuclear receptor ligands, and ion channel modulators. Indeed, many commonly used drugs are small molecules because, unlike peptides and proteins, they can be designed to be metabolically stable and orally active. As such, the small molecule may be a therapeutic agent, or a compound from which a therapeutic agent is derived (e.g., a "lead" compound). By "therapeutic agent" is meant any agent (e.g., drug), regimen, or strategy that may ameliorate a particular disease condition.

A "peptide" is a compound comprised of two or more amino acids linked by one or more peptide bonds, which link the amino group of one amino acid to a carboxyl group of the other. A "polypeptide" is a polymer comprised of several (e.g., at least 10) amino acids joined by peptide bonds. A "protein" is a compound composed of one or more polypeptide chains with a mass of at least about 10 kilodaltons (kD). The terms "nucleic acid sequence" and "nucleic acid molecule" are synonymous and refer to a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

In one embodiment, the disclosure provides a method for selecting a modulator of a G protein-coupled receptor (GPCR), which method comprises (i) contacting the above-described complex with one or more compounds under conditions to allow for measurement of an activity of the one or more compounds at the chimeric GPCR, (ii) measuring the presence or absence of activity of the one or more compounds, and (iii) selecting at least one compound that displays the activity at the chimeric GPCR. The activity measured by the aforementioned method may be any suitable activity associated with ligand-receptor binding, but typically is a binding activity (e.g., the degree to which a compound binds or does not bind to the chimeric GPCR) or functional activity.

Binding activity of a compound or ligand to a receptor (e.g., as GPCR) may be measured using a variety of suitable methods known in the art. Such methods include, for example, radioactive techniques (e.g., radioligand binding assays, filtration techniques combined with radioactivity counting, scintillation proximity analysis and autoradiography for radioactive ligands, and time-resolved fluorescence resonance energy transfer), and non-radioactive techniques (e.g., fluorescence polarization, fluorescence resonance energy transfer, and surface plasmon resonance). Receptor binding assays are described in detail in, for example, de Jong et al., Journal of Chromatography B, 829(1-2): 1-25 (2005); and Davenport, A. R. (ed.), Receptor Binding Techniques, $3^{rd}$ Ed., Methods in Molecular Biology, Book 897, Human Press (2012).

One of ordinary skill in the art will appreciate that GPCRs regulate complex and multifaceted signaling networks in cells. Indeed, as the receptors for hormones, neurotransmitters, ions, photons and other stimuli, GPCRs are among the essential nodes of communication between the internal and external environments of cells. The classical role of GPCRs is to couple the binding of agonists to the activation of specific heterotrimeric G proteins, leading to the modulation of downstream effector proteins. Thus, a "functional activity" of a GPCR encompasses a wide variety of signaling outcomes which may result from a compound or ligand binding to the chimeric GPCR of the complex described herein.

In one embodiment, the methods described herein may be used to identify an orthosteric GPCR ligand. The term "orthosteric ligand," as used herein, refers to a molecule or compound that binds to the extracellular site of a GPCR where an endogenous ligand binds (e.g., epinephrine for adrenergic receptors) (also referred to as an "orthosteric-binding pocket"). Orthosteric ligands may be identified by performing the methods described herein in the presence of the above-described complex and in the absence of a GPCR agonist. Orthosteric ligands identified by the disclosed methods may exhibit different types of GPCR signaling activity, including, but not limited to, antagonism, balanced antagonism, β-arrestin biased agonism, G-protein biased agonism, inverse agonism, and neutral antagonism. The term "antagonist" encompasses small molecules that bind to an orthosteric site but stabilize an inactive receptor state. Antagonistic ligands may compete with agonist binding and inhibit activation of G protein and β-arrestin in cellular assays. The term "balanced agonist" encompasses small molecules that bind to an orthosteric site and stabilize an unbiased active receptor state(s). Balanced agonistic ligands may proportionally induce activation of G protein and β-arrestin in cellular assays to a similar extent as an endogenous ligand. The term "β-arrestin biased agonist" encompasses small molecules that bind to an orthosteric site and stabilize specific active receptor states that preferentially induce coupling to β-arrestin over G-protein. β-arrestin biased agonist ligands may disproportionally induce β-arrestin and G-protein activation in cellular assays, where the former is greater than the latter. The term "G biased agonist" encompasses small molecules that bind to an orthosteric site and stabilize specific active receptor states that preferentially induce coupling to G-protein over β-arrestin. Such ligands may disproportionally induce G-protein and β-arrestin in cellular assays, where the former is greater than the latter. The term "inverse agonist" encompasses small molecules that binds to the same site as an agonist but induce a pharmacological response opposite to that agonist. The term "neutral antagonist" encompasses small molecules that exhibit no activity in the absence of an agonist or inverse agonist but can block the activity of either.

In other embodiments, the methods described herein may be used to identify an allosteric GPCR ligand. The term "allosteric ligand," as used herein, refers to a molecule or compound that binds to a site of a GPCR other than the endogenous ligand binding site. Allosteric ligands themselves rarely induce effects on GPCR function, but rather modify the properties of an orthosteric ligand, such as by increasing or decreasing its potency or efficacy. Allosteric ligands may be identified by performing the methods described herein in the presence of the above-described complex and a GPCR agonist. Allosteric ligands identified by the disclosed methods may exhibit different types of GPCR signaling activity, including, but not limited to negative allosteric modulation (NAM), balanced positive allosteric modulations (PAM), β-arrestin biased positive allosteric modulation, and G biased positive allosteric modulation. The term "negative allosteric modulator" encompasses small molecules that bind to an allosteric site that stabilizes an inactive receptor state. NAM ligands may decrease the affinity of an orthosteric ligand and reduce activation of G protein and β-arrestin in cellular assays proportionally (a balanced NAM) or disproportionally (a biased NAM). The term "balanced positive allosteric modulator (PAM)" encompasses small molecules that bind to an allosteric binding site and enhance orthosteric ligand affinity, while the balanced signaling properties of the orthosteric ligand are maintained. PAM ligands may proportionally potentiate activation of G protein or β-arrestin by the orthosteric ligand in cellular assays. The term "β-arrestin biased positive allosteric modulator" encompasses small molecules that bind to an allosteric binding site which convert a balanced orthosteric agonist into a β-arrestin biased ligand. Such allosteric ligands may change the balanced signaling properties of an orthosteric ligand in cellular assays, such that β-arrestin activation is greater than G-protein activation. The term "G biased positive allosteric modulator" encompasses small molecules that bind to an allosteric binding site which convert a balanced orthosteric agonist into a G-biased ligand. Such allosteric ligands may change the balanced signaling properties of the orthosteric ligand in cellular assays, such that G-protein activation is greater than β-arrestin activation.

Following identification of at least one compound that displays an activity at the chimeric GPCR, the method for selecting a modulator of a GPCR may further comprise measuring a reference activity at (a) an equivalent chimeric GPCR without C-terminal phosphorylation, (b) an equivalent chimeric GPCR in the absence of β-arrestin, (c) an equivalent chimeric GPCR in the presence of G protein, and/or (d) an equivalent GPCR with a native C-terminus; and selecting a compound that exhibits a difference in the activity at the chimeric GPCR compared to the reference activity. The "reference activity" may be any suitable GPCR activity described herein, e.g., binding activity or functional activity (e.g., signaling activity). In embodiments where the reference activity is binding activity, the binding activity may be measured using any of the methods disclosed herein or known in the art. When the reference activity is a functional activity, the functional activity of the chimeric GPCR itself, β-arrestin, and/or G protein may be assessed, depending on the configuration of the complex (i.e., absence of β-arrestin or presence of G protein). In this regard, G protein activity mediated by a GPCR can be measured using any of a wide variety of assays, including those well known in the art. For example, G protein activity can be assayed by determining the level of calcium, cAMP, diacylglycerol, or inositol triphosphate in the presence and absence of a candidate modulator or ligand. G protein activity can also be assayed, for example, by determining phosphatidylinositol turnover, GTP-γ-S loading, adenylate cyclase activity, GTP hydrolysis, and the like, in the presence and absence of a candidate modulator or ligand (see, e.g., Kostenis, Curr. Pharm. Res. 12(14): 1703-1715 (2006)). Similarly, β-arrestin function mediated by a GPCR in response to a candidate modulator or ligand can be measured using any of a variety of assays. For example, β-arrestin function recruitment to the GPCR or GPCR internalization can be assayed in the presence and absence of a candidate modulator or ligand. In other embodiments, the β-arrestin function in the presence and absence of a candidate modulator or ligand may be measured using by resonance energy transfer, bimolecular fluorescence, enzyme complementation, visual translocation, co-immunoprecipitation, cell fractionation, or assaying interaction of β-arrestin with a naturally occurring binding partner (see, e.g., Violin et al, Trends Pharmacol. Sci. 28(8):416-427 (2007); and Carter et al, J. Pharm. Exp. Ther. 2:839-848 (2005)).

In accordance with the disclosed method for selecting a modulator of a GPCR, the difference in activity may be an enhancement (e.g., an increase or an improvement) in the activity at the chimeric GPCR compared to the reference activity or a decrease in the activity at the chimeric GPCR compared to the reference activity. When the difference in activity is an enhancement in the activity, the enhancement may be greater than or less than the enhancement in the activity measured for a reference ligand. The term "reference ligand," as used herein, refers to a ligand against which the activity of a candidate modulator compound or ligand is measured. In one embodiment, the reference ligand may be an endogenous ligand for the GPCR (wherein more than one endogenous ligand for the GPCR exists, the reference ligand may be the endogenous ligand of highest potency) or an exogenous ligand for the GPCR. For example, a reference ligand for the angiotensin II type 1 receptor is the endogenous ligand, angiotensin II, while a reference ligand for the $\beta_2AR$ may be the exogenous ligand isoproterenol. When the difference in the activity is a decrease in the activity at the chimeric GPCR compared to the reference activity, the decrease may be greater or less than the decrease in the activity measured for a reference ligand.

Enhanced activity for a test compound at the chimeric GPCR compared to an equivalent chimeric GPCR without C-terminal phosphorylation or an equivalent chimeric GPCR in the absence of β-arrestin indicates that the test compound couples through β-arrestin. A greater relative enhancement in activity for the test compound compared to the β-arrestin enhancement of a reference ligand (e.g., endogenous ligand) may indicate that the test compound has β-arrestin biased activity relative to the reference ligand. A lesser relative enhancement in activity for the test compound compared to the β-arrestin enhancement of a reference ligand may indicate the absence of β-arrestin biased activity relative to the reference ligand. Such a test compound may be G biased rather than β-arrestin biased.

Decreased activity for a test compound at the chimeric GPCR compared to an equivalent chimeric GPCR without C-terminal phosphorylation or an equivalent chimeric GPCR in the absence of β-arrestin indicates that the test compound negatively couples through β-arrestin.

Comparison of the relative activity of a test compound and reference ligand in the presence and absence of G protein may indicate the degree of β-arrestin biased activity or G biased activity.

The activity may be enhanced or decreased to any suitable degree as compared to the referenced activity. When the enhancement or decrease in activity is greater than the enhancement or decrease in the activity measured for a reference ligand, the enhancement or decrease in activity may be at least about 5% greater than the enhancement or decrease in the activity measured for a reference ligand (e.g., 10%, 20%, 30%, 40%, 50%, 60%, 70%, 80%, 90%, 100%, 200% or higher). In one embodiment, the enhancement or decrease in activity is at least about 25% greater than the enhancement or decrease in the activity measured for a reference ligand (e.g., 35%, 45%, 55%, 65%, 75%, 85%, 95%, 125% or higher). In other embodiments, the enhancement or decrease in activity is at least about 50% greater than the enhancement or decrease in the activity measured for a reference ligand, or at least about 100% greater than the enhancement or decrease in the activity measured for a reference ligand.

Similarly, when the enhancement or decrease in activity is less than the enhancement or decrease in the activity measured for a reference ligand, the enhancement or decrease in activity may be at least about 5% less than the enhancement or decrease in the activity measured for a reference ligand (e.g., 10%, 20%, 30%, 40%, 50%, 60%, 70%, 80%, 90%, 100%, 200% or higher). In one embodiment, the enhancement or decrease in activity is at least about 25% less than the enhancement or decrease in the activity measured for a reference ligand (e.g., 35%, 45%, 55%, 65%, 75%, 85%, 95%, 125% or higher). In other embodiments, the enhancement or decrease in activity is at least about 50% less than the enhancement or decrease in the activity measured for a reference ligand, or at least about 100% less than the enhancement or decrease in the activity measured for a reference ligand.

In another embodiment, following identification of at least one compound that displays an activity at the chimeric GPCR, the method for selecting a modulator of a GPCR may further comprise measuring a reference activity at (a) an equivalent chimeric GPCR without C-terminal phosphorylation, (b) an equivalent chimeric GPCR in the absence of β-arrestin, (c) an equivalent chimeric GPCR in the presence of G protein, and/or (d) an equivalent GPCR with a native C-terminus, and selecting a compound that exhibits substantially no difference in the activity at the chimeric GPCR compared to its reference activity. In this manner, the selected compound would display an activity that is independent of β-arrestin binding to the chimeric GPCR. The compound exhibits "substantially no difference" in activity compared to a reference activity if the activity of the selected compound is essentially the same as the reference activity, or if the activity of the selected compound is enhanced or decreased as compared to the reference activity by no more than about 5% (e.g., 4%, 3%, 2%, 1% or less). Substantially no difference in activity for a test compound at the chimeric GPCR compared to an equivalent chimeric GPCR without C-terminal phosphorylation or an equivalent chimeric GPCR in the absence of β-arrestin indicates that the test compound does not couple through β-arrestin.

In embodiments where the disclosed method identifies a biased ligand for a GPCR, the method comprises selecting at least one compound that binds to the chimeric GPCR and activates at least one signaling pathway over one or more other signaling pathways mediated by the chimeric GPCR. In this regard, for example, the compound may preferentially activate a Garr-dependent signaling pathway over a G protein-dependent signaling pathway. Alternatively, the compound may preferentially activate a G protein-dependent signaling pathway over a βarr-dependent signaling pathway over a G protein-dependent signaling pathway. Suitable βarr-dependent signaling pathways include, but are not limited to, Mitogen-Activated Protein Kinase (MAPK) signaling, receptor transactivation, receptor trafficking, protein ubiquitination, transcriptional regulation, GPCR desensitization, and GPCR internalization. In another embodiment, the selected compound may activate a signaling pathway that is different than the signaling pathway activated by a reference ligand (e.g., an endogenous GPCR ligand). Alternatively, the selected compound may activate one of a plurality of signaling pathways activated by a reference ligand (e.g., an endogenous GPCR ligand).

The disclosure further provides a method of identifying a biased ligand for a G protein-coupled receptor (GPCR) which comprises contacting the aforementioned GPCR complex with one or more compounds under conditions to allow for binding of the one or more compounds to the GPCR, and selecting a compound that binds to the GPCR and either (i) exhibits a change in an activity measurement compared to a reference activity measurement for the compound or (ii) exhibits substantially no change in an activity measurement compared to a reference activity measurement for the compound at (a) an equivalent GPCR without C-terminal phosphorylation; (b) an equivalent GPCR in the absence of β-arrestin, (c) an equivalent GPCR in the presence of G protein, and/or (d) an equivalent GPCR with a native C-terminus. Descriptions of the complex, compounds, activity measurements, and reference activity set forth above in connection with other embodiments of the disclosure also are applicable to those same aspects of the aforesaid method of method of identifying a biased ligand for a GPCR. In one embodiment, the change in the activity measurement is an enhancement in the activity measurement, such as an enhancement in the activity measurement for the compound that is greater than the enhancement in the activity measurement for a reference ligand for the GPCR, as described herein. Alternatively, the enhancement in the activity measurement for the compound is less than the enhancement in the activity measurement for a reference ligand for the GPCR, as described herein. In another embodiment, the change in the activity measurement is a decrease in the activity measurement, as described herein. As discussed above, any suitable activity may be measured when identifying a biased ligand for GPCR, such as, for example binding affinity, functional potency, and/or efficacy. In one aspect, the enhancement in the activity measurement may be an allosteric enhancement in the activity measurement. Alternatively, the activity measurement may be an antagonistic activity, such that the compound essentially blocks G protein-mediated signal transduction.

B. β2 Positive Allosteric Modulators

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample, or administration to a subject. Contacting encompasses administration to a solution, cell, tissue, mammal, subject, patient, or human. Further, contacting a cell includes adding an agent to a cell culture.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

As described herein, compounds of the invention can optionally be substituted with one or more substituents, such as are illustrated generally above, or as exemplified by particular classes, subclasses, and species of the invention. As described herein, the variables in formula I encompass specific groups, such as, for example, alkyl and cycloalkyl. As one of ordinary skill in the art will recognize, combinations of substituents envisioned by this invention are those combinations that result in the formation of stable or chemically feasible compounds.

The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" as used herein, means a straight or branched chain saturated hydrocarbon. Representative examples of alkyl include, but are not limited to, methyl, ethyl, npropyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl," or as used herein, means a divalent group derived from a straight or branched chain saturated hydrocarbon. Representative examples of alkylene/alkylenyl include, but are not limited to, —$CH_2$—, —$CH_2CH_2$—, —$CH_2CH_2CH_2$—, —$CH_2CH(CH_3)CH_2$—, and $CH_2CH(CH_3)CH(CH_3)CH_2$—.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1, 1-dimethylethyl, and the like.

The term "cycloalkyl" as used herein, means a monocyclic all-carbon ring containing zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups described herein can be appended to the parent molecular moiety through any substitutable carbon atom.

The terms "heterocycle" or "heterocyclic" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic heterocycle, a fused bicyclic heterocycle, or a spiro heterocycle. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4-, 5-, 6-, 7-, or 8-membered monocyclic heterocycle ring wherein two of the substituents on the same carbon atom form a second ring having 3, 4, 5, 6, 7, or 8 members. Examples of a spiro heterocycle include, but are not limited to, 1,4-dioxa-8-azaspiro[4.5]decanyl, 2-oxa-7-azaspiro[3.5]nonanyl, 2-oxa-6-azaspiro[3.3]heptanyl, and 8-azaspiro[4.5]decane. The monocyclic heterocycle groups of the present invention may contain an alkylene bridge of 1, 2, or 3 carbon atoms, linking two nonadjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic, fused bicyclic, and spiro heterocycle groups are connected to the parent molecular moiety through any substitutable carbon atom or any substitutable nitrogen atom contained within the group.

The term "oxo" as used herein refers to an oxygen atom bonded to the parent molecular moiety. An oxo may be attached to a carbon atom or a sulfur atom by a double bond. Alternatively, an oxo may be attached to a nitrogen atom by a single bond, i.e., an N-oxide.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The above substituents may be abbreviated herein. For example, the abbreviations Me, Et, Ph and Bn represent methyl, ethyl, phenyl and benzyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

In accordance with a convention used in the art, the group:

is used in structural formulae herein to depict the bond that is the point of attachment of the moiety or substituent to the core or backbone structure.

2. Compounds

In one aspect, the present invention provides a compound according to Formula (I), or pharmaceutically acceptable salts thereof, wherein $R^1$, $R^2$, $R^3$, $R^4$, $R^5$, and $X^1$ are as defined herein.

In some embodiments, $R^1$ is phenyl optionally substituted with 1-3 substituents independently selected from the group consisting of $C_{1-6}$alkyl, $C_{1-6}$ haloalkyl, $C_{3-7}$cycloalkyl, halogen, cyano, —OH, —$OC_{1-6}$alkyl, —$OC_{1-6}$ haloalkyl, —$NH_2$, —$NHC_{1-6}$alkyl, —$N(C_{1-6}alkyl)_2$, —$OC_{3-6}$cycloalkyl, —$NHC_{3-6}$cycloalkyl, —$N(C_{1-6}alkyl)(C_{3-6}cycloalkyl)$, and —$N(C_{3-6}cycloalkyl)_2$, wherein optionally two substituents join to form a 5- to 7-membered non-aromatic fused ring containing 1-2 heteroatom groups selected from $NR^{1a}$ and O. In certain embodiments, $R^1$ is phenyl optionally substituted with 1-3 substituents independently selected from the group consisting of $C_{1-6}$alkyl, $C_{1-6}$ haloalkyl, $C_{3-7}$cycloalkyl, halogen, —$OC_{1-6}$alkyl, —$OC_{1-6}$ haloalkyl, or —$OC_{3-6}$cycloalkyl, wherein optionally two substituents join to form a 5- to 7-membered non-aromatic fused ring containing 1-2 oxygen atoms. More particularly, in some embodiments, $R^1$ is

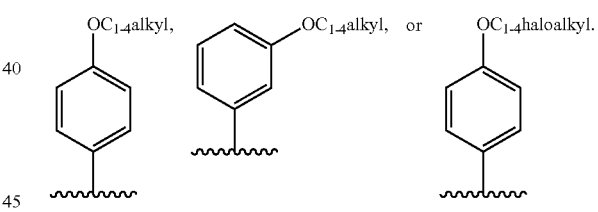

In any of the embodiments described herein are particular embodiments wherein $X^1$ is S.

In any of the embodiments described herein, where $R^2$ and $R^3$ together do not form a ring, are particular embodiments wherein $R^2$ is hydrogen or $C_{1-6}$alkyl.

In any of the embodiments described herein, where $R^2$ and $R^3$ together do not form a ring, are particular embodiments wherein $R^3$ is $C_{1-6}$alkyl, $C_{3-7}$cycloalkyl, or aryl, the aryl being optionally substituted with 1-5 substituents independently selected from the group consisting of $C_{1-6}$alkyl, $C_{1-6}$ haloalkyl, $C_{3-7}$cycloalkyl, halogen, cyano, —OH, —$OC_{1-6}$alkyl, —$OC_{1-6}$ haloalkyl, —$NH_2$, —$NHC_{1-6}$alkyl, —$N(C_{1-6}alkyl)_2$, —$OC_{3-6}$cycloalkyl, —$NHC_{3-6}$cycloalkyl, —$N(C_{1-6}alkyl)(C_{3-6}cycloalkyl)$, and —$N(C_{3-6}cycloalkyl)_2$. In further embodiments, the aryl is optionally substituted with 1-3 substituents independently selected from the group consisting of $C_{1-6}$alkyl, halogen, and $C_{1-6}$ haloalkyl. In still further embodiments, the aryl is selected from

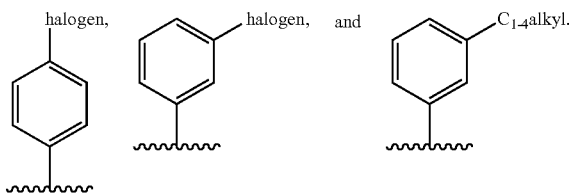

In other embodiments, $R^2$ and $R^3$ together with the nitrogen to which they are attached form a 4- to 8-membered heterocyclic ring optionally containing one additional heteroatom selected from N, O, and S, and being optionally substituted with 1-4 substituents independently selected from the group consisting of $C_{1-6}$alkyl, $C_{1-6}$ haloalkyl, halogen, cyano, —OH, oxo, —NH$_2$, —NHC$_{1-6}$alkyl, and —N(C$_{1-6}$alkyl)$_2$.

In any of the embodiments described herein, where $R^4$ and $R^5$ together do not form a ring, are particular embodiments wherein $R^4$ is hydrogen.

In any of the embodiments described herein, where $R^4$ and $R^5$ together do not form a ring, are particular embodiments wherein $R^5$ is —CHR$^{5a}$R$^{5b}$. In some embodiments, $R^5$ has the following stereochemical configuration:

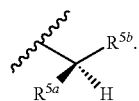

In any of the embodiments described herein, where $R^4$ and $R^5$ together do not form a ring, $R^{5a}$ may be aryl or —C$_{1-3}$alkylene-aryl, the aryl in $R^{5a}$ being optionally substituted with 1-5 substituents independently selected from the group consisting of $C_{1-6}$alkyl, $C_{1-6}$ haloalkyl, $C_{3-7}$cycloalkyl, halogen, cyano, —OH, —OC$_{1-6}$alkyl, —OC$_{1-6}$ haloalkyl, —NH$_2$, —NHC$_{1-6}$alkyl, —N(C$_{1-6}$alkyl)$_2$, —OC$_{3-6}$cycloalkyl, —NHC$_{3-6}$cycloalkyl, —N(C$_{1-6}$alkyl)(C$_{3-6}$cycloalkyl), and —N(C$_{3-6}$cycloalkyl)$_2$. In some embodiments, $R^{5a}$ may be —C$_{1-3}$alkylene-aryl, wherein the aryl is optionally substituted with the foregoing list of optional substituents. More particularly, $R^{5a}$ may be —CH$_2$-phenyl, the phenyl being optionally substituted with 1-3 substituents independently selected from the group consisting of $C_{1-6}$alkyl, $C_{1-6}$ haloalkyl, $C_{3-7}$cycloalkyl, halogen, cyano, —OH, —OC$_{1-6}$alkyl, —OC$_{1-6}$ haloalkyl, —NH$_2$, —NHC$_{1-6}$alkyl, —N(C$_{1-6}$alkyl)$_2$, —OC$_{3-6}$cycloalkyl, —NHC$_{3-6}$cycloalkyl, —N(C$_{1-6}$alkyl)(C$_{3-6}$cycloalkyl), and —N(C$_{3-6}$cycloalkyl)$_2$. Still more particularly, the phenyl in $R^{5a}$ may be optionally substituted with 1-3 substituents independently selected from the group consisting of $C_{1-6}$alkyl, —OH, and $C_{1-6}$ haloalkyl. Still more particularly, $R^{5a}$ may be

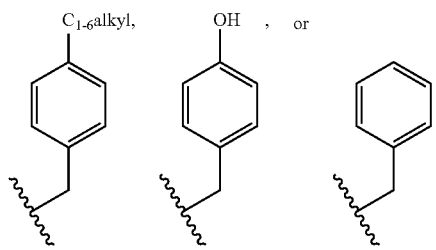

In any of the embodiments described herein where $R^4$ and $R^5$ together do not form a ring, $R^{5b}$ may be $X^2$ or —C$_{1-3}$alkylene-$X^2$. More particularly, $R^{5b}$ may be $X^2$ or —CH$_2$—$X^2$. Still more particularly, $R^{5b}$ may be —CH$_2$—$X^2$.

In other embodiments, $R^4$ and $R^5$ together with the nitrogen to which they are attached form a 4- to 8-membered heterocyclic ring optionally containing one additional heteroatom selected from N, O, and S, and being optionally substituted with 1-4 substituents independently selected from the group consisting of $C_{1-6}$alkyl, $C_{1-6}$ haloalkyl, halogen, cyano, —OH, oxo, —OC$_{1-6}$alkyl, —NH$_2$, —NHC$_{1-6}$alkyl, and —N(C$_{1-6}$alkyl)$_2$.

In any of the embodiments described herein, $X^2$ may be —CN, —C(O)OH, —C(O)OC$_{1-4}$alkyl, —C(O)NH$_2$, —C(O)NHC$_{1-4}$alkyl, —C(O)N(C$_{1-4}$alkyl)$_2$, —SO$_2$NH$_2$, —SO$_2$NHC$_{1-4}$alkyl, or —SO$_2$N(C$_{1-4}$alkyl)$_2$. In particular embodiments, $X^2$ is —C(O)OH or —C(O)NH$_2$.

In certain embodiments of the invention $R^4$ is hydrogen; $R^5$ is —CHR$^{5a}$R$^{5b}$; $R^{5a}$ is —CH$_2$-phenyl, the phenyl being optionally substituted with 1-5 substituents independently selected from the group consisting of $C_{1-6}$alkyl, $C_{1-6}$ haloalkyl, $C_{3-7}$cycloalkyl, halogen, cyano, —OH, —OC$_{1-6}$alkyl, —OC$_{1-6}$ haloalkyl, —NH$_2$, —NHC$_{1-6}$alkyl, —N(C$_{1-6}$alkyl)$_2$, —OC$_{3-6}$cycloalkyl, —NHC$_{3-6}$cycloalkyl, —N(C$_{1-6}$alkyl)(C$_{3-6}$cycloalkyl), and —N(C$_{3-6}$cycloalkyl)$_2$; $R^{5b}$ is —CH$_2$—$X^2$; and $X^2$ is —C(O)OH or —C(O)NH$_2$. In further embodiments according to the foregoing the phenyl at $R^{5a}$ is optionally substituted with 1-3 of the foregoing optional substituents. These embodiments include still further embodiments wherein $R^{5a}$ is

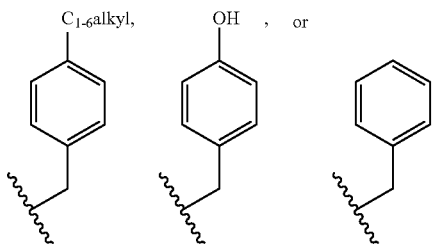

In yet further embodiments included in the foregoing, $R^5$ has the following stereochemistry

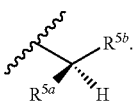

For example, $R^{5a}$ may be

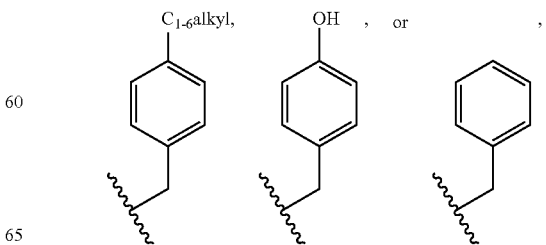

where $R^{5b}$ is —$CH_2$—$X^2$, and $X^2$ is —$C(O)NH_2$, with the following stereochemistry

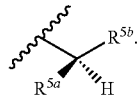

In some embodiments, the compound of formula (I) is selected from (R)—N-(4-amino-1-(4-(tert-butyl)phenyl)-4-oxobutan-2-yl)-5-(N-isopropylsulfamoyl)-2-((4-methoxyphenyl)thio)benzamide;

(R)—N-(4-amino-1-(4-(tert-butyl)phenyl)-4-oxobutan-2-yl)-5-(N-cyclopentylsulfamoyl)-2-((4-methoxyphenyl)thio)benzamide;

(R)—N-(4-amino-1-(4-(tert-butyl)phenyl)-4-oxobutan-2-yl)-5-(N-isopropyl-N-methylsulfamoyl)-2-((4-methoxyphenyl)thio)benzamide;

(R)—N-(4-amino-1-(4-(tert-butyl)phenyl)-4-oxobutan-2-yl)-2-((4-methoxyphenyl)thio)-5-(N-(m-tolyl)sulfamoyl)benzamide;

(R)—N-(4-amino-1-(4-(tert-butyl)phenyl)-4-oxobutan-2-yl)-5-(N-(3-bromophenyl)sulfamoyl)-2-((4-methoxyphenyl)thio)benzamide;

(R)—N-(4-amino-1-(4-(tert-butyl)phenyl)-4-oxobutan-2-yl)-5-(N-(4-fluorophenyl)sulfamoyl)-2-((4-methoxyphenyl)thio)benzamide;

(R)—N-(4-amino-1-(4-(tert-butyl)phenyl)-4-oxobutan-2-yl)-5-(N-(3-fluorophenyl)sulfamoyl)-2-((4-methoxyphenyl)thio)benzamide;

N-isopropyl-4-((4-methoxyphenyl)thio)-N-methyl-3-(piperidine-1-carbonyl)benzenesulfonamide (R)—N-(4-amino-1-(4-(tert-butyl)phenyl)-4-oxobutan-2-yl)-5-(N-isopropyl-N-methylsulfamoyl)-2-((4-(trifluoromethoxy)phenyl)thio)benzamide;

(R)—N-(4-amino-1-(4-(tert-butyl)phenyl)-4-oxobutan-2-yl)-5-(N-isopropyl-N-methylsulfamoyl)-2-((3-methoxyphenyl)thio)benzamide;

(5-(N-isopropyl-N-methylsulfamoyl)-2-((4-methoxyphenyl)thio)benzoyl)-D-tyrosine; and (R)—N-(1-amino-1-oxo-3-phenylpropan-2-yl)-5-(N-isopropyl-N-methylsulfamoyl)-2-((4-methoxyphenyl)thio)benzamide; or a pharmaceutically acceptable salt thereof.

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and 1-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Exemplary tautomeric forms include, for example, the following tautomeric pairs: keto/enol and imine/enamine.

Note that specifically included in the term "isomer" are compounds with one or more isotopic substitutions. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^2H$, can afford certain therapeutic advantages resulting from greater metabolic stability, for example, increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent. In some embodiments, in compounds of formula (I), any hydrogen atom may be deuterium.

A compound described herein can be in the form of a salt, e.g., a pharmaceutically acceptable salt. As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N($C_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl (e.g., phenyl/substituted phenyl) sulfonate.

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C═O) is converted to a diether (R$_2$C(OR)$_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N-0«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—CH$_2$NHC(O)CH$_3$).

3. Methods of Use

Also disclosed are methods of using the disclosed compounds and compositions to treat a disease or condition ameliorated by β$_2$ receptor activation comprising administering to a subject in need thereof a therapeutically effective amount of a compound of formula (I), or a pharmaceutically acceptable salt or pharmaceutical composition thereof.

Compounds of the invention have activity as positive allosteric modulators (PAMs) of the β2 adrenergic receptor and display positive cooperativity with orthosteric agonists, thus enhancing their binding to the receptor and ability to stabilize its active state. The compounds of the invention also exhibit positive cooperativity with G protein and β-arrestin, thus potentiating their stabilization of high-affinity agonist-bound states of the receptor, as well as downstream cAMP production and β-arrestin recruitment to the activated receptor. The positive allosteric activity is specific for the β$_2$AR compared to its closely related sub-type, the β$_1$AR.

Compounds of the invention have several potential benefits as therapeutic drugs to increase specificity as well as to decrease adverse effects for some β2AR-related diseases such as asthma. For example, the compounds have strong specificity for the β2AR over the most closely related subtype β1AR. The compounds also show a ceiling level of activity, which can reduce risks from target-based overdose. As allosteric modulators, compounds of the invention only exert their modulating activity when a β2-agonist of the β2AR is available. Altogether, PAMs of the invention may accomplish fine-tuning of the activity of the β2AR to provide better therapeutic treatments for diseases like asthma, for which β2AR agonists are clinically used. PAMs are expected to allow therapeutic administration of β2AR agonists at lower doses, thereby reducing potential toxicity and/or other off-target effects. In some embodiments, co-administration of a PAM of the invention with a β2AR agonist may provide enhanced therapeutic effect compared to the therapeutic effect achieved by administration of the β2AR agonist alone.

β2 adrenergic receptor agonists are useful for treating diseases or conditions such as obstructive airway disease or bronchospasms (e.g., COPD and asthma), and pre-term labor.

Diseases or conditions that may be treated with compounds and compositions of the invention include an obstructive airway disease, bronchospasms, and pre-term labor.

Particular diseases or conditions include asthma of whatever type, etiology, or pathogenesis; or asthma that is a member selected from the group consisting of atopic asthma; non-atopic asthma; allergic asthma; atopic, bronchial, IgE-mediated asthma; bronchial asthma; essential asthma; true asthma; intrinsic asthma caused by pathophysiologic disturbances; extrinsic asthma caused by environmental factors; essential asthma of unknown or non-apparent cause; nonatopic asthma; bronchitic asthma; emphysematous asthma; exercise-induced asthma; occupational asthma; infective asthma caused by bacterial, fungal, protozoal, or viral infection; non-allergic asthma; incipient asthma; wheezy infant syndrome;

Other diseases or conditions include chronic or acute bronchoconstriction; chronic bronchitis; small airways obstruction; and emphysema.

Still further diseases or conditions include obstructive or inflammatory airways diseases of whatever type, etiology, or pathogenesis; or an obstructive or inflammatory airways disease that is a member selected from the group consisting of chronic obstructive pulmonary disease (COPD); COPD that includes chronic bronchitis, pulmonary emphysema or dyspnea associated therewith; COPD that is characterized by irreversible, progressive airways obstruction; and exacerbation of airways hyper-reactivity consequent to other drug therapy.

In some embodiments, compounds of the invention bind to an allosteric site of the β2 receptor in a subject. In further embodiments, the binding of the compound or its salt to the allosteric site stabilizes an active conformation of the β2 receptor. In still further embodiments, the binding of the compound or its salt potentiates the activity of a β2 agonist, which may be administered in combination with a compound or composition of the invention. In certain embodiments, the compounds of the invention may potentiate tonic receptor activity or receptor activity mediated by endogenous levels of agonist present. In certain embodiments, the compound, its pharmaceutical salt, or composition is administered in combination therapy with a β2 agonist wherein the amount of the compound, pharmaceutical salt, or composition may reduce tolerance to the effects of the β2 receptor agonist compared to the tolerance in a reference subject receiving treatment with the β2 receptor agonist alone.

4. Pharmaceutical Compositions

In another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. In one embodiment, the pharmaceutical composition comprises a therapeutically effective amount of a compound of the present invention or a pharmaceutically acceptable salt thereof and one or more pharmaceutically acceptable carriers or vehicles.

In one aspect, provided is a pharmaceutical composition comprising a compound according to Formula (I), or a tautomer or pharmaceutically acceptable salt thereof, and a pharmaceutically acceptable carrier.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease being treated.

Thus, the compounds and their pharmaceutically acceptable salts may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

The term "parenterally," as used herein, refers to modes of administration which include intravenous, intramuscular, intraperitoneal, intrasternal, subcutaneous and intraarticular injection and infusion.

Carriers for systemic administration may include one or more of diluents, lubricants, binders, disintegrants, colorants, flavors, sweeteners, antioxidants, preservatives, glidants, solvents, suspending agents, wetting agents, surfactants, emulsifying agents and dispersing agents, combinations thereof, and others. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, pills, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The pharmaceutical compositions of the present invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

Aerosol propellants are required where the pharmaceutical composition is to be delivered as an aerosol under significant pressure. Such propellants include, e.g., acceptable fluorochlorohydrocarbons such as dichlorodifluoromethane, dichlorotetrafluoroethane, and trichloromonofluoromethane; nitrogen; or a volatile hydrocarbon such as butane, propane, isobutane or mixtures thereof.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound is in the range of about 100 µg to about 250 mg per kilogram body weight of the subject per day.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

The present compounds, compositions, and methods may be administered as part of a therapeutic regimen along with other treatments appropriate for the particular injury or disease being treated.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

Additional pharmaceutical agents include PDE3 and/or PDE4 inhibitors, 5-lipoxygenase (5-LO) inhibitors; 5-lipoxygenase activating protein (FLAP) antagonists; dual inhibitors of 5-lipoxygenase (5-LO) and antagonists of platelet activating factor (PAF); leukotriene antagonists (LTRAs) including antagonists of LTB4, LTC4, LTD4, and LTE4; β2-adrenoceptor agonists; cromolyn sodium, theophylline and aminophylline; inhaled glucocorticoids, interleukin-5 (IL-5) inhibiting monoclonal antibodies; and antibodies that inhibit binding of IgE to the high-affinity IgE receptor (e.g., omalizumab).

PDE4 inhibitors include roflumilast.

Dual PDE3/PDE4 inhibitors include RPL-554 [9,10-dimethoxy-2(2,4,6-trimethylphenylimino)-3-(N-carbamoyl-2-aminoethyl)-3,4,6,7-tetrahydro-2H-pyrimido[6,1-a]isoquinolin-4-one] and RPL565 [6,7-dihydro-2-(2,6-diisopropylphenoxy)-9,10-dimethoxy-4H-pyrimido[6,1-a]isoquinolin-4-one].

5-LO inhibitors include N-hydroxyureas such as zileuton, ABT-761, fenleuton, Abbott-79175, Abbott-85761, and SB-210661, methoxytetrahydropyrans such as ZD-2138, 2-cyanonaphthlanes/2-cyanoqinolines such as L-739,010 and L-746-530.

FLAP inhibitors include indole-quinolines such as MK-591, MK-886, and BAY x1005.

LTRAs include ablukast, monteluast, ontazolast, and zafirluast.

Representative 5-LO inhibitors, FLAP inhibitors, and LTRAs are disclosed in U.S. Pat. No. 6,894,041, which disclosure is incorporated herein by reference.

β2-adrenoceptor agonists including albuterol, levalbuterol, arformoterol, salbutamol, formoterol, indacaterol, olodaterol, terbutaline, ritodrine, hexoprenaline, metaproterenol, nylidrin, orciprenaline, and salmeterol.

Inhaled glucocorticoids include flunisolide, triamcinolone acetonide, beclomethasone dipropionate, budesonide, ciclesonide, fluticasone furoate, fluticasone propionate, mometasone, and mometasone furoate.

Anticholinergics include glycopyrrolate (e.g., glycopyrronium bromide), ipratropium bromide, aclidinium bromide, tiotropium, and umeclidinium.

Monoclonal antibodies that inhibit IL-5 include benralizumab (an IL-5 receptor inhibitor), mepolizumab (binds IL-5), and reslizumab (binds IL-5).

In another aspect, the disclosure provides a kit. A kit will include a compound of formula (I) as described herein. A kit may also include instructions for use of the compound of formula (I) or at least one active agent. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD, DVD), and the like. As used herein, the term "instructions" can include the address of an internet site that provides the instructions.

In some embodiments, the at least one disclosed compound and the at least one active agent are co-formulated. In some embodiments, the at least one disclosed compound and the at least one active agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may include information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

5. Chemical Synthesis

Compounds of the invention may be prepared as illustrated in the following schemes and examples.

Abbreviations:
Calcd calculated
DCM dichloromethane
DMF N,N-dimethylformamide
DMSO dimethylsulfoxide
EDC 1-(3-dimethylaminopropyl)-3-ethylcarbodiimide methiodide
Et ethyl
ESI-TOF electrospray ionization time-of-flight
EtOAc ethyl acetate
Fmoc fluorenylmethyloxycarbonyl
h hour
HATU 1-[Bis(dimethylamino)methylene]-1H-1,2,3-triazolo[4,5-b]pyridinium 3-oxide hexafluorophosphate
HOAt 1-hydroxy-7-azabenzotriazole
HOBt 1-hydroxybenzotriazole FIRMS high resolution mass spectrometry
Me methyl
MeCN acetonitrile
MeOH methanol
NHS N-hydroxysuccinimide
Ph phenyl
ppm parts per million
psig pounds per square inch
pyr pyridine
rt or r.t. room temperature
TFA trifluoroacetic acid Synthesis and Characterization of Compound 6 and its Derivatives

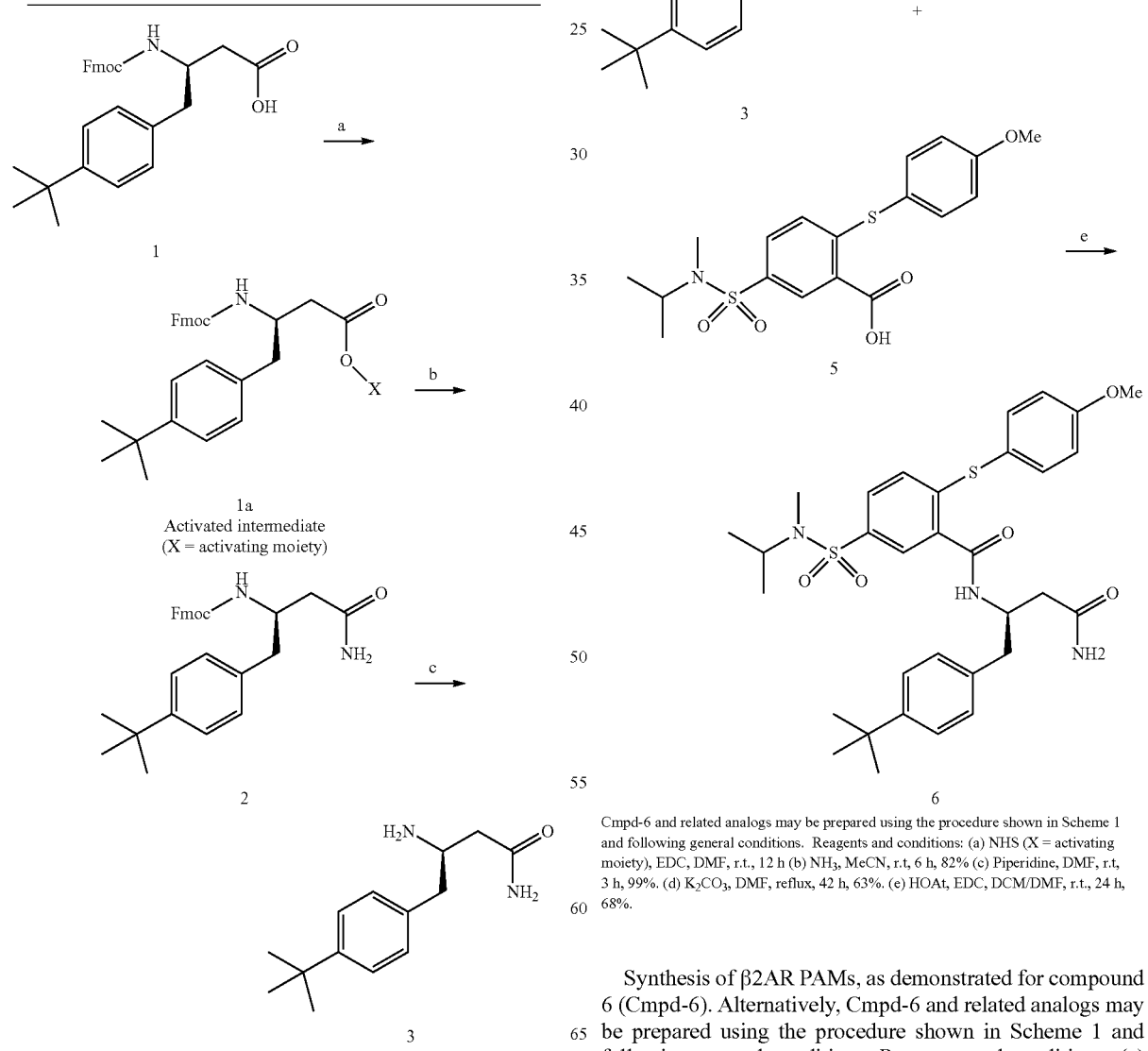

Cmpd-6 and related analogs may be prepared using the procedure shown in Scheme 1 and following general conditions. Reagents and conditions: (a) NHS (X = activating moiety), EDC, DMF, r.t., 12 h (b) NH$_3$, MeCN, r.t, 6 h, 82% (c) Piperidine, DMF, r.t, 3 h, 99%. (d) K$_2$CO$_3$, DMF, reflux, 42 h, 63%. (e) HOAt, EDC, DCM/DMF, r.t., 24 h, 68%.

Synthesis of β2AR PAMs, as demonstrated for compound 6 (Cmpd-6). Alternatively, Cmpd-6 and related analogs may be prepared using the procedure shown in Scheme 1 and following general conditions. Reagents and conditions: (a) HOBt (X=activating moiety), EDC, DCM, r.t., 6 h (b) NH$_3$ solution (7N methanolic ammonia), DCM, r.t, 6 h, 85% (c) Piperidine, DMF, r.t, 3 h, 99%. (d) Ullmann-type reaction i.e., synthesis of symmetric biaryls via copper-catalyzed coupling herein using CuI, L-proline, $K_2CO_3$, DMF, reflux, 24 h, 85%. (e) HATU/Hünig's base (N,N-diisopropylethylamine, DIEA)-assisted amidation: HATU, DIEA, DMF, r.t., 18 h, 75%.

General chemistry: Starting materials for Cmpd-6 and analog synthesis were purchased from Sigma-Aldrich; St. Louis, MO, Thermo Fisher Scientific; Waltham, MA, Enamine; Monmouth Jct., NJ, Chem-Impex; Wood Dale, IL, Combi-Blocks; San Diego, CA, Santa Cruz Biotechnology; Dallas, TX, Toronto Research Chemicals; Toronto, Canada, and TCI America; Portland, OR; and used without further purification.

Silica gel coated with F254 fluorescent indicator on aluminum plates was used for analytical thin layer chromatography (TLC). The course of reactions was followed by visualization under UV (254 nm or 366 nm) and/or using standard staining procedures such as ninhydrin and $KMnO_4$. Compounds may be purified by recrystallization, by manual flash column chromatography (FCC) system using silica gel 60 (SiO2; 230-400 mesh, Merck), or Reveleris® X2 flash chromatography system for purification and Büchi R-300 rotary evaporator Chemical and structural characterization of compounds
$^1H$ NMR and $^{13}C$ NMR spectra may be acquired on a FT-NMR Bruker Avance Ultra Shield Spectrometer at 400.13, commonly in deuterated solvents such as DMSO-$d_6$ and $CDCl_3$.

High-resolution time-of-flight mass spectra (HRMS ESI-TOF) may be performed on a Waters LCT Premier XE (TOF) using electrospray ionization.

Synthesis of (9H-Fluoren-9-yl)methyl(R)-(4-amino-1-(4-(tert-butyl)phenyl)-4-oxobutan-2-yl)-carbamate (2). To an ice-cold stirred solution of Fmoc-(R)-3-amino-4-(4-tert-butylphenyl)butyric acid (250 mg, 0.55 mmol) and N-hydroxysuccinimide (82 mg, 0.71 mmol) in dry DMF (10 mL) are added EDC·HCl (137 mg, 0.71 mmol) under nitrogen atmosphere. The mixture is allowed to reach room temperature and stirred overnight. The reaction mixture is then concentrated under reduced pressure, and then the residue was diluted with EtOAc (150 mL) and washed with water (3×50 mL). The organic phase is dried and concentrated. The crude product 1a is then used for the next step without further purification. Aqueous ammonia solution at 28% (0.77 mL, 11 mmol) is added to a solution of 1a obtained above (305 mg, ~0.55 mmol) in MeCN (7 mL) at room temperature. After stirring at room temperature for 2 h, the solvent and volatiles are removed in vacuo, and the solid residue is suspended in $H_2O$ (80 mL). The resulting mixture is extracted with DCM (3×100 mL), and the combined organic layers are washed with brine (200 mL), dried over $Na_2SO_4$ and concentrated in vacuo. The crude product is purified by flash chromatography (EtOAc/petroleum ether: 1:1) to give 2 (typical yield: 195 mg, 82% yield over two steps) as a white solid. FIRMS (ESI, positive) for $C_{29}H_{33}N_2O_3+$ [M+H]+ calcd 457.2486, found 457.2487.

Synthesis of (R)-3-amino-4-(4-(tert-butyl)phenyl)butanamide (3). To a solution of 2 (167 mg, 0.38 mmol) in DMF (4 mL) is added piperidine (0.8 mL) at rt. After being stirred at rt for 6 h, the mixture is concentrated in vacuo. The crude product is purified by flash chromatography (eluting with 10:1 $CH_2Cl_2$/MeOH and 10:1:0.1 $CH_2Cl_2$/MeOH/$Et_3N$) to afford 3 (typical yield: 89 mg, 99% yield) as white solid. FIRMS (ESI, positive) for $C_{14}H_{23}N_2O+$ [M+H]+ calcd 235.1805, found 235.1806.

Synthesis of 5-(N-Isopropyl-N-methylsulfamoyl)-2-((4-methoxyphenyl)thio)benzoic acid (5). To a solution of 2-fluoro-5-[[methyl(1-methylethyl) amino]sulfonyl]-benzoic acid (550 mg, 2 mmol) in DMF (20 mL) is added $K_2CO_3$ (662 mg, 4.8 mmol), and followed by 4-methoxybenzenethiol (0.25 mL, 2 mmol), and then the mixture is heated at reflux for 42 h. After the reaction is complete, the solvents are removed in vacuo. The crude product is poured into $H_2O$ (200 mL), and acidified with aqueous 2 M HCl to adjust pH to 3-4. The resulting mixture was extracted with DCM (3×150 mL), and the combined organic layers are washed with brine (2×100 mL), dried over $Na_2SO_4$, and concentrated in vacuo. The crude product is purified via flash chromatography ($CH_2Cl_2$/MeOH: 10:1) to afford 5 (typical yield: 500 mg, 63% yield) as a white solid. HRMS (ESI, negative) for $C_{18}H_{20}NO_5S_2-$ [M-H]+ calcd 394.0788, found 394.0787.

Synthesis of (R)—N-(4-Amino-1-(4-(tert-butyl)phenyl)-4-oxobutan-2-yl)-5-(N-isopropyl-N-methylsulfamoyl)-2-((4-methoxyphenyl)thio)benzamide (Compound 6). To a stirred mixture of 3 (77 mg, 0.33 mmol) and 5 (130 mg, 0.33 mmol) in DCM/DMF (10:1 v/v, 10 mL) is added EDC·HCl (62 mg, 0.33 mmol) and HOAt (44 mg, 0.33 mmol), and the mixture is stirred at rt for 24 h. After the solvent is removed in vacuo, the crude product is purified by flash chromatography (EtOAc/petroleum ether, 1:1) to afford 6 (typical yield: 136 mg, 68% yield) as white solid. HRMS (ESI, positive) for $C_{32}H_{41}N_3NaO_5S_2+$ [M+Na]+ calcd 634.2380, found 634.2381.

Synthesis of N-isopropyl-4-((4-methoxyphenyl)thio)-N-methyl-3-(piperidine-1 carbonyl)benzenesulfonamide (Compound A3). The title compound is typically prepared in a manner analogous to compound 6 at step 5. Except in this step in scheme 1, the secondary amine-piperidine (65 mg, 0.6 mmol) with 5 (200 mg, 0.5 mmol) is used instead of 3. The compound is purified as white solid (typical yield: 80%). ESI-MS (positive mode): m/z 463.1729 [M+H]+ and m/z 485.1544 [M+Na]+.

Synthesis of (R)—N-(4-amino-1-(4-(tert-butyl)phenyl)-4-oxobutan-2-yl)-5-(N-isopropyl-N-methylsulfamoyl)-2-((4-(trifluoromethoxy)phenyl)thio)benzamide (Compound A4). The title compound, bearing a 4-$OCF_3$ group instead of a 4-$OCH_3$ is prepared in an analogous manner, except in the fourth step in scheme 1, the intermediate 4-(trifluoromethoxy)benzenethiol (351 mg, 1.8 mmol) with 4 (500 mg, 1.8 mmol) is used instead of 4-methoxybenzenethiol. The compound is purified as white solid (typical yield: 70%). ESI-MS (positive mode): m/z 666.2299 [M+H]+ and m/z 688.2115 [M+Na]+.

Synthesis of (R)—N-(4-amino-1-(4-(tert-butyl)phenyl)-4-oxobutan-2-yl)-5-(N-isopropyl-N-methylsulfamoyl)-2-((3-methoxyphenyl)thio)benzamide (Compound A5). The title compound, bearing a meta-$OCH_3$ instead of a para-$OCH_3$ is prepared in an analogous manner, except in the fourth step in scheme 1, the intermediate 3-methoxybenzenethiol (254 mg, 1.8 mmol) with 4 (500 mg, 1.8 mmol) is used instead of 4-methoxybenzenethiol. The compound is purified as white solid (typical yield: 75%). ESI-MS (positive mode): m/z 612.2562 [M+H]+ and m/z 634.2375 [M+Na]+.

Synthesis of (5-(N-isopropyl-N-methylsulfamoyl)-2-((4-methoxyphenyl)thio)benzoyl)-D-tyrosine (Compound A6). The title compound, bearing a 4-OH on the benzene ring instead of tert-butyl with a carboxyl group on the right end of the molecule was prepared in a manner analogous to Compound 6, except in step 5 of scheme 1, the intermediate D-Tyrosine tert-butyl ester (72 mg, 0.3 mmol) with 5 (100 mg, 0.3 mmol) was used instead of 3. Following trifluoroacetic acid (TFA)-mediated removal of the tert-butyl group (DCM, 2 mL; TFA, 1 mL; 12 h; RT), the product was concentrated in vacuo and purified by flash chromatography using a gradient and mixture of solvents (EtOAc-DCM and DCM-MeOH), to afford the product as white solid (60% yield). ESI-MS (positive mode): m/z 559.1572 [M+H]+ and m/z 581.1375 [M+Na]+.

Synthesis of (R)—N-(1-amino-1-oxo-3-phenylpropan-2-yl)-5-(N-isopropyl-N-methylsulfamoyl)-2-((4-methoxyphenyl)thio)benzamide (Compound A7). The title compound, primarily lacking a tert-butyl group was prepared in a manner analogous to Compound 6, except in step 5 of scheme 1, the intermediate (R)-2-amino-3-phenylpropanamide (78 mg, 0.3 mmol) with 5 (100 mg, 0.3 mmol) was used instead of 3. The compound was purified as white solid (80% yield). ESI-MS (positive mode): m/z 542.1774 [M+H]+ and m/z 564.1581 [M+Na]+.

Synthesis of (R)—N-(4-Amino-1-(4-(tert-butyl)phenyl)-4-oxobutan-2-yl)-5-(N-(3-fluorophenyl)sulfamoyl)-2-((4-methoxyphenyl)thio)benzamide (Compound 43). The title compound, bearing the fluorobenzene moiety instead of isopropyl at the sulfonamide linkage, is prepared in a manner analogous to Compound 6, except step 5 of scheme 1, the intermediate 5-(N-(3-Fluorophenyl)sulfamoyl)-2-((4-methoxyphenyl) thio) benzoic acid (52 mg, 0.12 mmol) with 3 (28 mg, 0.12 mmol) was used instead of 5. The compound is purified as white solid (typical yield: 44 mg, 56%). HRMS (ESI, negative) for $C_{34}H_{37}FN_3O_5S_2+$ [M−H]+ calcd 650.2153, found 650.2153.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

Using procedures analogous to the foregoing schemes and examples, additional compounds of formula (I) may be prepared, including those in FIG. 14G. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

The following examples further illustrate the invention but, of course, should not be construed as in any way limiting its scope.

C. Biological Methods and Evaluation

Molecular Biology: For construction of pcDNA-ZeotetO, an NdeI-XhoI fragment from pACMV-tetO (Reeves P J, et al. (2002) *Proc Natl Acad Sci USA* 99(21):13413-

13418.), which contained tet operator sequences inserted into the CMV promoter, was ligated into the NdeI/XhoI-digested pcDNA3.1-Zeo backbone. All β2-adrenergic receptor (β2AR) constructs were of human origin and contained an N-terminal FLAG-tag and a C-terminal 6× His-tag. For β2AR constructs used in sortase ligations, the sortase consensus site (LPETGHH) was inserted after amino acid 365 (β2AR-LPETGHH). The minimal cysteine β2AR (β2ARΔ4) used in bimane fluorescence experiments and the minimal ICL3 mutant (β2ARΔ238-267) were designed as previously described (Yao X J, et al. (2009) *Proc Natl Acad Sci USA* 106(23):9501-9506., Kumari P, et al. (2016) *Nat Commun* 7:13416.). All β2AR constructs expressed in Sf9 insect cells contained the N187E glycosylation mutation. Human Muscarinic-2 Receptor (M2R) and Mu (µ)-Opioid Receptor (MOR) were cloned into pcDNA-Zeo-tetO with an N-terminal FLAG-tag and C-terminal sortase consensus site followed by a 6× His-tag. To enhance stability and expression, a minimal cysteine (C59A, C125S, C140I, C150V, C242V, C251V, and C269S) and truncated (after amino acid 393) variant of rat βarr1 (βarr1-MC-393) in pGEX4T was generated. The Δ62-77 finger loop deletion and the V70C mutation, corresponding to V74C of visual arrestin (Hanson S M, et al. (2006) *Proc Natl Acad Sci USA* 103(13):4900-4905.), were introduced in pGEX4T-βarr1-MC-393.

β2AR Expression and Purification: With the exception of β2ARΔ238-267, all β2AR constructs were expressed in Sf9 insect cells using the BestBac Baculovirus Expression System (Expression Systems). Cells were infected at a density of 3×10⁶ cells/mL and harvested 60 h thereafter. Receptor was solubilized in n-Dodecyl-β-D-Maltopyranoside (DDM) (Anatrace) and purified using FLAG-M1 and alprenolol-affinity chromatography as previously described (Kobilka B K (1995) *Anal Biochem* 231(1):269-271). β2ARΔ238-267 in pcDNA-Zeo-tetO was transfected into Expi293F cells (Invitrogen) stably integrated with the plasmid pcDNA/TR (Invitrogen) to express the tetracycline repressor (Expi293F-TR). Cells were transfected using Expifectamine (Invitrogen) as described in the manufacturer's protocol with receptor expression being induced 48 h post-transfection with 4 µg/mL doxycycline, 5 mM sodium butyrate, and 1 µM of the β2AR antagonist alprenolol. Cultures were harvested 30-36 h thereafter, and all purification steps conducted at 4° C. with protease inhibitors (benzamidine and leupeptin) unless stated otherwise. Cell pellets were resuspended (10 mL/g wet cell pellet mass) in room temperature lysis buffer (10 mM TRIS, pH 7.4, 2 mM EDTA, 10 mM MgCl2, 5 units/mL benzonase (Sigma) and 2 mg/mL iodoacetamide) with 1 µM alprenolol for 20 min. Membrane was pelleted at 30,000×g for 20 min and resuspended in 10 mL/g original cell pellet mass of solubilization buffer (20 mM HEPES, pH 7.4, 100 mM NaCl, 1% DDM, 0.05% cholesterol hemisuccinate (CHS), 10 mM MgCl2, 5 units/mL benzonase, and 2 mg/mL iodoacetamide) with 1 µM alprenolol. After extensive dounce homogenization, solubilizing membrane was sequentially stirred at room temperature and then 4° C. for 1 h each. Insoluble material was removed by centrifugation at 30,000×g for 30 min, supernatant loaded onto M1-FLAG resin with 2 mM CaCl2 at 1-3 mL/min, and resin washed with 20 column volumes of wash buffer (20 mM HEPES, pH 7.4, 100 mM NaCl, 0.1% DDM, 0.01% CHS, and 2 mM CaCl2). Receptor was eluted in elution buffer (20 mM HEPES, pH 7.4, 100 mM NaCl, 0.1% DDM, 0.01% CHS, 0.2 mg/mL FLAG-peptide, and 5 mM EDTA), and monomeric receptor was collected by size exclusion chromatography on a Superdex 200 Increase column (GE Healthcare Life Sciences).

M2R and MOR Expression and Purification: The M2R and the MOR were expressed in and purified from Expi293F-TR cells as described above with the following modifications. The antagonists atropine (1 µM) and naloxone (1 µM) were included during expression and purification for the M2R and the MOR, respectively. For M2R solubilization, 10% glycerol was added, and NaCl was increased to 750 mM based on previous studies (Kruse A C, et al. (2013) *Nature* 504(7478):101-106). Additionally, M1-FLAG resin was washed with 5 column volumes of high (750 mM) and low (100 mM) NaCl-containing wash buffer at ratios of 4:0, 3:1, 2:2, 1:3, and 0:4, respectively. In addition to DDM, MOR solubilization buffer contained 0.3% 3-[(3-cholamidopropyl) dimethylammonio]-1-propanesulfonate (CHAPS) (Manglik A, et al. (2012) *Nature* 485(7398):321-326).

G protein, βarr1, and Nb80 Purification: Heterotrimeric G protein was purified as previously described (Gregorio G G, et al. (2017) *Nature* 547(7661):68-73). In brief, Trichoplusia ni HighFive insect cells were infected with two viruses made from BestBac baculovirus system, the first expressing both human Gβ1-His6 and Gγ2, and the second Gαi or the short Gαs splice variant. Cells were harvested 48 h post-infection. Heterotrimeric Gs or Gi was purified from solubilized cell membranes using Ni-NTA chromatography and HiTrap Q sepharose anion exchange (GE Healthcare Life Sciences). Purification of βarr1 was conducted as previously described (Nobles K N, et al. (2007) *J Biol Chem* 282(29):21370-21381). In short, GST-βarr1-MC-393 was expressed in BL21(DE3) bacteria, lysed using a microfluidizer, and captured using glutathione sepharose. βArr1 was removed from GST by thrombin digestion and further purified using HiTrap Q sepharose anion exchange. Nb80 was purified as previously described (Staus D P, et al. (2016) *Nature* 535 (7612):448-452).

High-Density Lipoprotein (HDL) Reconstitution: Receptor reconstitution into HDL particles was conducted as described elsewhere (Staus D P, et al. (2016) *Nature* 535 (7612):448-452). In short, DDM-solubilized receptor (2 µM) was incubated for 1 h at 4° C. with 80 µM Apolipoprotein A1 (MSP1D1) and a 3:2 molar ratio of 8 mM phosphatidylcholine (POPC) with phosphatidylglycerol (POPG). Bio-beads (Bio-Rad) were added (0.5 mg/µL reconstitution volume) thereafter and rotated overnight at 4° C. HDL-receptor was isolated from non-receptor-containing HDL particles using M1-FLAG chromatography.

Sortase Ligation Reactions: All sortase reactions were conducted in buffer containing 20 mM HEPES, pH 7.4, 100 mM NaCl, 0.1% DDM, 0.01% CHS, and 5 mM CaCl2. Detergent-solubilized receptor (10 µM) was incubated with GGG-V₂Rpp (GGG-ARGRpTPPpSLGPQDEp-SCpTpTApSpSpSLAKDTSS) (50 µM) (lower-case "p"=phosphorylation) or non-phosphorylated GGG-V2R, and 2 µM SortaseA containing five mutations that increase ligation efficiency, as described previously (Chen I, et al. (2011) *Proc Natl Acad Sci USA* 108(28):11399-11404). Ligations were incubated overnight at 4° C., and unligated receptor (containing C-terminal 6× His-tag) was removed using Talon resin (Invitrogen). Size exclusion chromatography was utilized to specifically isolate monomeric ligated receptor.

Bimane Fluorescence: For bimane labeling of proteins, alprenolol-pure β2AR, β2AR-LPETGGH or ion-exchange-pure βarr1-MC-393 V70C was incubated with 100 µM TCEP at 4° C. for 15 min, then with a 3-fold excess of monobromobimane (Sigma) at 4° C. overnight. An additional 3-fold molar excess of monobromobimane was added the next day, and the reaction was allowed to continue for 1 h at room temperature before quenching with excess L-cysteine. Excess label was removed by size exclusion chromatography. Bimane-labeled βarr1 was concentrated and flash frozen with 15% glycerol. For bimane-labeled receptors, phosphopeptide ligation (β2AR-LPETGGH-bimane) and HDL reconstitution (β2AR-bimane and β2ARpp-bimane) were carried out as described above.

Bimane-labeled β2AR or β2ARpp HDLs were incubated with or without isoproterenol for 15 min at room temperature before the addition of excess transducer. Final concentrations were 250 nM HDL, 10 µM isoproterenol, 500 nM Gs (+5 mM MgCl2), 1 µM βarr1-393 minimal cysteine or βarr1-393 minimal cysteine 462-77 in buffer comprised of 20 mM HEPES, pH 7.4, 100 mM NaCl. The reactions were equilibrated for at least 30 min in black, solid-bottom 96-well microplates before fluorescence emission spectra were collected on a CLARIOstar plate reader (BMG LABTECH) in top-read mode, with excitation at 370 nm (16 nm bandpass) and emission scanning from 400 nm to 600 nm (10 nm bandpass) in 1 nm increments. Reactions were set up in duplicate in each experiment, and wells for background subtraction contained all components except the bimane-labeled HDLs. Experiments were repeated at least three times.

For experiments with βarr1-bimane, HDL-receptors were incubated with ligands (and for β2ARpp, Nb80) for 15 min at room temperature. βArr1-bimane was added to each well, and the reactions were equilibrated for at least 30 min before being read as described above. Final concentrations were 375 nM HDLs, 10 µM ligand, 500 nM Nb80, and 250 nM βarr1-bimane. Reactions were set up in duplicate in each experiment, and wells for background subtraction contained all components except βarr1-bimane. To normalize data, the area under each averaged, background-subtracted curve between 425 nm and 600 nm was calculated (GraphPad Prism), and areas were normalized to the maximum value (M2Rpp plus iperoxo) in each experiment. Experiments were repeated at least three times.

Receptor-Transducer Co-immunoprecipitation: Since β2AR and βarr1 are of similar molecular weight, we used a β2AR construct with T4-lysozyme (T4L) fused to the receptor's N terminus to obtain separation by SDS-PAGE (Zou Y, et al. (2012) *PLoS One* 7(10):e46039). Assay and wash buffer consisted of 20 mM HEPES, pH 7.4, 100 mM NaCl, 0.1% DDM, and 2 mM CaCl2. Unligated or phosphopeptide-ligated FLAG-T4L-β2AR in DDM were mixed with 10 µM isoproterenol and stoichiometric amounts of heterotrimeric G protein or βarr1-MC-393. The antibody fragment Fab30 was added to βarr1 to stabilize the interaction with the phosphorylated receptor C terminus (Shukla A K, et al. (2013) *Nature* 497(7447):137-141). After reactions were incubated at room temperature for 1 h, FLAG-T4L-β2AR was immunoprecipitated using FLAG-M1 resin, and transducers were eluted by the addition of 1 mg/mL FLAG peptide and 10 mM EDTA.

Radioligand Binding: All equilibrium competition radioligand binding studies were conducted in a final volume of 200 µL containing HDL-receptor, radioligand, a titration of unlabeled competitor, and the presence or absence of the indicated transducer protein. All components were diluted in assay buffer containing 20 mM HEPES, pH 7.4, 100 mM NaCl, and 1 mg/mL bovine serum albumin (BSA). Radioligands used in β2AR, M2R, and MOR competition binding experiments were [125I]-Cyanopindolol (CYP; 60 µM), [3H]—N-Methyl-Scopolamine (NMS; 1 nM), and [3H]-Naloxone (2.5 nM), respectively. G protein or βarr1 were used at a final concentration of 100 nM or 1 µM, respectively, unless specified otherwise. Binding reactions proceeded at room temperature and were harvested onto glass-fiber filters (GFB) with 0.3% polyethyleneimine (PEI) using a 96-well Brandel harvester. Binding data were analyzed in GraphPad Prism using a sigmoidal dose-response curve fit, and differences in log IC50 values were analyzed by one-way ANOVA.

G protein GTPase Assay: The GTPase activity of Gαs or Gαi was measured in vitro using the GTPase Glo Assay (Promega) with the following modifications. Final reaction buffer consisted of 20 mM HEPES, pH 7.4, 100 mM NaCl, 10 mM MgCl2, and 1 mg/mL BSA. HDL-β2AR (4 nM), -M2R (100 nM), or MOR (100 nM) was incubated in the absence or presence of the indicated agonist (5 µM) and βarr1 (1 µM) for 15 min at room temperature. The antibody fragment Fab30 (1 µM) was included with βarr1 to stabilize its interaction with the ligated receptor C terminus (Shukla A K, et al. (2013) *Nature* 497(7447):137-141). G protein (500 nM) and GTP (2.5 µM) were subsequently added, and reactions proceeded for 1 h at room temperature before addition of GTPase Glo reagent and ADP, as described in the manufacturer's protocol.

Example 1

This example demonstrates that the binding interaction of βarr with the β2-adrenergic receptor (β2AR).

Figure 1:
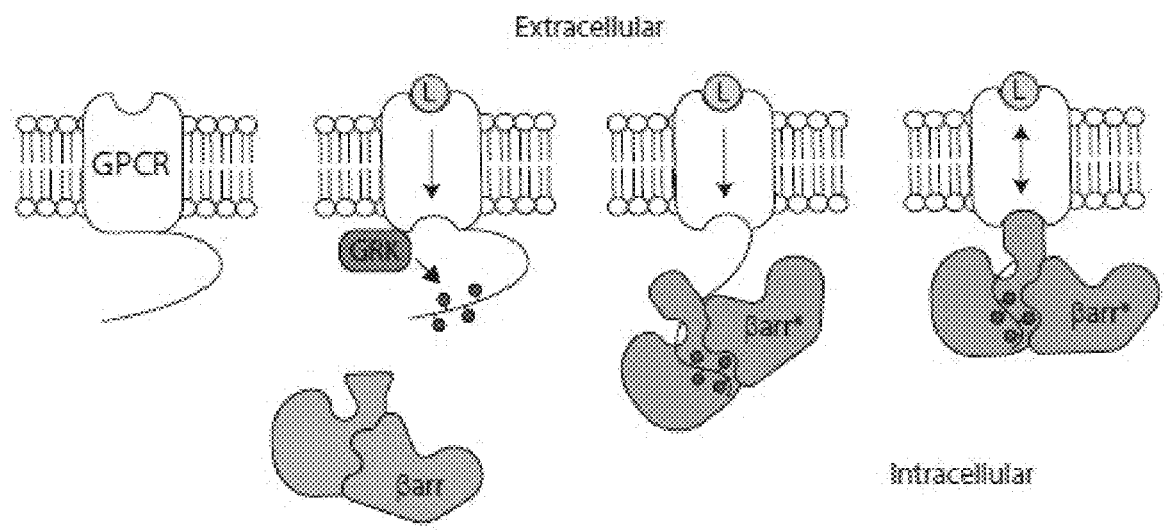
Figure 2A:

The binding of βarr to GPCRs is mainly initiated through an interaction with the phosphorylated receptor C terminus, and conformational changes induced in βarr by this interaction promote coupling to the receptor TM core, as shown in FIG. 1. Co-immunoprecipitation experiments confirmed that heterotrimeric Gs protein, but not βarr1, can interact with purified non-phosphorylated β2-adrenergic receptor (β2AR), as shown in FIG. 2A.

Figure 2B:
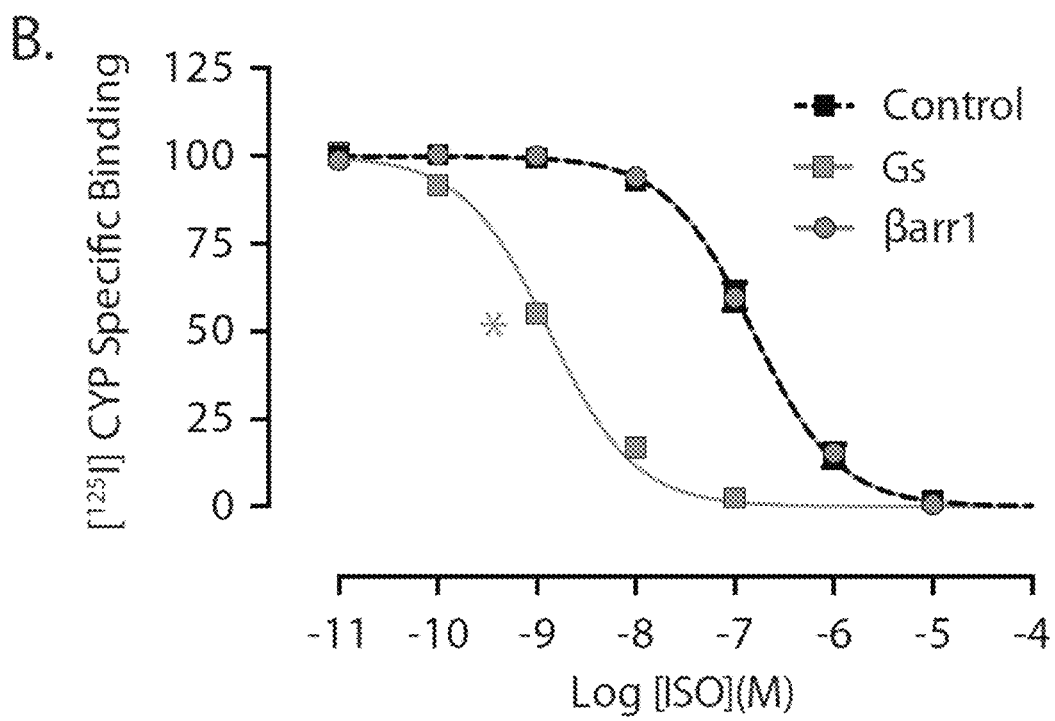

To verify that this apparent lack of interaction with βarr is not simply due to poor complex stability, two assays capable of detecting complex formation in situ were performed. First, competition radioligand binding was used to measure the allosteric effects of transducers on ligand binding to the receptor. As described by the ternary complex model, first for G proteins and later for βarrs, ligand-induced changes in receptor conformation enhance the binding and affinity of transducers, which reciprocally increase ligand affinity by stabilizing an active receptor state (De Lean A, et al. (1980) *J Biol Chem* 255(15):7108-7117., Gurevich V V, et al. (1997) *J Biol Chem* 272(46):28849-28852). When wild-type (WT) β2AR was reconstituted in high-density lipoprotein (HDL) particles to mimic a cellular membrane environment (Denisov I G & Sligar S G (2016) *Nat Struct Mol Biol* 23(6):481-486), G protein enhanced the affinity of the full agonist isoproterenol for non-phosphorylated HDL-β2AR by nearly 1000-fold, as expected, but βarr1 had no effect even at micromolar concentrations, as shown in FIG. 2B.

Figure 2C:
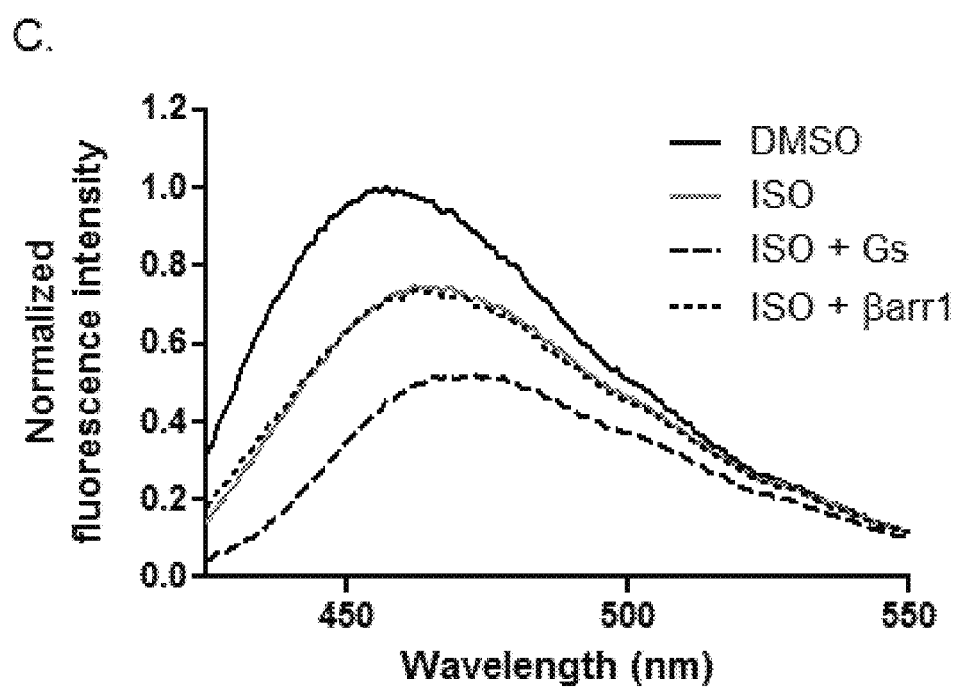

Second, to directly monitor β2AR conformational changes associated with activation, the C265 at the cytoplasmic end of TM6 was labeled with monobromobimane, an environmentally sensitive fluorophore. Receptor activation leads to an outward movement of TM6 that places the bimane label in a more solvent-exposed position, causing a decrease in fluorescence and a shift in λmax (Yao X J, et al. (2009) *Proc Natl Acad Sci USA* 106(23):9501-9506). Indeed, isoproterenol reduced β2AR-bimane fluorescence compared to control (DMSO), and addition of Gs but not βarr1 further attenuated fluorescence, as shown in FIG. 2C.

The results of this example demonstrate that non-phosphorylated β2AR fails to form a productive interaction with βarr.

Example 2

This example describes the preparation of a complex comprising a chimeric GPCR and βarr1 in accordance with the present disclosure.

Figure 3D:
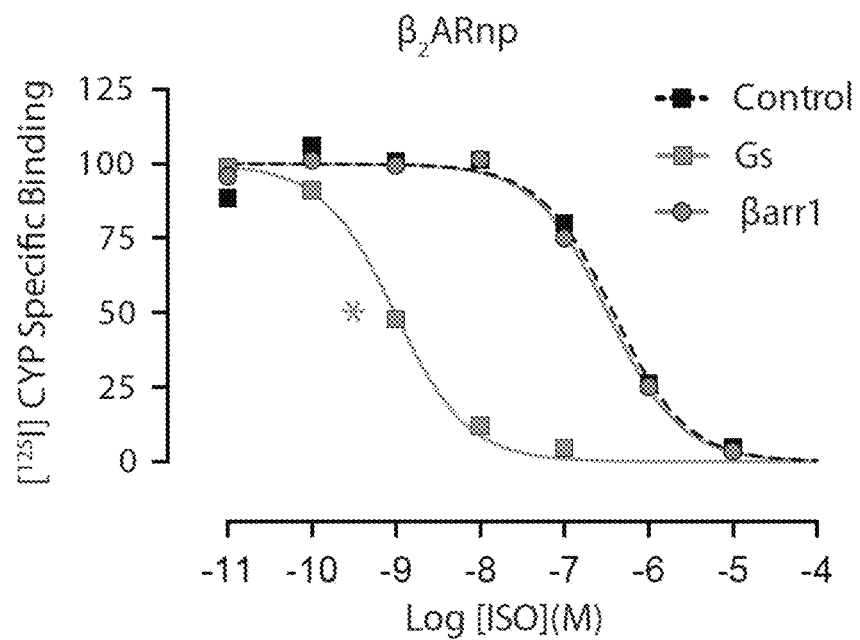
Figure 7A:
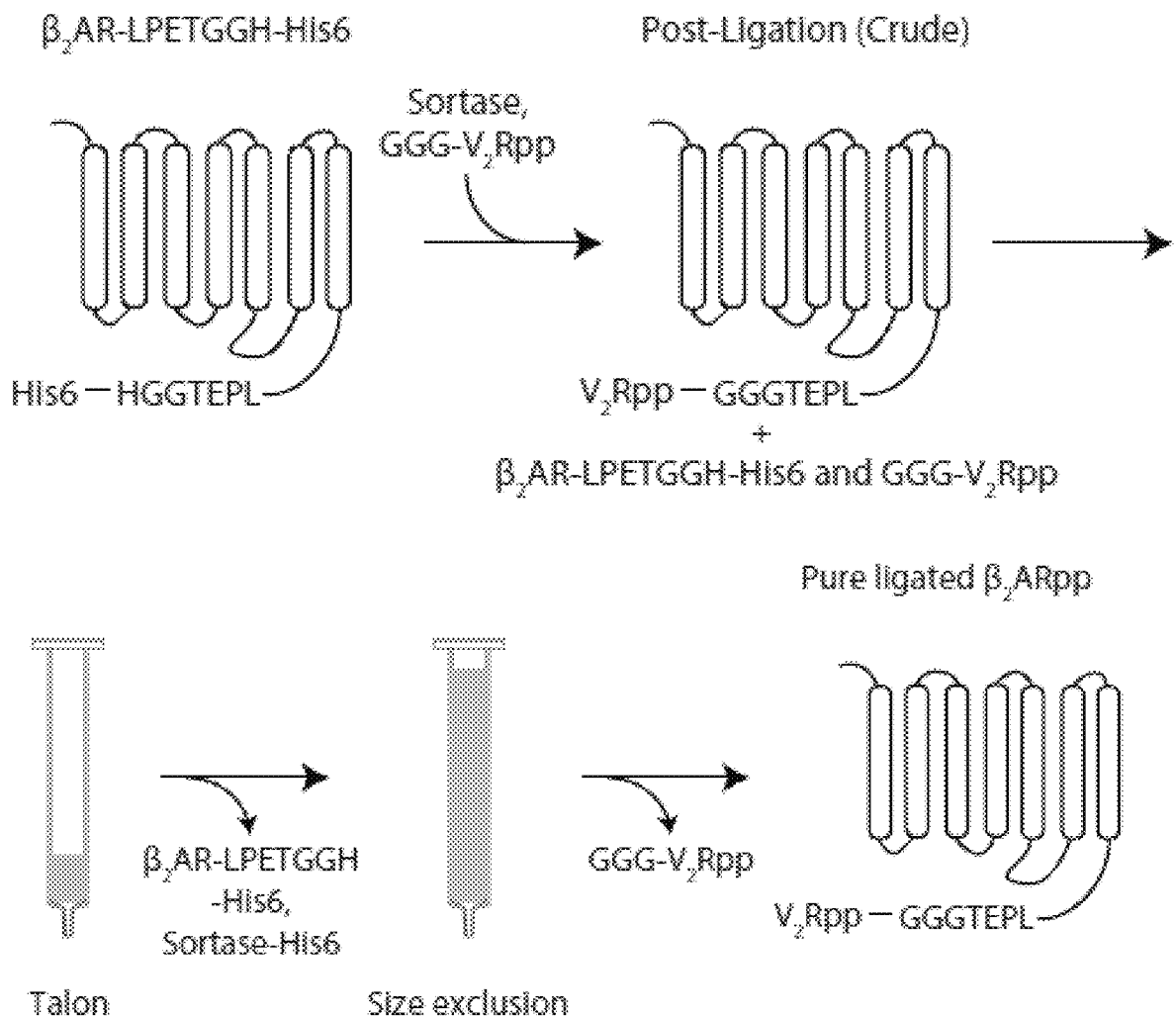
FIG. 7B shows protein (coomassie) staining of $\beta_2$ARpp purification.
FIG. 7C shows size exclusion chromatographic analysis of $\beta_2$ARpp.
Figure 7B:
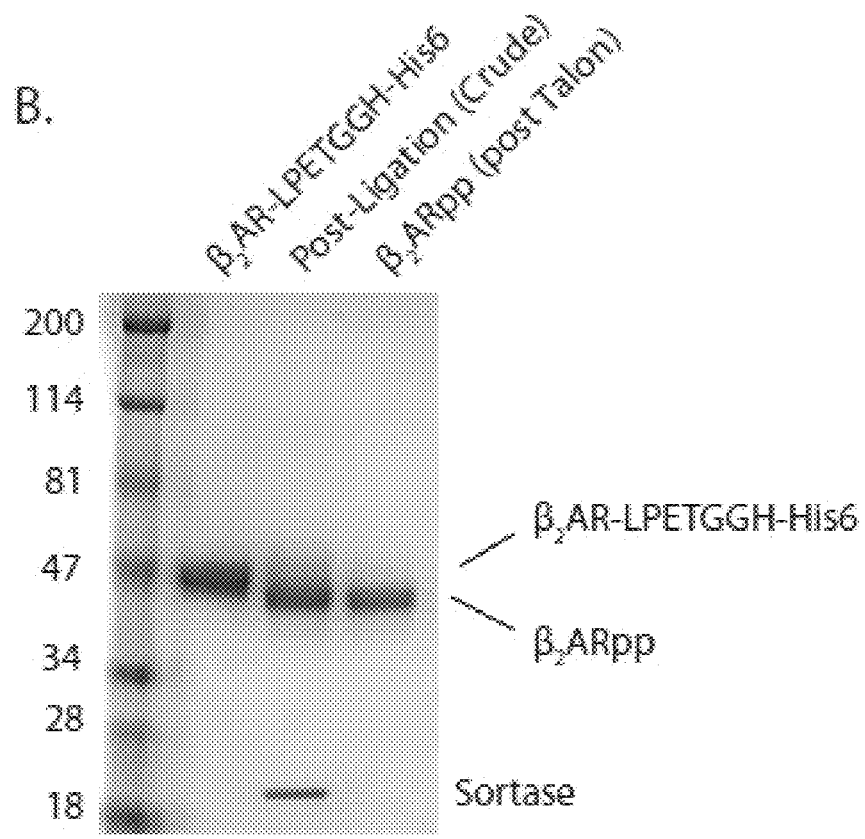
Figure 7C:
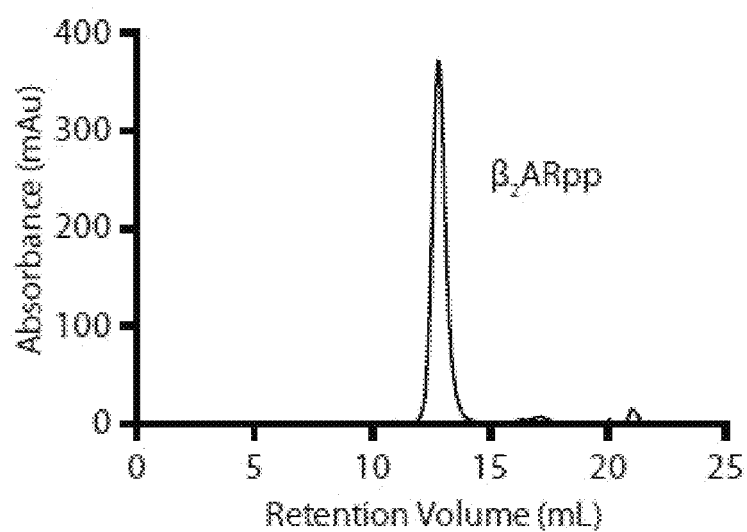

Phosphorylation of the $\beta_2AR$ was induced using the prokaryotic enzyme sortase to ligate a synthetic phosphorylated peptide onto the receptor C terminus (FIGS. 3A and 7A). This strategy quantitatively yielded receptor with a defined, homogeneous phosphorylation pattern, which is difficult to achieve or validate with either in cellulo or in vitro GRK phosphorylation. Briefly, a phosphopeptide (pp) derived from the C terminus of the vasopressin-2-receptor ($V_2R$) was ligated to the C-terminus of β2AR, based on previous crystallographic and biophysical data indicating that $V_2$Rpp binds to βarr with high affinity and effectively primes it for interaction with GPCRs' TM core (Shukla A K, et al. (2013) *Nature* 497(7447):137-141). In contrast to wild-type (WT) β2AR (FIG. 2A), phosphorylated $\beta_2AR$ ($\beta_2ARpp$) immunoprecipitated both Gs and βarr1 (FIG. 3B). βArr1 enhanced isoproterenol affinity for the $\beta_2$ARpp by 9-fold compared to 800-fold by Gs (FIGS. 3C and 8A). However, as for Gs, βarr1 did not increase the binding of the antagonist ICI-118,551 (FIG. 8B). The βarr1-mediated increase in agonist affinity required phosphorylation of $\beta_2$ARpp since ligation of a non-phosphorylated $V_2R$ peptide or phosphatase treatment abrogated βarr1's allosteric effect (FIGS. 3D and 8C).

Figure 3E:
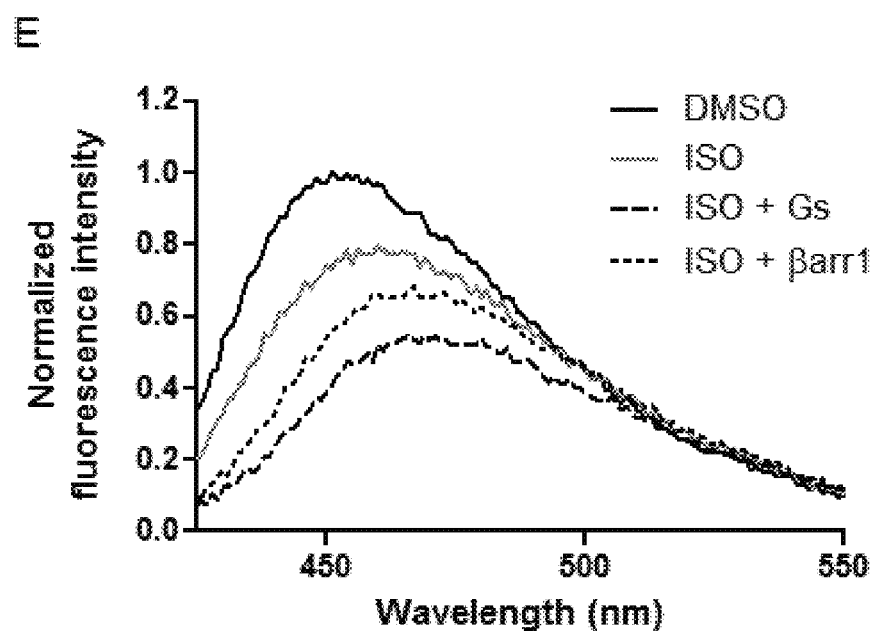

While βarr1 augmented isoproterenol's decrease in the fluorescence of $\beta_2$ARpp-bimane, its effects were less profound than those of G protein (FIG. 3E), consistent with the ~100-fold difference in the cooperativity between G protein and βarr1 observed by radioligand binding (FIG. 3C). These findings suggest that despite binding to a similar pocket, G protein and βarr differ substantially in the strength of their allosteric interactions with the β2AR TM core.

Figure 4A:
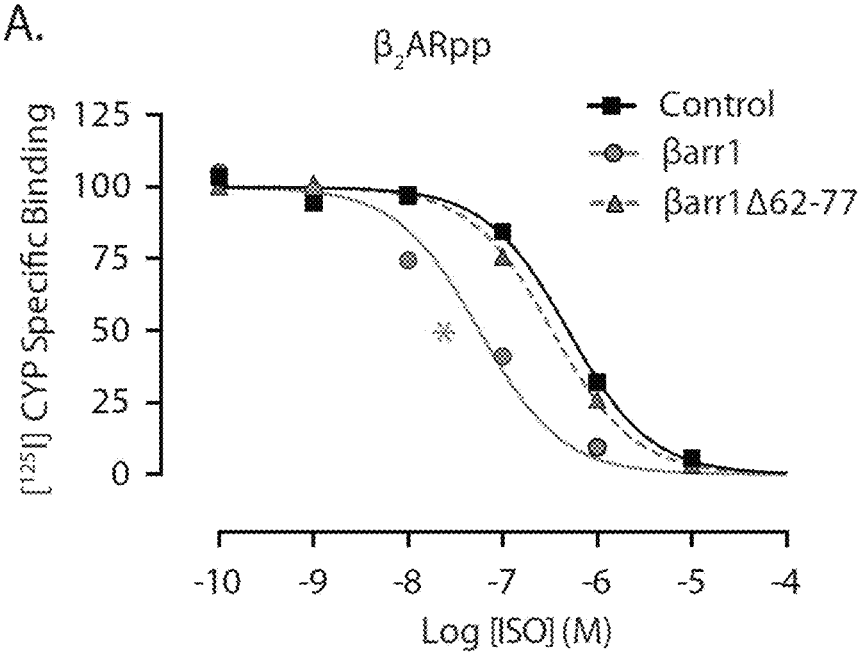
Figure 4B:
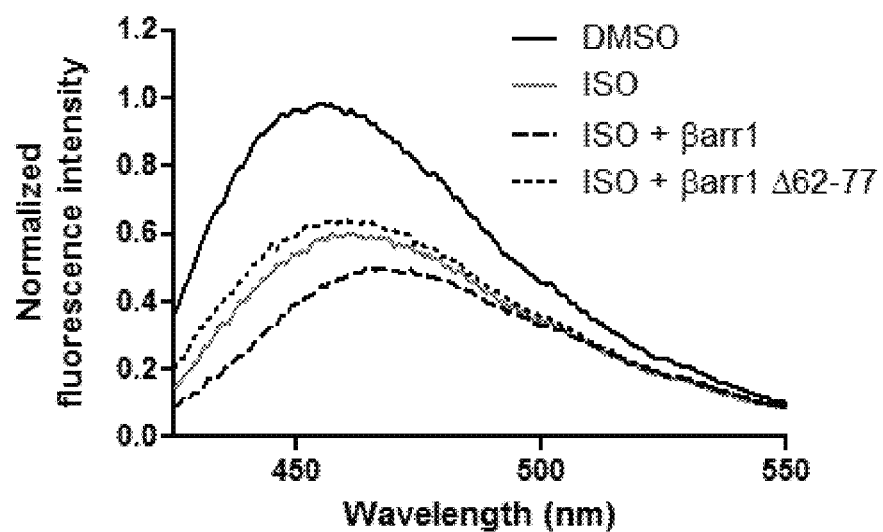

The above system allowed for rigorous assessment of the contributions of specific regions within each protein that have been implicated in mediating the TM core/βarr interaction. For example, the "finger loop" region of βarr1 is extended upon βarr's binding to phosphorylated receptors and is believed to insert into the TM core. This region has been reported to be essential for an engaged conformation of βarr1 with the TM core of in cellulo phosphorylated $\beta_2AR$, as assessed by negative stain electron microscopy using a βarr1 finger loop-deleted mutant (Cahill T J, 3rd, et al. (2017) *Proc Natl Acad Sci USA* 114(10):2562-2567). This same mutant, βarr1Δ62-77, failed to stabilize an active state of $\beta_2$ARpp by competition radioligand binding (FIG. 4A) and bimane fluorescence (FIG. 4B), consistent with previous findings.

Figure 4C:
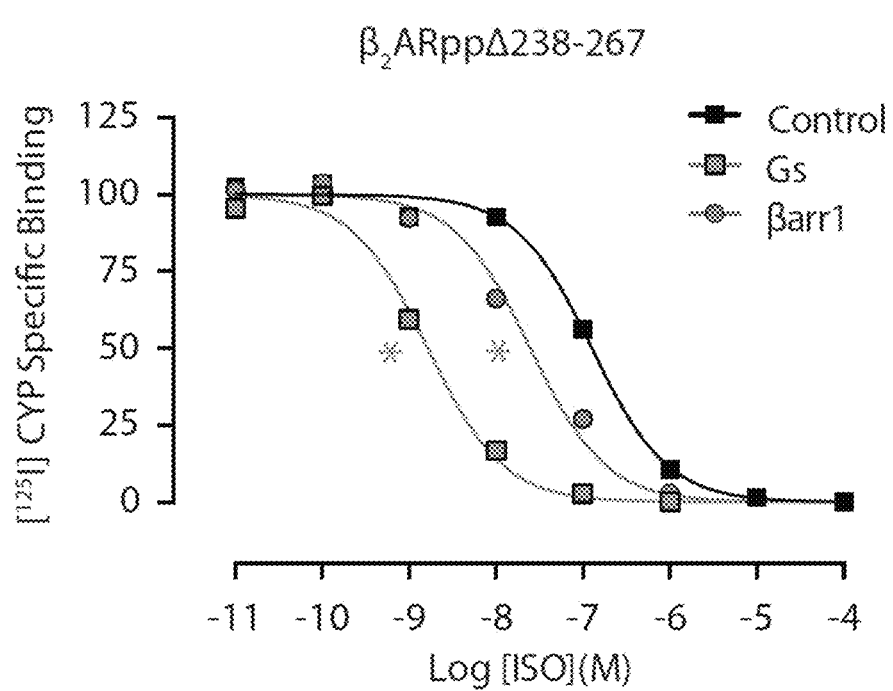

It has been suggested that intracellular loop three (ICL3) of the $\beta_2AR$ is critical for engagement of βarr1 with the TM core (Kumari P, et al. (2016) *Nat Commun* 7:13416.). The phosphopeptide-ligated version of a previously reported deletion mutant, β2ARppΔ238-267, retained a normal affinity for the agonist isoproterenol when reconstituted in HDL particles (FIG. 4C). Surprisingly, agonist affinity increased approximately 10-fold in the presence of βarr1 (FIG. 4C), which was comparable to βarr1's effect on WT $\beta_2$ARpp (FIG. 3C).

The results of this example demonstrate the generation of a receptor complex that exhibits a homogeneous phosphorylation pattern, and that the finger loop of βarr, but not the β2AR ICL3, is required for the TM core interaction.

Example 3

This example describes the preparation of a complex comprising a chimeric muscarinic acetylcholine receptor 2 (M2R) or μ-opioid receptor (MOR) and βarr1 in accordance with the present disclosure.

Figure 5C:
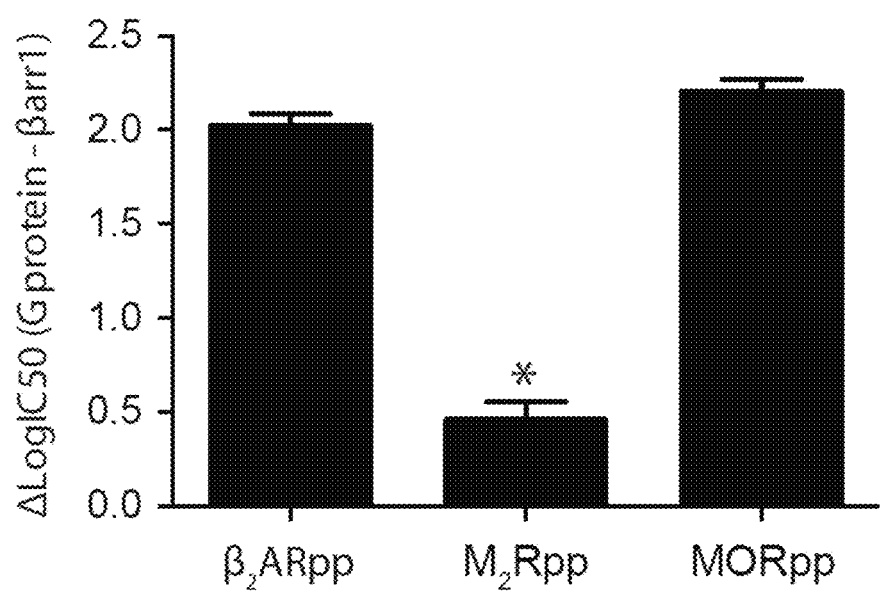

For the $\beta_2AR$, the TM core's allosteric communication with G protein is substantially stronger than it is with βarr. To determine if this is a conserved phenomenon among other GPCRs, the allosteric coupling of G protein and βarr at the muscarinic acetylcholine receptor 2 ($M_2R$) and μ-opioid receptor (MOR) was investigated. Using the sortase ligation strategy described in Example 2 for the $\beta_2AR$, the $V_2$Rpp was ligated onto the C termini of purified $M_2R$ ($M_2$Rpp) and MOR (MORpp) (FIG. 9A), the receptors were reconstituted into HDL particles, and the allosteric coupling of their cognate G protein (Gi heterotrimer) and βarr was measured using competition radioligand binding. Competitor ligands that were full agonists and exhibited similar affinities for their respective receptors as isoproterenol does for the $\beta_2AR$ were selected. As observed for the $\beta_2AR$, G protein induced more than a 100-fold increase in agonist affinity for both $M_2$Rpp (carbachol, FIG. 5A) and MORpp (DAMGO, FIG. 5B), consistent with previous reports (Kruse A C, et al. (2013) *Nature* 504(7478):101-106, Huang W, et al. (2015) *Nature* 524(7565):315-321). βArr1 enhanced agonist affinity for both M2Rpp and MORpp in a phosphorylation-dependent manner (FIGS. 5A, 5B, 9B, and 9C), but βarr1 increased carbachol affinity for $M_2$Rpp by 57-fold compared to only 2- and 9-fold for MORpp and $\beta_2$ARpp, respectively (FIGS. 5A, 5B, and 9D). A summary of transducer allosteric binding at each receptor is shown in FIG. 5C, which shows a 100-fold difference between G protein and βarr effects on agonist affinity for the $\beta_2$ARpp and MORpp but less than a 3-fold difference with $M_2$Rpp. The comparable effects of G protein and βarr at the $M_2$Rpp were not carbachol-specific but were also observed with the agonist iperoxo (FIGS. 9E and 9F). βArr1's effects at the $M_2$Rpp also appeared to be dependent on the transmembrane core interaction, as deletion of the finger loop eliminated its allosteric coupling (FIG. 9G).

The results of the example demonstrate that, even for GPCRs which preferentially couple to the same G protein isoform as the $\beta_2AR$, such as the $M_2R$ and the MOR, allosteric communication with G protein does not always vary proportionally to allosteric communication with βarr.

Example 4

This example demonstrates the function and stability of the chimeric receptor complexes described herein.

The ternary complex model posits that the observed enhancement of agonist affinity in the presence of βarr must be reciprocated by an equivalent increase in βarr's affinity for the receptor transmembrane core (De Lean A, et al. (1980) *J Biol Chem* 255(15):7108-7117). Thus, the strength of βarr engagement with the receptor core would be expected to follow the same rank order of allosteric cooperativity among the three receptors tested. The degree of βarr1 engagement was assessed by site-specifically labeling its finger loop with monobromobimane (βarr1-bimane), as coupling to a receptor's TM core results in an increase in fluorescence due to reduced solvent exposure of the label (Sommer M E, et al (2007) *J Biol Chem* 282(35):25560-

Figure 6A:
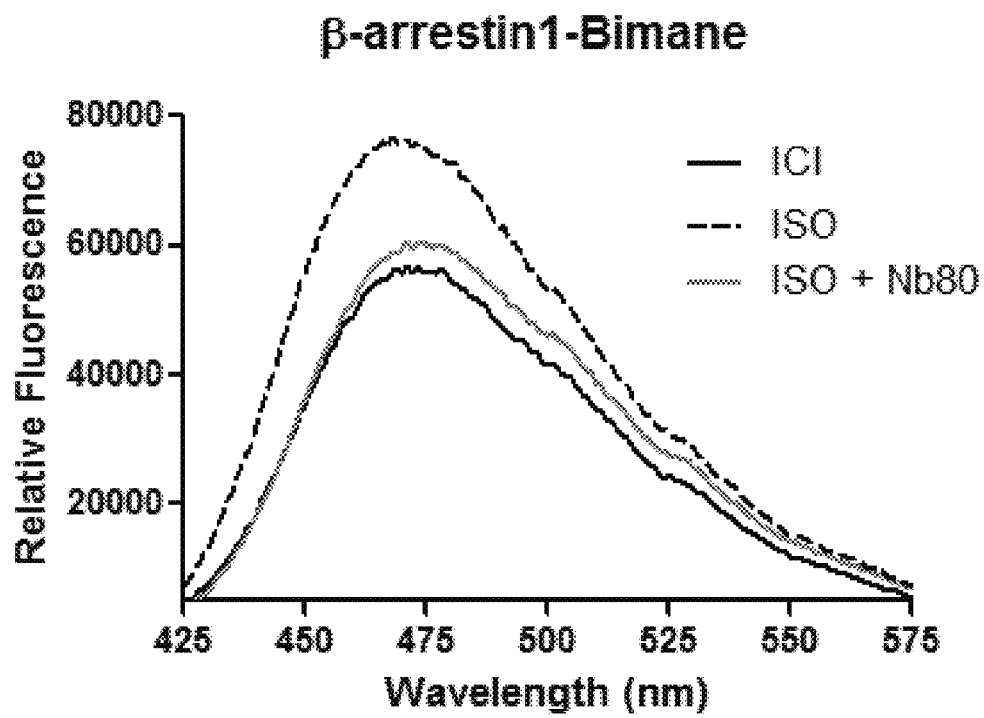
Figure 6B:
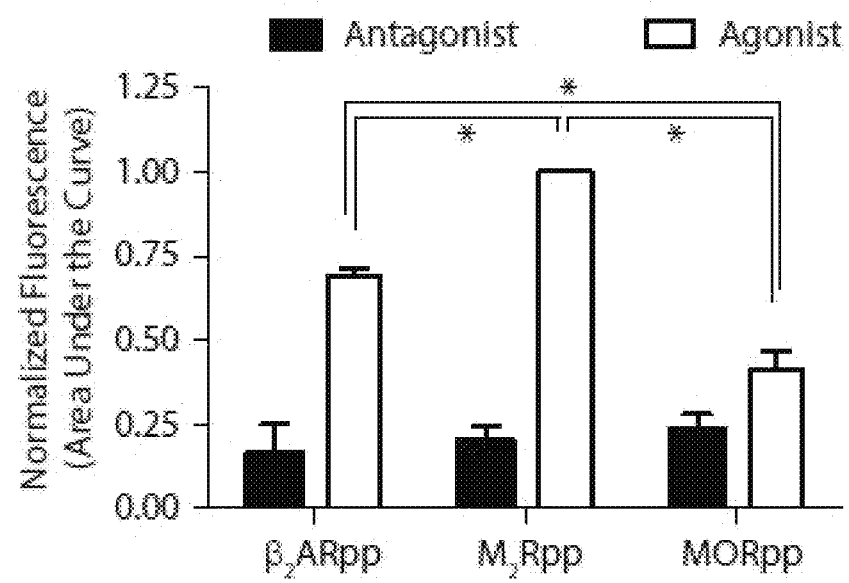

25568, Hanson S M, et al. (2006) *Proc Natl Acad Sci USA* 103(13):4900-4905). As expected, (βarr1-bimane fluorescence increased for β$_2$ARpp stimulated with isoproterenol compared to the antagonist ICI-118,551 (FIG. 6A and FIG. 10A). Importantly, the single domain antibody Nb80, which binds to agonist-activated β$_2$AR in the same region as G protein, competitively blocked the agonist-induced increase in fluorescence (FIG. 6A). These results confirm that the agonist effects on βarr1-bimane are indeed mediated through interaction with β$_2$ARpp's TM core. Comparison of βarr1-bimane's response to agonist stimulation of β$_2$ARpp, M$_2$Rpp, and MORpp showed that M$_2$Rpp displayed the highest level of agonist-induced βarr1-bimane engagement (FIG. 6B and FIG. 10A-C), consistent with the observed allosteric cooperativities of these receptors.

Figure 6C:
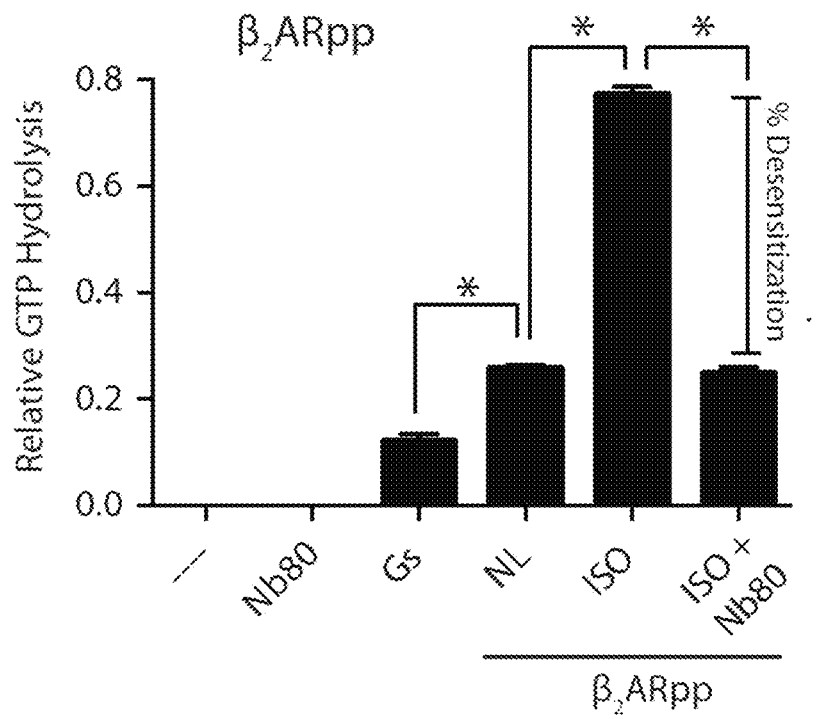
Figure 6D:
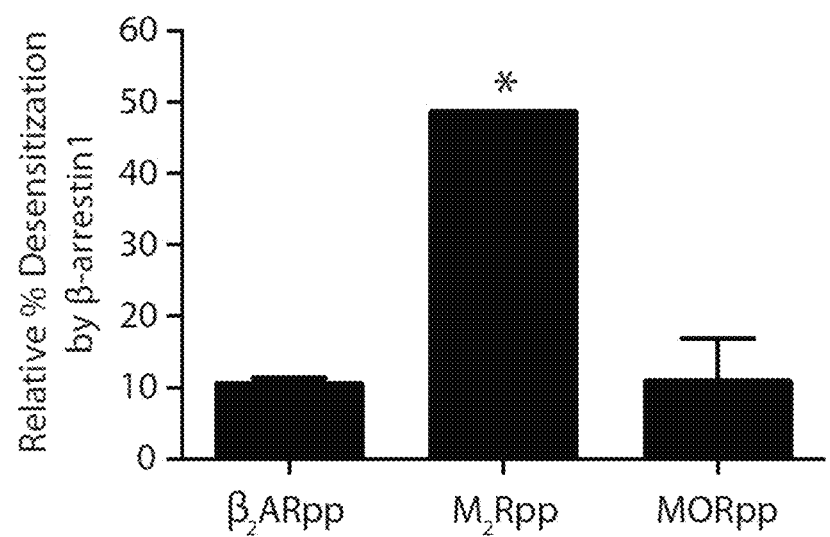

One mechanism by which βarr desensitizes receptors' activation of G protein signaling is steric occlusion of the TM receptor core. It was hypothesized that βarr might more efficiently desensitize GPCRs such as the M$_2$R—those for which βarr has similar allosteric binding properties as G protein—compared to GPCRs with very divergent transducer coupling, such as the β$_2$AR and the MOR. To test this, an in vitro GTPase activity assay was performed that can quantitatively measure agonist-induced receptor activation of G protein. As shown in FIG. 6C, addition of isoproterenol to the β$_2$AR enhanced G protein activation as measured by an increase in GTP hydrolysis, which was blocked by competitive binding of Nb80. A similar agonist-induced increase in GTPase activity was observed for both M$_2$Rpp and MORpp (FIG. 11). Desensitization, or inhibition of GTP hydrolysis, by βarr was significantly elevated for M$_2$Rpp compared to MORpp and β$_2$ARpp (FIG. 6D and FIG. 11).

The results of this example demonstrate that that the efficiency of βarr-mediated receptor desensitization in vitro correlates with the strength of the receptor's allosteric interaction with βarr relative to G protein.

Example 5

Sortase-ligated β$_2$ARpp for DNA-encoded Library Screen. Purified human β$_2$AR or β$_2$ARpp was reconstituted in detergent-free high density lipoprotein (HDL) particles. HDL reconstitution was performed using a biotinylated version of the membrane scaffolding protein ApoA1. In addition to providing the receptor with a native-like membrane environment, the biotinylated HDL particles provide an excellent immobilization scheme that avoids any perturbations at the receptor during the screening process. Receptors containing biotinylated-HDLs can be efficiently captured on NeutrAvdin beads. For positive selections (rounds 1 and 2), HDLs were incubated with a molar excess of appropriate transducer proteins, BI-167107, and Neutravidin beads to initiate complex formation and immobilize the complexes. For complexes with Gs, β$_2$AR HDLs were incubated with His-tagged heterotrimeric Gs and Nb35 (Rasmussen et al., *Nature* 2011, 477, 549-555). For complexes with β-arrestin, β$_2$ARpp HDLs were incubated with β-arrestin1 and His-tagged Nb25. The beads were transferred to a column and washed to remove unbound proteins. Stability results are shown in FIG. 12.

DNA-encoded Library Test Screen. A test library of approximately 10$^{14}$ DNA-tagged small molecules was applied to the beads, incubated at room temperature, and then washed extensively. Specifically bound molecules were eluted twice by applying buffer containing 10% Fos-choline to the beads and incubating at 37° C. and then 72.5° C. The number of recovered compounds was determined by qPCR on an aliquot of the combined eluates. Compounds were purified from the eluate using a Qiagen Nucleotide Removal Kit before beginning the next round of selection. For counter selection (round 3), complexes were formed in the presence of NiNTA beads, and unbound molecules were recovered and analyzed. Results of the test screen are shown in FIG. 13.

Example 6

Screening and identification of primary β2 PAM hits. Using a recently developed approach for screening DNA-encoded small molecule libraries (DELs) against GPCRs, over 500 million unique DNA-encoded small molecules were screened to obtain positive allosteric modulators (PAMs) at the β2-adrenergic receptor (β2AR). In order to increase chances to get PAMs, the orthosteric site of the receptor was occupied by a high affinity β-agonist BI-167107, which shifted the β$_2$AR population toward active conformations (FIG. 14A). Further, purified human β$_2$ARs were reconstituted in detergent-free high density lipoprotein (HDL) particles (FIGS. 14A and 14B). HDL reconstitution was performed using a biotinylated version of the membrane scaffolding protein ApoA1. In addition to providing the receptor with a native-like membrane environment, the biotinylated HDL particles provide an excellent immobilization scheme that avoids any perturbations at the receptor during the screening process. Receptor containing biotinylated-HDLs can be efficiently captured on NeutrAvdin beads (FIG. 14B), and have a comparable affinity for antagonist binding to that of β2ARs in membrane preparations (FIG. 14C). By competitive radioligand binding assays, the β2ARs in HDL particles can functionally couple to heterotrimeric Gs (FIG. 14D).

Using the BI-167107-occupied β$_2$AR in HDL particles, four different DELs were screened, each of which comprised more than 100 million unique compounds, to isolate molecules specifically binding to the active state of the receptor. The total number of molecules in each library was 0.5-1× 10$^{14}$. Three rounds of iterated selection (FIG. 14A) with each of the libraries were performed until the molecule number was decreased to around 1×10$^6$, which was monitored by quantitative polymerase chain reaction (qPCR). Following amplification of preserved DNA barcodes by PCR, the samples were subjected to Next-generation sequencing (NGS) to identify compounds that outlasted the entire selection procedure. Sequences having significant copy numbers (i.e high signal-to-noise ratio) were deconvoluted to their corresponding chemical structures from the database. Through this analysis, 50 compounds were determined as primary candidates that possibly bind to the β$_2$AR (Table1) and named them Compounds 1-50.

These compounds were synthesized without their code DNA in a small scale to evaluate their activity as PAMs.

TABLE 1

DNA-encoded libraries used in screening

| Library ID* | Library structure** | Fragment combination*** | Library Size (Million) | Hits resynthesized |
|---|---|---|---|---|
| 108 | 2-mer | 11,279 × 13,440 | 151.6 | 15 |
| 122 | 3-mer | 384 × 329 × 960 | 121.3 | — |

TABLE 1-continued

DNA-encoded libraries used in screening

| Library ID* | Library structure** | Fragment combination*** | Library Size (Million) | Hits resynthesized |
|---|---|---|---|---|
| 123 | 2-mer | 8,807 × 14,496 | 127.7 | 5 |
| 126 | 2-mer | 5,814 × 18,513 | 107.6 | 30 |

*For more detail on the encoding libraries, see Kontijevskis, (2017) *J Chem Inf Model* 57: 680-699.
**Number of encoding positions in DNA-encoded combinatorial library
***Number of fragments in each encoding position.

PAMs are expected to potentiate binding of orthosteric agonists to GPCRs and coupling of transducer proteins, G protein and β-arrestin to receptors. Accordingly, these 50 potential hits from the selection were tested for their ability to increase binding of a radiolabeled agonist, $^3$H-fenoterol ($^3$H-FEN) to the β2AR in membrane preparations, both in the absence and presence of transducers (FIGS. 14E and 14F). Through this test, seven structurally-related compounds were identified as shown in FIG. 14G, including compound-6 (Cmpd-6) that showed the strongest activity among the compounds, as potential β2AR PAMs. Compounds 6 and 43 were resynthesized in a large scale for further characterization of their PAM activity. To assess direct molecular interaction between Cmpd-6 and the agonist-bound, active β$_2$AR, isothermal titration calorimetry (ITC) was employed. The values summarizing binding affinity ($K_D$), stoichiometry (N), and thermodynamic parameters are shown in FIG. 14H.

Example 7

PAM activity of Cmpd-6 and -43 in β2AR-mediate downstream functions. To further evaluate the PAM activity of Cmpd-6 and -43 in β2AR-mediated down-stream functions, β2AR agonist-induced G protein cAMP production and β-arrestin recruitment to the receptor was determined in the presence of these compounds using cellular assays. It is well known that the second messenger generation process downstream of GPCR activation has high signal amplification compared to stoichiometric reactions such as β-arrestin recruitment to the receptor. Accordingly, endogenously expressed β2AR was used in the assay cells to measure cAMP production, while β-arrestin recruitment was measured using stably overexpressed β2V2R to achieve similar extents of signals between these two assays. The β2V2R, a chimeric receptor with a V2R tail at the C-terminus, displays stronger and more stable agonist-promoted β-arrestin binding than the native β2AR while retaining the pharmacological properties of the native β2AR. Both Cmpd-6 and -43 increased the ability of an agonist, isoproterenol (ISO) to activate G protein-mediated cAMP production through the β2AR in a dose-dependent way (FIGS. 15A and 15B). Cmpd-6 and -43 increased the maximal response induced by ISO as well as potentiated the EC50 value of the ISO dose-response, which was apparent in its left-shifted dose-response curve. In this assay, Cmpd-6 shows stronger activity than Cmpd-43, which is consistent with the preliminary data showing the extent of doses-dependent increases in $^3$H-FEN binding to the β2AR by these compounds shown in FIG. 14F. A comparable pattern of the results was obtained with Cmpd-6 and -43 in the assay monitoring agonist-induced β-arrestin recruitment to the β2V2R (FIGS. 15C and 15D).

Increases in the ISO-induced maximal response by Cmpd-6 and -43 in both assays suggests that ISO may act as a partial agonist and does not reach the full response available in this system, allowing Cmpd-6 and -43 to further increase the maximal response by ISO. To verify this, cAMP production by the overexpressed β2AR was monitored in the presence of Cmpd-6, the system that has much higher amplification (FIG. 19). Cmpd-6 promoted leftward shifts of the ISO dose response EC50 value, with increases in the basal activity in a dose-dependent way, but not increases in the ISO-stimulated maximal response. This shows that even a full agonist such as ISO can act as a partial agonist depending on the assay system, which would not have been suspected without the cooperativity displayed by these new PAMs. Overall, the results demonstrate that Cmpd-6 and -43 have PAM activity for β2AR-mediated down-stream functions, and that Cmpd-6 has stronger PAM activity than Cmpd-43.

Example 8

Cmpd-6 and -43 potentiate the binding affinity of agonists for the β2AR. A hallmark of GPCR PAM molecules is that they allosterically stabilize the active conformation of the agonist-bound receptor, as do transducer proteins, G protein and β-arrestin, as illustrated in the GPCR ternary complex model. Since PAM-mediated stabilization of the GPCR active conformation leads to potentiation of agonist binding affinity for the receptor, Cmpd-6 and -43 were tested for their effects on the binding of an agonist to the β2AR. For this, orthosteric agonist ISO competition binding to the β2AR reconstituted in HDL particles was assayed against a radiolabeled antagonist $^{125}$I-cyanopindolol (CYP) in the presence of Cmpd-6 and -43 (FIGS. 16A and 16B). As expected for PAMs, both compounds potentiated the binding of ISO to the β2AR, as evidenced by the robust shift of the dose-dependent competition curve of ISO to the left in the presence of these compounds at various concentrations. Cmpd-6 potentiated the IC50 value of ISO close to 50-fold, which was substantially more than the ~30-fold change elicited by Cmpd-43. Comparable extents of the ISO dose-response curve shift induced by Cmpd-6 and -43 in a radioligand competition binding experiment were also obtained with membranes prepared from β2AR-overexpressing cells (FIGS. 16C and 16D).

The result shown in FIG. 16E further confirms the PAM activity of Cmpd-6 and -43 for increasing the binding of an orthosteric agonist to the β2AR. Cmpd-6 and -43 dose-dependently increase the binding of the radiolabeled orthosteric agonist $^3$H-FEN to the β2AR expressed in cell membranes, consistent with the result in the preliminary experiment with these compounds synthesized in a small scale (FIGS. 14E and 14F). Again Cmpd-6 is more efficacious than Cmpd-43 in increasing $^3$H-FEN binding to the β2AR. Further, the low micro-molar affinity (EC50) value of Cmpd-6 obtained in this assay is comparable to its $K_D$ value measured for its direct interaction with the β2AR by ITC analyses (FIG. 14H). Another feature of allosteric molecules observed in both binding experiments is the "ceiling" effect. The increases in the binding of both agonists, ISO (FIGS. 16A and 16B) and FEN (FIG. 16B) were saturated over increasing concentrations of these allosteric compounds.

Example 9

Cmpd-6 stabilizes the agonist-induced active conformation of the β2AR. Agonist-induced activation of the β2AR causes the outward movement of transmembrane helix 6 (TM6), which can be detected by labeling of cysteine-265 at the intracellular base of TM6 with monobromobimane, an environmentally sensitive fluorescent label. Following receptor activation, the outward movement of TM6 leads to decreases in fluorescence intensity and increases in the maximum wavelength for emission. Cmpd-6 alone induced decreases in overall fluorescence intensity, but not increases in the maximum wavelength from the bimane-labeled β2AR in HDL particles (FIG. 17). On the other hand, ISO decreased fluorescence to a similar extent but also increased the maximum wavelength. This suggests that the conformational ensemble of the β2AR when bound to Cmpd-6 alone is similar to, but distinct from, that induced by orthosteric agonists. Interestingly, Cmpd-6 further potentiates ISO-induced decreases in the amount of fluorescence and increases in the maximum wavelength from the bimane-labeled β2AR. The Cmpd-6-mediated potentiation of ISO effects is similar in magnitude to that observed with an allosteric nanobody80 (Nb80) that mimics the G protein-stabilized active conformation of the agonist-bound β2AR. These data demonstrate that Cmpd-6 stabilizes the active conformation of the agonist-bound β2AR, engaging the outward movement of TM6 to an extent comparable to that mediated by transducers like G protein.

Example 10

Functional cooperativity of Cmpd-6 with transducers at the β2AR. The data from the cellular assays (FIGS. 15A-15D) strongly supports the PAM activity of Cmpd-6 and suggests a functional cooperativity between the compound and the transducers Gs and β-arrestin. To confirm this co-operative property of Cmpd-6, competition radioligand binding was performed on membrane preparations expressing β2AR C-terminal fusions with Gsα or β-arrestin1 (FIGS. 18A and 18B). Compared to β2AR alone, both transducer fusions revealed the expected high-affinity coupling to the receptor with a left-shift in ISO dose response curves. Importantly, addition of Cmpd-6 at β2AR fusions, and compared to uncoupled receptor, enhanced both Gsα- and β-arrestin1-mediated high-affinity coupling to the receptor and also resulted in a significant potentiation of ISO affinity. The PAM activity of Cmpd-6 was also assessed by dose response binding of the radiolabeled orthosteric agonist $^3$H-FEN aimed at saturating high-affinity sites on the β2AR (FIGS. 18C and 18D). Compared to no transducer controls, addition of Cmpd-6 or the exogenous transducers, heterotrimeric Gs (at β2AR membranes; FIG. 18C) and β-arrestin1 (at phosphorylated β2V2R membranes; FIG. 18D), robustly increased the high-affinity $^3$H-FEN binding to the receptor. Interestingly, addition of Cmpd-6 together with Gs or β-arrestin1 further enhanced the maximal high-affinity $^3$H-FEN binding. While there was noticeable cooperativity between Cmpd-6 and Gs, this potentiation in $^3$H-FEN binding was prominent in the presence of the G-protein mimic Nb80 (FIG. 20A). Together with the findings from cellular assays, these binding studies demonstrate a positive cooperativity between Cmpd-6 and transducers to modulate high-affinity state agonist binding to the β2AR.

Of note, the data in FIG. 20A also suggest that Cmpd-6 does not occlude transducer coupling to β2AR and likely binds to a potentially unique allosteric site in the receptor. Accordingly, to test whether Cmpd-6 physically competes for binding to the intracellular transducer binding pocket, an ELISA was performed to capture β2AR with the G-protein mimic Nb80 that recognizes agonist-bound active state of the receptor (FIG. 20B). In the presence of the high-affinity agonist BI-167107, and compared to DMSO or the antagonist ICI-118551, there was a marked increase in receptor capture by Nb80. This receptor capture was robustly inhibited in the presence of saturating amounts of a competing nanobody Nb6B9, which is an affinity matured version of Nb80 and thus competes for a common binding epitope on the β2AR. Interestingly, and in contrast to Nb6B9, the addition of a saturating concentration of Cmpd-6 did not alter the capture of β2AR by Nb80. These data suggest that presence of Cmpd-6 does not interfere with transducer-coupling to the β2AR, which further establishes the positive cooperativity between transducers and the compound.

Example 11

The PAM activity of Cmpd-6 is specific for the β2AR. The specificity of Cmpd-6 for the β2AR was evaluated through in vitro agonist competition radioligand binding to the β1AR, the most closely related subtype of adrenergic receptors. In this assay, Cmpd-6 induces a minimal shift of the ISO competition curve for binding to the β1AR against the $^{125}$I—CYP radiolabeled antagonist (FIG. 21A) unlike the robust ISO curve shift by Cmpd-6 observed with the β2AR. This displays that Cmpd-6 specifically induces the high affinity binding of the orthosteric agonist ISO to the β2AR but not to the β1AR. Marginal changes were promoted by Cmpd-6 in the ISO dose response pattern of β1AR-mediated cAMP production (FIG. 21B), which is markedly different from that of the β2AR-mediated response. These findings clearly demonstrate that the PAM activity of Cmpd-6 is specific for the β2AR.

Example 12

PAM activity of Cmpd-6 when the β2AR is stimulated with a range of different agonists. Some allosteric modulators show differential activity depending on orthosteric agonists stimulating the receptor, a phenomenon known as probe-dependence. Cmpd-6 was examined for such differential activity when the orthosteric site of the β2AR is occupied with a range of agonists. These are epinephrine (EPI) and fenoterol (FEN), which are very strong partial, almost full, agonists compared to ISO, and clenbuterol (CLEN), which is a weak partial agonist. The extent of the dose-response curve (IC50 value) shift induced by Cmpd-6 in radioligand ($^{125}$I—CYP) competition binding to the purified β2AR was evaluated with each of these agonists (FIGS. 22A-22D). This permits testing of the allosteric activity of Cmpd-6 solely for binding of an agonist in the absence of transducer-coupling to the receptor. The extent of the curve shift in the presence of Cmpd-6 in this assay essentially followed the efficacy of the tested agonists to induce downstream signaling.

The PAM activity of Cmpd-6 for down-stream signaling of the β2AR when stimulated with each of these four agonists in a dose-dependent way was compared using cell-based functional assays, monitoring cAMP accumulation (FIGS. 22E-22H) and β-arrestin recruitment to the receptor (FIGS. 22I-22L). In general, full and strong partial agonists show greater affinity (EC50 value) shift by Cmpd-6 compared to that observed with the weak partial agonist CLEN. However, CLEN displayed a substantially greater Cmpd-6-mediated increase in the maximal response than did the full agonists. Interestingly, no direct relationship between the extent of the EC50 shift by Cmpd-6 and the efficacy of ISO, EPI and FEN was seen. In functional assays, Cmpd-6 induced a noticeably greater shift with EPI than with ISO and FEN while fold-increases by Cmpd-6 in the maximal response induced by these agonists were comparable. Thus unique probe dependence of Cmpd-6 with this small panel of agonists was not observed.

Example 13

Structure-activity relationships of β2AR PAMs. FIG. 23 illustrates activity data for representative β2AR PAMs. The allosteric effect of Cmpd-6 derivatives on orthosteric agonist $^3$H-FEN binding to the β2AR was tested in the absence and presence of transducers, either trimeric Gs protein or β-arrestin1. Their allosteric activity was also evaluated in ISO-stimulated β2AR downstream signaling, that is G protein-mediated cAMP production and β-arrestin recruitment to the activated receptor. Changes in the Vmax value by Cmpd-6 or each analog at 32 µM are expressed as percentages of the maximal level of the ISO-induced activity in the vehicle (DMSO) control in each assay. Changes in the EC50 value are expressed as fold-shifts compared to the control value obtained the vehicle (DMSO)-treated curve in each assay. Every value represents mean±SEM obtained from four independent experiments done in duplicate. Statistical analyses were performed using 'one-way ANOVA' with 'Dunnelt' post-tests compared to the control (Cmpd-6-treated) value in each assay. *P<0.05, P<0.01, *P<0.001. Rc, receptor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A complex comprising:
   (i) a chimeric G protein-coupled receptor (GPCR) comprising the amino acid sequence LPETGGG (SEQ ID NO: 1) located within the C-terminus of the GPCR and a synthetic phosphopeptide ligated to SEQ ID NO: 1, wherein the synthetic phosphopeptide is derived from the C-terminus of a vasopressin-2-receptor (V2R); and
   (ii) a β-arrestin (βarr) protein bound to the C-terminus of the GPCR.

2. The complex of claim 1, which further comprises an antigen-binding fragment of an antibody (Fab) that specifically binds to the complex.

3. The complex of claim 1, wherein the chimeric GPCR is a member of the adrenergic receptor family, a member of the dopamine receptor family, a member of the opioid receptor family, a member of the muscarinic acetylcholine receptor family, calcitonin receptor (CTR), a cannabinoid receptor, a chemokine receptor, a free fatty acid receptor, G protein-coupled receptor 3, glucagon-like peptide 1 receptor (GLP-1R), a parathyroid hormone receptor, a somatostatin receptor, a sphingosine-1 phosphate receptor, a vasopressin receptor, an angiotensin receptor, or thyroid stimulating hormone receptor (TSHR).

4. The complex of claim 3, wherein the chimeric GPCR is a β2-adrenergic receptor, angiotensin II type 1A receptor, vasopressin V2 receptor, μ opioid receptor (MOR), or muscarinic acetylcholine receptor 2 (M2R).

5. The complex of claim 1, wherein the synthetic phosphopeptide comprises the amino acid sequence ARGRTPPSLGPQDESCTTASSSLAKDTSS (SEQ ID NO: 2).

6. The complex of claim 5, wherein the synthetic phosphopeptide is phosphorylated at residues 5, 8, 15, 17, 18, 20, 21, and 22 of SEQ ID NO: 2.

* * * * *